(12) United States Patent
Mizukawa et al.

(10) Patent No.: US 8,779,159 B2
(45) Date of Patent: *Jul. 15, 2014

(54) COMPOUND OR ITS TAUTOMER, METAL COMPLEX COMPOUND, COLORED PHOTOSENSITIVE CURING COMPOSITION, COLOR FILTER, AND PRODUCTION

(75) Inventors: Yuki Mizukawa, Kanagawa (JP); Ryoji Goto, Kanagawa (JP); Hideki Takakuwa, Shizuoka-ken (JP); Masashi Ogiyama, Kanagawa (JP); Toru Fujimori, Shizuoka-ken (JP)

(73) Assignee: FUJIFILM Corporation, Tokyo (JP)

( * ) Notice: Subject to any disclaimer, the term of this patent is extended or adjusted under 35 U.S.C. 154(b) by 78 days.

This patent is subject to a terminal disclaimer.

(21) Appl. No.: 13/478,210

(22) Filed: May 23, 2012

(65) Prior Publication Data
US 2012/0238752 A1    Sep. 20, 2012

Related U.S. Application Data

(62) Division of application No. 11/905,028, filed on Sep. 27, 2007, now Pat. No. 8,197,994.

(30) Foreign Application Priority Data

Sep. 27, 2006 (JP) .................. 2006-263580
Apr. 26, 2007 (JP) .................. 2007-117651

(51) Int. Cl.
*G02B 5/20* (2006.01)
(52) U.S. Cl.
USPC ........................................ 548/402
(58) Field of Classification Search
None
See application file for complete search history.

(56) References Cited

U.S. PATENT DOCUMENTS

| 5,498,641 | A | 3/1996 | Urano et al. | |
|---|---|---|---|---|
| 8,334,085 | B2 * | 12/2012 | Mizukawa et al. | 430/7 |
| 2006/0051685 | A1 | 3/2006 | Fujimori et al. | |

FOREIGN PATENT DOCUMENTS

| JP | 6-75375 A | 3/1994 |
|---|---|---|
| JP | 11315268 | 11/1999 |
| JP | 2000-275830 A | 10/2000 |
| JP | 3279035 B2 | 2/2002 |
| JP | 2003-57436 A | 2/2003 |
| JP | 2005-077953 A | 3/2005 |
| JP | 2006-79011 A | 3/2006 |
| JP | 2007-094181 A | 4/2007 |
| JP | 2007-094187 A | 4/2007 |

OTHER PUBLICATIONS

Office Action dated Nov. 22, 2011 on Japanese Application No. 2007-252650.
Office Action dated Sep. 24, 2013 in U.S. Appl. No. 13/371,785.
Office Action dated Nov. 28, 2013 in Korean Patent Application No. 2007-97517.

* cited by examiner

*Primary Examiner* — John A. McPherson
(74) *Attorney, Agent, or Firm* — Sughrue Mion, PLLC

(57) ABSTRACT

Provided is a colored photosensitive curing composition useful for color filters in primary colors, including blue, green, and red, having a high molar absorption coefficient and allowing a reduction in film thickness and superior color purity and fastness. A colored photosensitive curing composition, comprising, as its colorant, a dipyrromethene-based metal complex compound obtained from a metal or metal compound and a dipyrromethene-based compound represented by the following Formula (I):

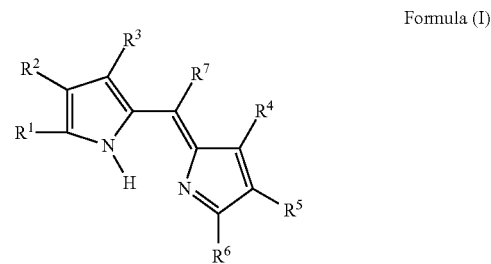

Formula (I)

wherein in Formula (I), $R^1$ to $R^6$ each independently represents a hydrogen atom or a substituent group; and $R^7$ represents a hydrogen or halogen atom, or an alkyl, aryl or heterocyclic group.

2 Claims, No Drawings

COMPOUND OR ITS TAUTOMER, METAL COMPLEX COMPOUND, COLORED PHOTOSENSITIVE CURING COMPOSITION, COLOR FILTER, AND PRODUCTION

CROSS-REFERENCE TO RELATED APPLICATIONS

This application is a divisional of U.S. application Ser. No. 11/905,028 filed Sep. 27, 2007, now U.S. Pat. No. 8,197,994 which claims priority under 35 USC 119 from Japanese Patent Application No. 2006-263580 and No. 2007-117651, the disclosures of which are incorporated by reference herein.

BACKGROUND OF THE INVENTION

1. Field of the Invention

The invention relates to a compound or its tautomer, a metal complex compound, and a colored photosensitive curing composition that are used favorably in production of a color filter for use in liquid crystal display elements and solid-state image sensing devices, a color filter, and a method for producing the same.

2. Description of the Related Art

A pigment dispersion method has been used as one of the methods for producing color filters for use in liquid crystal display elements and solid-state image sensing devices. The pigment dispersion method is a method of producing a color filter by photolithography, by using a colored radiation-sensitive composition containing a pigment dispersed in various kinds of photosensitive compositions. The method, which uses a pigment and provides a color filter resistant to light and heat and favorable in positioning accuracy because of patterning by photolithography, has been used widely as a favorable method in producing color filters for large-screen, high-resolution color displays.

In preparing a color filter by the pigment dispersion process, the radiation-sensitive composition is first coated on a substrate with a spin coater or roll coater and dried to form a coating film. Then, colored pixels are obtained by patterned-exposure and development of the coating film. The color filter can be prepared by repeating this operation a number of times corresponding to the number of hues.

Recently, in the color filter for solid state image sensing devices, even higher resolution has become desirable, but the conventional pigment dispersions have difficulties in further improving the resolution. Because of problems such as the generation of color irregularities due to coarse particles of the pigment, it is not suitable for uses which require fine patterns such as solid state image sensing devices.

Use of a dye as the colorant has been conventionally studied from the viewpoint of improvement in the resolution above (see, for example, Japanese Patent Application Laid-Open (JP-A) No. 6-75,375). However, such dye-containing curing compositions have the following additional problems:

(1) Dyes are generally lower in light stability and heat resistance than pigments.

(2) It is difficult to obtain a liquid curing composition having a desired spectrum with a common colorant, because such a colorant is less soluble in aqueous alkaline solution or organic solvent (hereinafter, suitably referred to as solvent).

(3) It is difficult to control the solubility (printing efficiency) of the cured area and the uncured area, because the dye used often interacts with other components in the curing composition.

(4) When the molar absorption coefficient (ε) of the dye used is low, the dye needs to be added in a larger amount and thus, the amounts of the other components in the curing composition such as polymerizable compound (monomer), binder, and photopolymerization initiator must be reduced, which leads to deterioration in the curing efficiency of the composition, the heat resistance after curing, and the developing efficiency of the (non) cured area.

Due to these problems, it has been difficult to form colored patterns that are detailed and have a thin film in high-resolution color filters. Unlike those used in the production of semiconductors, it is necessary to use a thin film of 1 μm or less in thickness for the production of color filters for solid-state image sensing devices. It is thus necessary to add a colorant to the curing composition in a larger amount for obtaining a desired absorption, leading to the problems described above.

Hereinafter, conventional technology concerning high-fastness dye will be described. Generally, all colorants used in various applications preferably have the following properties: light absorption properties favorable for color reproduction, favorable levels of stability, such as good heat resistance, light stability, and moisture resistance, under the environment in which it is used, a molar absorption coefficient large enough to allow reduction in film thickness, and others.

For example, dipyrromethene-based metal complexes are known to be used as a functional compound in various applications and also as a sensitizer for the radical polymerization initiator in visible light-sensitive photopolymerization compositions (see, e.g., Japanese Patent Nos. 3,279,035 and 3,324,279, and JP-A Nos. 11-352,685, 11-352,686, 2000-19, 729, 2000-19,738 and JP-A No. 2002-236,360). They are also known to be used, not as a colorant for red, green, or blue pixels in liquid crystal displays and electronic displays, but as a colorant for filters, for eliminating undesired emissions from, for example, plasma emission devices and liquid crystal displays (see, e.g., JP-A Nos. 2003-57,436, 2005-77,953, 2006-651,121, 2006-79,011 and 2006-79,012).

SUMMARY OF THE INVENTION

The present invention has been made in view of the above circumstances and provides a compound or its tautomer, a metal complex compound, a colored photosensitive curing composition, a color filter used the composition, and its production.

A first aspect of the present invention provides a colored photosensitive curing composition, comprising, as a colorant, a dipyrromethene-based metal complex compound obtained from a metal or metal compound and a dipyrromethene-based compound represented by the following Formula (I):

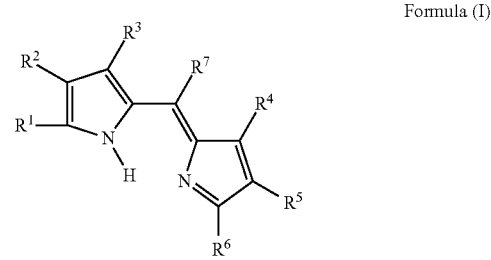

Formula (I)

wherein in Formula (I), $R^1$ to $R^6$ each independently represents a hydrogen atom or a substituent group; and $R^7$ represents a hydrogen or halogen atom, or an alkyl, aryl or heterocyclic group.

A second aspect of the present invention provides a compound represented by the following Formula (III) or a tautomer thereof:

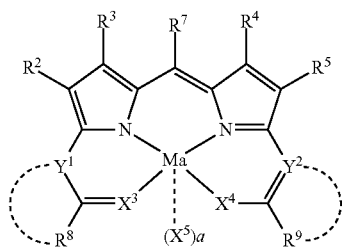

Formula (III)

wherein in Formula (III), $R^2$ to $R^5$ each independently represents a hydrogen atom or a substituent group; $R^7$ represents a hydrogen or halogen atom, or an alkyl, aryl or heterocyclic group; Ma represents a metal or metal compound; $X^3$ represents NR (wherein, R represents a hydrogen atom or an alkyl, alkenyl, aryl, heterocyclic, acyl, alkylsulfonyl, or arylsulfonyl group) or a nitrogen, oxygen or sulfur atom; $X^4$ represents NRa (wheren, Ra represents a hydrogen atom or an alkyl, alkenyl, aryl, heterocyclic, acyl, alkylsulfonyl, or arylsulfonyl group) or an oxygen or sulfur atom; $Y^1$ represents NRc (wherein, Rc represents a hydrogen atom or an alkyl, alkenyl, aryl, heterocyclic, acyl, alkylsulfonyl, or arylsulfonyl group) or a nitrogen or carbon atom; $Y^2$ represents a nitrogen or carbon atom; and $R^8$ and $R^9$ each independently represents an alkyl, alkenyl, aryl, heterocyclic, alkoxy, aryloxy, alkylamino, arylamino, or heterocyclic amino group; $R^8$ and $Y^1$ may bind to each other to form a five-, six-, or seven-membered ring; $R^9$ and $Y^2$ may bind to each other to form a five-, six-, or seven-membered ring; $X^5$ represents a group that can bind to Ma; and a is 0, 1, or 2.

A third aspect of the present invention provides a compound represented by the following Formula (IV) or a tautomer thereof.

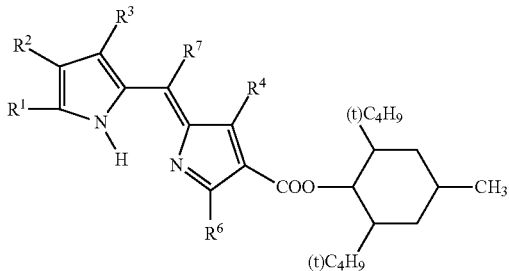

Formula (IV)

wherein in Formula (IV), $R^1$ to $R^4$, and $R^6$ each independently represents a hydrogen atom or a substituent group; and $R^7$ represents a hydrogen or halogen atom, or an alkyl, aryl or heterocyclic group.

A fourth aspect of the present invention provides a metal complex compound, obtained from a metal or metal compound and a compound represented by the following Formula (IV):

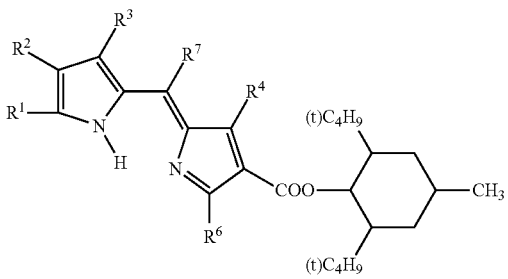

Formula (IV)

wherein in Formula (IV), $R^1$ to $R^4$, and $R^6$ each independently represents a hydrogen atom or a substituent group; and $R^7$ represents a hydrogen or halogen atom, or an alkyl, aryl or heterocyclic group.

DETAILED DESCRIPTION OF THE INVENTION

The invention provides a compound useful for color filters in primary colors, blue, green, and red, having a high absorption coefficient allowing reduction in thickness thereof that are superior in color purity and fastness, and a tautomer thereof, a metal complex compound and a colored photosensitive curing composition containing the metal complex compound.

The invention also provides a blue-colored photosensitive curing composition having a high absorption coefficient allowing the thickness thereof that is superior in blue color purity and fastness.

The invention also provides a color filter prepared by using the colored photosensitive curing composition that allows reduction in the thickness thereof and is superior in color purity and fastness, and a method of producing the same.

After intensive studies by the inventors on various colorants in detail, the invention was made, on the basis of the finding that a particular dipyrromethene-based metal complex compound has a color tone (hue) favorable as a colorant for color patterning and a high absorption coefficient and also has favorable fastness against heat and light.

Hereinafter, the colored photosensitive curing composition of the invention, the compound used in the composition, its tautomer, the metal complex compound, the color filter, and the method of producing the color in an aspect of the invention will be described in detail.

<<Colored Photosensitive Curing Composition>>

The colored photosensitive curing composition of the invention characteristically contains at least one dipyrromethene-based metal complex compound obtained from a dipyrromethene-based compound represented by the following Formula (I) (hereinafter, suitably referred to as "particular compound I") and a metal or metal compound (hereinafter, suitably referred to as "particular metal complex compound I") as its colorant.

In another preferable aspect, it characteristically contains at least one dipyrromethene-based metal complex compound obtained from a compound represented by the following Formula (IV) and a metal or metal compound (hereinafter, suitably referred to as "particular metal complex compound IV"). Particularly preferably, the term "photosensitive" means "ultraviolet sensitive".

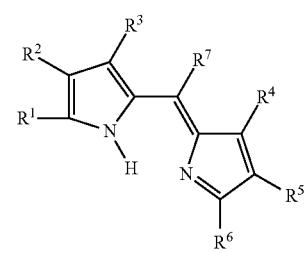

Formula (I)

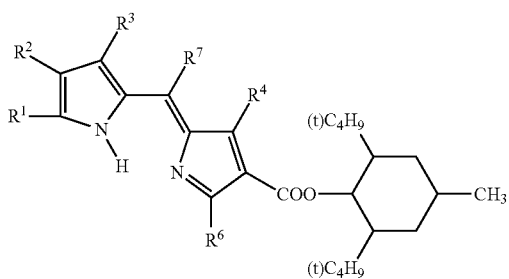

Formula (IV)

R¹ to R⁶ in Formula (I) and R¹ to R⁴ and R⁶ in Formula (IV) each independently represent a hydrogen atom or a substituent group. R⁷ represents a hydrogen atom, halogen atom, alkyl, aryl or hetero ring group.

Examples of the substituent groups of R¹ to R⁶ in Formula (I) and R¹ to R⁴, and R⁶ in Formula (IV) include halogen atoms (such as fluorine, chlorine, and bromine), alkyl groups (preferably straight-chain, branched-chain and cyclic alkyl groups having 1 to 48 carbon atoms, more preferably having 1 to 24 carbon atoms, such as methyl, ethyl, propyl, isopropyl, butyl, t-butyl, pentyl, hexyl, heptyl, octyl, 2-ethylhexyl, dodecyl, hexadecyl, cyclopropyl, cyclopentyl, cyclohexyl, 1-norbornyl, and 1-adamantyl), alkenyl groups (preferably alkenyl groups having 2 to 48 carbon atoms, more preferably having 2 to 18 carbon atoms, such as vinyl, allyl, and 3-buten-1-yl), aryl groups (preferably aryl groups having 6 to 48 carbon atoms, more preferably having 6 to 24 carbon atoms, such as phenyl and naphthyl), heterocyclic groups (preferably heterocyclic groups having 1 to 32 carbon atoms, more preferably having 1 to 18 carbon atoms, such as 2-thienyl, 4-pyridyl, 2-furyl, 2-pyrimidinyl, 1-pyridyl, 2-benzothiazolyl, 1-imidazolyl, 1-pyrazolyl, and benzotriazolyl-1-yl), silyl groups (preferably silyl groups having 3 to 38 carbon atoms, more preferably having 3 to 18 carbon atoms, such as trimethylsilyl, triethylsilyl, tributylsilyl, t-butyldimethylsilyl, and t-hexyldimethylsilyl), a hydroxyl group, a cyano group, a nitro group, alkoxy groups (preferably alkoxy groups having 1 to 48 carbon atoms, more preferably having 1 to 24 carbon atoms, such as methoxy, ethoxy, 1-butoxy, 2-butoxy, isopropoxy, t-butoxy, and dodecyloxy), cycloalkyloxy groups (such as cyclopentyloxy and cyclohexyloxy), aryloxy groups (preferably aryloxy groups having 6 to 48 carbon atoms, more preferably having 6 to 24 carbon atoms, such as phenoxy and 1-naphthoxy), heterocyclic oxy groups (preferably heterocyclic oxy groups having 1 to 32 carbon atoms, more preferably having 1 to 18 carbon atoms, such as 1-phenyltetrazole-5-oxy and 2-tetrahydropyranyloxy), silyloxy groups (preferably silyloxy groups having 1 to 32 carbon atoms, more preferably having 1 to 18 carbon atoms, such as trimethylsilyloxy, t-butyldimethylsilyloxy, and diphenylmethylsilyloxy), acyloxy groups (preferably acyloxy groups having 2 to 48 carbon atoms, more preferably having 2 to 24 carbon atoms, such as acetoxy, pivaloyloxy, benzoyloxy, and dodecanoyloxy), alkoxycarbonyloxy groups (preferably alkoxycarbonyloxy groups having 2 to 48 carbon atoms, more preferably having 2 to 24 carbon atoms, such as ethoxycarbonyloxy and t-butoxycarbonyloxy), cycloalkyloxycarbonyloxy groups (such as cyclohexyloxycarbonyloxy), aryloxycarbonyloxy groups (preferably aryloxycarbonyloxy groups having 7 to 32 carbon atoms, more preferably having 7 to 24 carbon atoms, such as phenoxycarbonyloxy), carbamoyloxy groups (preferably carbamoyloxy groups having 1 to 48 carbon atoms, more preferably having 1 to 24 carbon atoms, such as N,N-dimethylcarbamoyloxy, N-butylcarbamoyloxy, N-pheylcarbamoyloxy, and N-ethyl-N-pheylcarbamoyloxy), sulfamoyloxy groups (preferably sulfamoyloxy groups having 1 to 32 carbon atoms, more preferably having 1 to 24 carbon atoms, such as N,N-diethylsulfamoyloxy and N-propylsulfamoyloxy), alkylsulfonyloxy groups (preferably alkylsulfonyloxy groups having 1 to 38 carbon atoms, more preferably having 1 to 24 carbon atoms, such as methylsulfonyloxy, hexadecylsulfonyloxy, and cyclohexylsulfonyloxy), arylsulfonyloxy groups (preferably arylsulfonyloxy groups having 6 to 32 carbon atoms, more preferably having 6 to 24 carbon atoms, such as phenylsulfonyloxy), acyl groups (preferably acyl groups having 1 to 48 carbon atoms, more preferably having 1 to 24 carbon atoms, such as formyl, acetyl, pivaloyl, benzoyl, tetradecanoyl, and cyclohaxanoyl), alkoxycarbonyl groups (preferably alkoxycarbonyl groups having 2 to 48 carbon atoms, more preferably having 2 to 24 carbon atoms, such as methoxycarbonyl, ethoxycarbonyl, octadecyloxycarbonyl, cyclohexyloxycarbonyl, and 2,6-di-tert-butyl-4-methylcyclohexyloxycarbonyl), aryloxycarbonyl groups (preferably aryloxycarbonyl groups having 7 to 32 carbon atoms, more preferably having 7 to 24 carbon atoms, such as phenoxycarbonyl), carbamoyl groups (preferably carbamoyl groups having 1 to 48 carbon atoms, more preferably having 1 to 24 carbon atoms, such as carbamoyl, N,N-diethylcarbamoyl, N-ethyl-N-octylcarbamoyl, N,N-dibutylcarbamoyl, N-propylcarbamoyl, N-pheylcarbamoyl, N-methyl-N-pheylcarbamoyl, and N,N-dicyclohexylcarbamoyl), amino groups (preferably amino groups having 32 or fewer carbon atoms, more preferably having 24 or fewer carbon atoms, such as amino, methylamino, N,N-dibutylamino, tetradecylamino, 2-ethylhexylamino, and cyclohexylamino), anilino groups (preferably anilino groups having 6 to 32 carbon atoms, more preferably 6 to 24, such as anilino and N-methyl anilino), heterocyclic amino groups (preferably heterocyclic amino groups having 1 to 32 carbon atoms, more preferably 1 to 18 carbon atoms, such as 4-pyridylamino), carbonamido groups (preferably carbonamido groups having 2 to 48 carbon atoms, more preferably 2 to 24, such as acetamido, benzamido, tetradecaneamido, pivaloylamido, and cyclohexaneamido), ureido group (preferably ureido groups having 1 to 32 carbon atoms, more preferably having 1 to 24 carbon atoms, such as ureido, N,N-dimethylureido, and N-phenylureido), imide groups (preferably imide groups having 36 or fewer carbon atoms, more preferably having 24 or fewer carbon atoms, such as N-succinimide and N-phthalimide), alkoxycarbonylamino groups (preferably alkoxycarbonylamino groups having 2 to 48 carbon atoms, more preferably having 2 to 24 carbon atoms, such as methoxycarbonylamino, ethoxycarbonylamino, t-butoxycarbonylamino, octadecyloxycarbonylamino, and cyclohexyloxycarbonylamino), aryloxycarbonylamino groups (preferably aryloxycarbonylamino group having 7 to 32 carbon atoms, more preferably having 7 to 24 carbon atoms, such as phenoxycarbonylamino), sulfonamido groups (preferably sulfonamido groups having 1 to 48 carbon atoms, more preferably having 1 to 24 carbon atoms, such as methanesulfonamido, butanesulfonamido, benzenesulfonamido, hexadecanesulfonamido, and cyclohexanesulfonamido), sulfamoylamino groups (preferably sulfamoylamino groups having 1 to 48 carbon atoms, more preferably having 1 to 24 carbon atoms, such as N,N-dipropylsulfamoylamino and N-ethyl-N-dodecylsulfamoylamino), azo groups (preferably azo groups having 1 to 32 carbon atoms, more preferably having 1 to 24 carbon atoms, such as phenylazo and 3-pyrazolylazo), alkylthio groups (preferably alkylthio groups having 1 to 48 carbon atoms, more preferably having 1 to 24 carbon atoms, such as methylthio, ethylthio, octylthio, and cyclohexylthio), arylthio groups (preferably arylthio groups having 6 to 48 carbon atoms, more preferably having 6 to 24 carbon atoms, such as phenylthio), heterocyclic thio groups (preferably heterocyclic thio groups having 1 to 32 carbon atoms, more preferably having 1-18 carbon atoms, such as 2-benzothiazolylthio, 2-pyridylthio, and 1-phenyltetrazolylthio), alkylsulfinyl groups (preferably alkylsulfinyl groups having 1 to 32 carbon atoms, more preferably having 1 to 24 carbon atoms, such as dodecanesulfinyl), arylsulfinyl groups (preferably arylsulfinyl groups having 6 to 32 carbon atoms, more preferably having 6 to 24 carbon atoms, such as phenylsulfinyl), alkylsulfonyl groups (preferably alkylsulfonyl groups having 1 to 48 carbon atoms, more preferably having 1 to 24 carbon atoms, such as methylsulfonyl, ethylsulfonyl, propylsulfonyl, butylsulfonyl, isopropylsulfonyl, 2-ethylhexylsulfonyl, hexadecylsulfonyl, octylsulfonyl, and cyclohexylsulfonyl), arylsulfonyl groups (preferably arylsulfonyl groups having 6 to 48 carbon atoms, more preferably having 6 to 24 carbon atoms, such as phenylsulfonyl and 1-naphthyl sulfonyl), sulfamoyl groups (preferably sulfamoyl groups having 32 or fewer carbon atoms, more preferably having 24 or fewer carbon atoms, such as sulfamoyl, N,N-dipropylsulfamoyl, N-ethyl-N-dodecylsulfamoyl, N-ethyl-N-phenylsulfamoyl, and N-cyclohexylsulfamoyl), a sulfo group, sulfonyl groups (preferably sulfonyl groups having 1 to 32 carbon atoms, more preferably having 1 to 24 carbon atoms, such as phenoxyphosphonyl, octyloxyphosphonyl, and phenylsulfonyl), and phosphinoylamino groups (preferably phosphinoylamino groups having 1 to 32 carbon atoms, more preferably having 1 to 24 carbon atoms, such as diethoxyphosphinoylamino and dioctyloxyphosphinoylamino).

When one of the substituent groups of $R^1$ to $R^6$ in Formula (I) and $R^1$ to $R^4$, and $R^6$ in Formula (IV) is a group that may be additionally substituted, the group may have one or more substituent groups described for $R^1$ to $R^6$; and when two or more substituent groups are contained, the substituent groups may be the same as or different from each other.

$R^1$ and $R^2$, $R^2$ and $R^3$, $R^4$ and $R^5$, or/and $R^5$ and $R^6$ in Formula (I) and $R^1$ and $R^2$ or/and $R^2$ and $R^3$ in Formula (IV) each independently may bind to each other to form a five-, six-, or seven-membered saturated or unsaturated ring. When the five-, six-, or seven-membered ring formed is a group that may be substituted, it may be substituted with one or more substituent groups described for $R^1$ to $R^6$ above, and when two or more substituent groups are substituted, the substituent groups may be the same as or different from each other.

$R^7$ in Formulae (I) and (IV) represents a hydrogen or halogen atom or an alkyl, aryl or heterocyclic, and is the same as the halogen atom of the alkyl, aryl and heterocyclic group described above as the substituent group for $R^1$ to $R^6$, and the preferable examples thereof are also the same.

When the alkyl, aryl or heterocyclic group of $R^7$ is a group that may be substituted additionally, it may be substituted with one or more substituent groups described above as that for $R^1$ to $R^6$, and when two or more substituent groups are substituted, the substituent groups may be the same as or different from each other.

<Metal or Metal Compound>

A metal or metal compound is needed, in addition to the particular compound, for obtaining the particular metal complex compounds I and IV contained in the colored photosensitive curing composition of the invention.

The metal or metal compound forming the particular metal complex compound I or IV together with the particular compound above is not particularly limited, if it is a metal or metal compound forming a complex, and examples thereof include bivalent metal atoms, bivalent metal oxides, bivalent metal hydroxides, and bivalent metal chlorides. Examples of the metals include Zn, Mg, Si, Sn, Rh, Pt, Pd, Mo, Mn, Pb, Cu, Ni, Co, and Fe; and other examples thereof include metal chlorides such as AlCl, InCl, FeCl, $TiCl_2$, $SnCl_2$, $SiCl_2$, $GeCl_2$, and the like; metal oxides such as TiO and VO; and metal hydroxides such as $Si(OH)_2$. Among them, Fe, Zn, Mg, Si, Pt, Pd, Mo, Mn, Cu, Ni, Co, TiO, and VO are preferable; Zn, Mg, Si, Pt, Pd, Cu, Ni, Co, and VO are more preferable; and Zn is most preferable, for example, from the viewpoints of the stability, spectroscopic properties, heat resistance, light stability, and production efficiency of the complex.

Hereinafter, preferable examples of the compounds represented by Formulae (I) and (IV) will be described.

Favorably in Formulae (I) and (IV), $R^1$ and $R^6$ each independently represent a hydrogen atom or an alkyl, alkenyl, aryl, heterocyclic, silyl, hydroxyl, cyano, alkoxy, aryloxy, heterocyclic oxy, acyl, alkoxycarbonyl, carbamoyl, amino, anilino, heterocyclic amino, carbonamido, ureido, imido, alkoxycarbonylamino, aryloxycarbonylamino, sulfonamido, azo, alkylthio, arylthio, heterocyclic thio, alkylsulfonyl, arylsulfonyl, or phosphinoylamino group; $R^2$ and $R^5$ each independently represent a hydrogen or halogen atom or an alkyl, alkenyl, aryl, heterocyclic, hydroxyl, cyano, nitro, alkoxy, aryloxy, heterocyclic oxy, acyl, alkoxycarbonyl, aryloxycarbonyl, carbamoyl, imido, alkoxycarbonylamino, sulfonamido, azo, alkylthio, arylthio, heterocyclic thio, alkylsulfonyl, arylsulfonyl, or sulfamoyl group; $R^3$ and $R^4$ each independently represent a hydrogen or halogen atom or an alkyl, alkenyl, aryl, heterocyclic, silyl, hydroxyl, cyano, alkoxy, aryloxy, heterocyclic oxy, acyl, alkoxycarbonyl, carbamoyl, anilino, carbonamido, ureido, imido, alkoxycarbonylamino, sulfonamido, azo, alkylthio, arylthio, heterocyclic thio, alkylsulfonyl, arylsulfonyl, sulfamoyl, or phosphinoylamino group; $R^7$ represents a hydrogen atom or a halogen atom or an alkyl, aryl or heterocyclic group; and the metal or metal compound represents Zn, Mg, Si, Pt, Pd, Mo, Mn, Cu, Ni, Co, TiO, or VO.

More preferably in Formulae (I) and (IV), $R^1$ and $R^6$ each independently represent a hydrogen atom or an alkyl, alkenyl, aryl, heterocyclic, cyano, acyl, alkoxycarbonyl, carbamoyl, amino, heterocyclic amino, carbonamido, ureido, imido, alkoxycarbonylamino, aryloxycarbonylamino, sulfonamido, azo, alkylsulfonyl, arylsulfonyl, or phosphinoylamino group; $R^2$ and $R^5$ each independently represent an alkyl, alkenyl, aryl, heterocyclic, cyano, nitro, acyl, alkoxycarbonyl, aryloxycarbonyl, carbamoyl, imide, alkylsulfonyl, arylsulfonyl, or sulfamoyl group; $R^3$ and $R^4$ each independently represent a hydrogen atom or an alkyl, alkenyl, aryl, heterocyclic, cyano, acyl, alkoxycarbonyl, carbamoyl, carbonamido, ureido, imido, alkoxycarbonylamino, sulfonamido, alkylthio, arylthio, heterocyclic thio, alkylsulfonyl, arylsulfonyl, or sulfamoyl group; $R^7$ represents a hydrogen or halogen atom or an alkyl, aryl or heterocyclic group; and the metal or metal compound represents Zn, Mg, Si, Pt, Pd, Cu, Ni, Co, or VO.

Particularly preferably in Formulae (I) and (IV), $R^1$, and $R^6$ each independently represent a hydrogen atom or an alkyl, aryl, heterocyclic, amino, heterocyclic amino, carbonamido, ureido, imido, alkoxycarbonylamino, sulfonamido, azo, alkylsulfonyl, arylsulfonyl, or phosphinoylamino group; $R^2$ and $R^5$ each independently represent an alkyl, aryl, heterocyclic, cyano, acyl, alkoxycarbonyl, carbamoyl, alkylsulfonyl, or arylsulfonyl group; $R^3$ and $R^4$ each independently represent a hydrogen atom or an alkyl, aryl or heterocyclic group; $R^7$ represents a hydrogen atom or an alkyl, aryl or heterocyclic group; and the metal or metal compound represents Zn, Cu, Co, or VO.

When $R^1$ and $R^2$, $R^2$ and $R^3$, $R^4$ and $R^5$, or/and $R^5$ and $R^6$ in Formula (I) and $R^1$ and $R^2$, or/and $R^2$ and $R^3$ in Formula (IV) each independently bind to each other to form a five-, six-, or seven-membered saturated or unsaturated ring having no substituent group, examples of the five-, six-, or seven-membered saturated or unsaturated rings having no substituent group include pyrrole, furan, thiophene, pyrazole, imidazole, triazole, oxazole, thiazole, pyrrolidine, piperidine, cyclopentene, cyclohexene, benzene, pyridine, pyrazine, and pyridazine rings, and benzene and pyridine rings are preferable.

Examples of the substituent groups for the rings, when present, include those described above for $R^1$ to $R^6$, and favorable substituent groups are also the same as those for $R^1$ to $R^6$.

The compound represented by Formula (IV) may be a tautomer thereof.

<Compound Represented by Formula (II-1)>

Among the particular metal complex compounds I and IV above, the following compounds represented by Formula (II-1) (hereinafter, suitably referred to as "particular metal complex compounds II-1") are preferable.

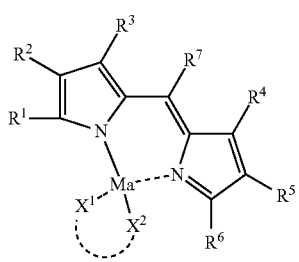

Formula (II-1)

In Formula (II-1), $R^1$ to $R^6$ each independently represent a hydrogen atom or a substituent group. $R^7$ represents a hydrogen or halogen atom or an alkyl, aryl or heterocyclic group. Ma represents a metal or metal compound; $X^2$ represents a group needed for neutralization of the electric charge of Ma; and $X^1$ represents a group that can bind to Ma. $X^1$ and $X^2$ may bind to each other to form a five-, six-, or seven-membered ring.

$R^1$ to $R^6$ in Formula (II-1) are the same as $R^1$ to $R^6$, and the preferable examples thereof are also the same.

Ma in Formula (II-1) represents a metal or metal compound; it is the same metal or metal compound as that described in the particular metal complex compound I; and the preferable examples thereof are also the same.

$R^7$ in Formula (II-1) is the same as $R^7$ in Formula (I), and the preferable examples thereof are also the same.

$X^1$ in Formula (II-1) may be any atom that can bind to the metal atom Ma, and examples thereof include water, alcohols (such as methanol, ethanol, and propanol), and the compounds described, for example, in Genichi Sakaguchi and Keihei Ueno, "Metal Chelates" [1], (Nankodo, 1995), ibid., [2] (1996), and ibid., [3] (1997) and others.

$X^2$ in Formula (II-1) represents a group needed for neutralization of the electric charge of Ma, such as a halogen atom or a hydroxyl, carboxylate, phosphate, or sulfate group.

$X^1$ and $X^2$ in Formula (II-1) may bind to each other to form a five-, six-, or seven-membered ring with Ma. The five-, six-, or seven-membered ring may be a saturated or unsaturated ring. The five-, six- or seven-membered ring may contain only carbon atoms or may be a heterocyclic ring having at least one atom selected from nitrogen, oxygen and sulfur atoms.

<Compound Represented by Formula (II-2)>

In the particular metal complex compound II-1, a compound represented by the following Formula (II-2) (hereinafter, suitably referred to as "particular metal complex compound II-2") may be used as needed.

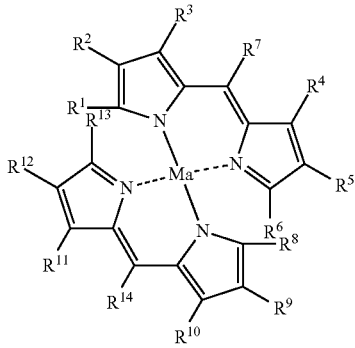

Formula (II-2)

In Formula (II-2), $R^1$ to $R^6$ and $R^8$ to $R^{13}$ each independently represent a hydrogen atom or a substituent group. $R^7$ and $R^{14}$ each independently represent a hydrogen or halogen atom or an alkyl, aryl or heterocyclic group. Ma represents a metal or metal compound.

$R^1$ to $R^6$ in Formula (II-2) are the same as $R^1$ to $R^6$ in Formula (I), and the preferable aspects thereof are also the same.

The substituent groups represented by $R^6$ to $R^{13}$ in Formula (II-2) are the same as $R^1$ to $R^6$ in the compound represented by Formula (I), and the preferable examples thereof are also the same. When the substituent group represented by $R^8$ to $R^{13}$ in the compound represented by Formula (II-2) is a group that may be substituted additionally, the group may be substituted with one or more substituent groups described for $R^1$ to $R^6$ in the compound represented by Formula (I), and, when two or more substituent groups are substituted, the substituent groups may be the same as or different from each other.

$R^7$ in Formula (II-2) is the same as $R^7$ in Formula (I), and the preferable aspects thereof are also the same.

$R^{14}$ in Formula (II-2) represents a hydrogen or halogen atom or an alkyl, aryl or heterocyclic group; and the favorable range of $R^{14}$ is the same as that of the $R^7$ above. When $R^{14}$ is a group that may be substituted additionally, it may be substituted with the substituent group described for $R^1$ to $R^6$ in the compound represented by Formula (I), and when two or more substituent groups are substituted, the substituent groups may be the same as or different from each other.

In Formula (II-2), Ma represents a metal or metal compound; it is the same as the metal or metal compound described for the particular metal complex compound I; and the preferable examples thereof are also the same.

$R^8$ and $R^9$, $R^9$ and $R^{10}$, $R^{11}$ and $R^{12}$, or/and $R^{12}$ and $R^{13}$ in Formula (II-2) may bind to each other forming a five-, six-, or seven-membered saturated or unsaturated ring; these groups are the same as $R^1$ and $R^2$, $R^2$ and $R^3$, $R^4$ and $R^5$, or/and $R^5$ and $R^6$ in the compound represented by Formula (I); and the preferable examples thereof are also the same.

<Compound Represented by Formula (III)>

Among the particular metal complex compounds I and IV, the compounds represented by the following Formula (III) (hereinafter, suitably referred to as "particular metal complex compounds III") are preferable.

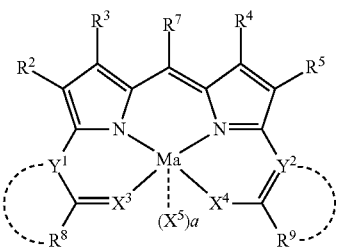

Formula (III)

In Formula (III), $R^2$ to $R^5$ each independently represent a hydrogen atom or a substituent group. $R^7$ represents a hydrogen or halogen atom or an alkyl, aryl or heterocyclic group. Ma represents a metal or metal compound; $X^3$ represents NR (wherein, R represents a hydrogen atom or an alkyl, alkenyl, aryl, heterocyclic, acyl, alkylsulfonyl, or arylsulfonyl group) or a nitrogen, oxygen, or sulfur atom; $X^4$ represents NRa (wherein, Ra represents a hydrogen atom or an alkyl, alkenyl, aryl, heterocyclic, acyl, alkylsulfonyl, or arylsulfonyl group) or an oxygen or sulfur atom; $Y^1$ represents NRc (wherein, Rc represents a hydrogen atom or an alkyl, alkenyl, aryl, heterocyclic, acyl, alkylsulfonyl, or arylsulfonyl group) or a nitrogen or carbon atom; $Y^2$ represents a nitrogen or carbon atom; and $R^8$ and $R^9$ each independently represent an alkyl, alkenyl, aryl, heterocyclic, alkoxy, aryloxy, alkylamino, arylamino, or heterocyclic amino group. $R^8$ and $Y^1$ may bind to each other to form a five-, six-, or seven-membered ring; and $R^9$ and $Y^2$ may bind to each other to form a five-, six-, or seven-membered ring. $X^5$ represents a group that can bind to Ma; and a is 0, 1, or 2.

$R^2$ to $R^5$ and $R^7$ in Formula (III) are the same as $R^1$ to $R^6$ and $R^7$ in Formula (I), and the preferable aspects thereof are also the same.

Ma in Formula (III) represents a metal or metal compound; it is the same as the metal or metal compound described for the particular metal complex compound I; and and the preferable examples thereof are also the same.

In Formula (III), $R^8$ and $R^9$ each independently represent an alkyl group (preferably a straight-chain, branched-chain or cyclic alkyl group having 1 to 36 carbon atoms, more preferably 1 to 12 carbon atoms, such as methyl, ethyl, propyl, isopropyl, butyl, isobutyl, t-butyl, hexyl, 2-ethylhexyl, dodecyl, cyclopropyl, cyclopentyl, cyclohexyl, or 1-adamantyl), an alkenyl group (preferably an alkenyl group having 2 to 24 carbon atoms, more preferably 2 to 12 carbon atoms, such as vinyl, allyl, or 3-buten-1-yl), an aryl group (preferably an aryl group having 6 to 36 carbon atoms, more preferably 6 to 18 carbon atoms, such as phenyl or naphthyl), a heterocyclic group (preferably a heterocyclic group having 1 to 24 carbon atoms, more preferably 1 to 12 carbon atoms, such as 2-thienyl, 4-pyridyl, 2-furyl, 2-pyrimidinyl, 1-pyridyl, 2-benzothiazolyl, 1-imidazolyl, 1-pyrazolyl, or benzotriazolyl-1-yl), an alkoxy group (preferably an alkoxy group having 1 to 36 carbon atoms, more preferably 1 to 18 carbon atoms, such as methoxy, ethoxy, propyloxy, butoxy, hexyloxy, 2-ethylhexyloxy, dodecyloxy, or cyclohexyloxy), an aryloxy (preferably an aryloxy group having 6 to 24 carbon atoms, more preferably 1 to 18 carbon atoms, such as phenoxy or naphthyloxy), an alkylamino group (preferably an alkylamino group having 1 to 36 carbon atoms, more preferably 1 to 18 carbon atoms, such as methylamino, ethylamino, propylamino, butylamino, hexylamino, 2-ethylhexylamino, isopropylamino, t-butylamino, t-octylamino, cyclohexylamino, N,N-diethyl amino, N,N-dipropyl amino, N,N-dibutylamino, or N-methyl-N-ethylamino), an arylamino group (preferably an arylamino group having 6 to 36 carbon atoms, more preferably 6 to 18 carbon atoms, such as phenylamino, naphthylamino, N,N-diphenylamino, or N-ethyl-N-phenylamino), or a heterocyclic amino group (preferably a heterocyclic amino group having 1 to 24 carbon atoms, more preferably 1 to 12 carbon atoms, such as 2-aminopyrrole, 3-aminopyrazole, 2-aminopyridine, or 3-aminopyridine).

In Formula (III), when the alkyl, alkenyl, aryl, heterocyclic, alkoxy, aryloxy, alkylamino, arylamino, or heterocyclic amino group of $R^8$ or $R^9$ is a group that may be substituted additionally, it may be substituted with one or more substituent groups described for $R^1$ to $R^6$ above, and when two or more substituent groups are substituted, the substituent groups may be the same as or different from each other.

In Formula (III), $X^3$ represents NR or a nitrogen, oxygen or sulfur atom; $X^4$ represents NRa or an oxygen or sulfur atom; and R or Ra each independently represents a hydrogen atom, an alkyl group (preferably a straight-chain, branched-chain or cyclic alkyl group having 1 to 36 carbon atoms, more preferably 1 to 12 carbon atoms, such as methyl, ethyl, propyl, isopropyl, butyl, isobutyl, t-butyl, hexyl, 2-ethylhexyl, dodecyl, cyclopropyl, cyclopentyl, cyclohexyl, or 1-adamantyl), an alkenyl group (preferably an alkenyl group having 2 to 24 carbon atoms, more preferably 2 to 12 carbon atoms, such as vinyl, allyl, or 3-buten-1-yl), an aryl group (preferably an aryl group having 6 to 36 carbon atoms, more preferably 6 to 18 carbon atoms, such as phenyl or naphthyl), a heterocyclic group (preferably a heterocyclic group having 1 to 24 carbon atoms, more preferably 1 to 12 carbon atoms, such as 2-thienyl, 4-pyridyl, 2-furyl, 2-pyrimidinyl, 1-pyridyl, 2-benzothiazolyl, 1-imidazolyl, 1-pyrazolyl, or benzotriazolyl-1-yl), an acyl group (preferably an acyl group having 1 to 24 carbon atoms, more preferably 2 to 18 carbon atoms, such as acetyl, pivaloyl, 2-ethylhexyl, benzoyl, or cyclohaxanoyl), an alkylsulfonyl group (preferably an alkylsulfonyl group having 1 to 24 carbon atoms, more preferably 1 to 18 carbon atoms, such as methylsulfonyl, ethylsulfonyl, isopropylsulfonyl, or cyclohexylsulfonyl), or an arylsulfonyl group (preferably an arylsulfonyl group having 6 to 24 carbon atoms, more preferably 6 to 18 carbon atoms, such as phenylsulfonyl or naphthylsulfonyl).

The alkyl, alkenyl, aryl, heterocyclic, acyl, alkylsulfonyl, or arylsulfonyl group of R or Ra may be substituted additionally with one or more substituent groups described for $R^1$ to $R^6$ above, and when it is substituted with multiple substituent groups, the substituent groups may be the same as or different from each other.

In Formula (III), $Y^1$ represents NRc or a nitrogen or carbon atom; $Y^2$ represents a nitrogen or carbon atom; and Rc is the same as R of $X^3$.

In Formula (III), $R^8$ and $Y^1$ may bind to each other to form, with carbon atoms, a five-membered ring (such as cyclopentane, pyrrolidine, tetrahydrofuran, dioxolane, tetrahydrothiophene, pyrrole, furan, thiophene, indole, benzofuran, or benzothiophene), a six-membered ring (such as cyclohexane, piperidine, piperazine, morpholine, tetrahydropyran, dioxane, pentamethylene sulfide, dithiane, benzene, piperidine, piperazine, pyridazine, quinoline, or quinazoline), or a seven-membered ring (such as cycloheptane or hexamethylene imine).

In Formula (III), $R^9$ and $Y^2$ may bind to each other to form a five-, six-, or seven-membered ring with carbon atoms. The five-, six-, or seven-membered ring is, for example, the ring above formed by $R^8$, $Y^1$ and carbon atoms wherein one bond is replaced with a double bond.

In Formula (III), when the five-, six-, or seven-membered ring formed by binding of $R^8$ and $Y^1$ or $R^9$ and $Y^2$ is a ring that may be substituted additionally, it may be substituted with one or more substituent groups described above for $R^2$ to $R^5$, and when two or more substituent groups are substituted, the substituent groups may be the same as or different from each other.

In Formula (III), $X^5$ represents a group that can bind to Ma; and it is a group similar to that of $X^1$ in Formula (II-1).

a is 0, 1 or 2.

In a preferable aspect of the compound represented by Formula (III), $R^2$ to $R^5$, $R^7$, and Ma are respectively the groups described favorably for the compound represented by Formula (I); $X^3$ represents NR (wherein, R represents a hydrogen atom or an alkyl group) or a nitrogen or oxygen atom; $X^4$ represents NRa (wherein, Ra represents a hydrogen atom or an alkyl group) or an oxygen atom; $Y^1$ represents NRc (wherein, Rc represents a hydrogen atom or an alkyl group) or a nitrogen or carbon atom; $Y^2$ represents a nitrogen or carbon atom; $X^5$ represents a group binding via an oxygen atom; $R^8$ and $R^9$ each independently represents an alkyl, aryl, heterocyclic, alkoxy, or alkylamino group; and $R^8$ and $Y^1$ may bind to each other to form a five-membered or six-membered ring, or $R^9$ and $Y^2$ may bind to each other to form a five- or six-membered ring; and a is 0 or 1.

In a still more favorable aspect of the compound represented by Formula (III), $R^2$ to $R^5$, $R^7$, and Ma are respectively the groups described favorably for the compound represented by Formula (I); each of $X^3$ and $X^4$ is an oxygen atom; $Y^1$ is NH; $Y^2$ is a nitrogen atom; $X^5$ represents a group binding via an oxygen atom; $R^8$ and $R^9$ each represent an alkyl, aryl, heterocyclic, alkoxy, or alkylamino group; $R^8$ and $Y^1$ may bind to each other to form a five- or six-membered ring, or $R^9$ and $Y^2$ may bind to each other to form a five- or six-membered ring; and a is 0 or 1.

The molar absorption coefficient of the particular metal complex compounds I to IV in the invention is preferably higher, from the viewpoint of film thickness. The maximum absorption wavelength thereof λmax is preferably 520 to 580 nm, more preferably 530 to 570 nm, from the viewpoint of improvement in color purity. The maximum absorption wavelength and the molar absorption coefficient are determined by using a spectrophotometer UV-2400PC (manufactured by Shimadzu Corporation).

In the invention the melting point of the particular metal complex compound I is preferably not too high, from the viewpoint of solubility.

Specific examples of the particular metal complex compounds I in the invention (including particular metal complex compounds II-1, II-2, and IV) are shown below (exemplary compound Ia-3 to Ia-16, Ia-18 to Ia-83, IIa-1 to IIa-8, IIa-9 to IIa-20, I-1 to I-36, and II-1 to II-11), however the preferable example are not limited thereto in the invention.

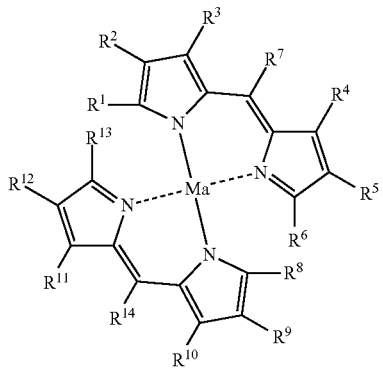

| Compound No. | $R^1 = R^6 = R^8 = R^{13}$ | $R^2 = R^5 = R^9 = R^{12}$ | $R^3 = R^4 = R^{10} = R^{11}$ | $R^7 = R^{14}$ | Ma |
|---|---|---|---|---|---|
| Ia-3 | —NH$_2$ | C$_4$H$_9$(t)<br>—COO—⟨cyclohexane⟩—CH$_3$<br>C$_4$H$_9$(t) | —CH$_3$ | —H | Co |

-continued

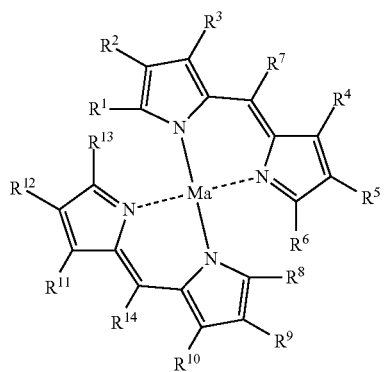

| Compound No. | $R^1=R^6=R^8=R^{13}$ | $R^2=R^5=R^9=R^{12}$ | $R^3=R^4=R^{10}=R^{11}$ | $R^7=R^{14}$ | Ma |
|---|---|---|---|---|---|
| Ia-4 | " | " | " | " | V=O |
| Ia-5 | —NHCOCH$_3$ | " | " | " | Zn |
| Ia-6 | " | " | " | " | Cu |
| Ia-7 | " | " | " | —CH$_3$ | Zn |
| Ia-8 | —NHCOCH$_2$OCH$_2$COOH | " | " | " | Zn |
| Ia-9 | " | " | " | " | Zn |
| Ia-10 | " | " | —C$_3$H$_7$(iso) | —H | Zn |
| Ia-11 | " | " | " | —CH$_3$ | Zn |
| Ia-12 | " | " | —C$_4$H$_9$(t) | —H | Cu |
| Ia-13 | —NH$_2$ | " | " | —CH$_3$ | Zn |
| Ia-14 | " | " | " | —H | Zn |
| Ia-15 | " | " | —cyclohexyl | " | Zn |
| Ia-16 | —NHCOCH$_3$ | " | —CH$_2$S—CH(CH$_3$)COOH | —CH$_3$ | Cu |
| Ia-18 | —NH$_2$ | " | —phenyl | —H | Cu |
| Ia-19 | " | " | " | " | V=O |
| Ia-20 | " | " | " | —CH$_3$ | Zn |
| Ia-21 | —NHCOCH$_3$ | " | " | " | Zn |
| Ia-22 | —NHCOCH$_2$OCH$_2$COOH | " | " | —H | Zn |
| Ia-23 | " | " | " | —CH$_3$ | Zn |

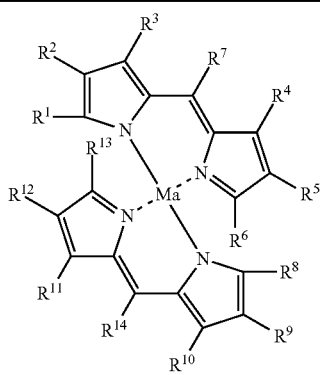

| Compound No. | $R^1=R^6=R^8=R^{13}$ | $R^2=R^5=R^9=R^{12}$ | $R^3=R^4=R^{10}=R^{11}$ | $R^7=R^{14}$ | Ma |
|---|---|---|---|---|---|
| Ia-24 | —NHCOCH$_2$OCH$_2$COOH | —COO–(2,6-di-t-C$_4$H$_9$-4-CH$_3$-cyclohexyl) | phenyl | —CH$_3$ | Cu |
| Ia-25 | ditto | ditto | 4-Cl-phenyl | ditto | Zn |
| Ia-26 | ditto | ditto | 2-CH$_3$-phenyl | ditto | Zn |
| Ia-27 | —NHCO–(2-COOH-phenyl) | ditto | —CH$_3$ | —H | Cu |
| Ia-28 | ditto | ditto | ditto | —CH$_3$ | Zn |
| Ia-29 | —NHCO–(3-SO$_3$H-phenyl) | ditto | ditto | ditto | Cu |
| Ia-30 | ditto | ditto | —CH$_2$—CH(C$_2$H$_5$)C$_4$H$_9$ | ditto | Cu |
| Ia-31 | N-maleimidyl | ditto | phenyl | ditto | Zn |
| Ia-32 | N-(3-methylmaleimidyl) | ditto | ditto | ditto | Zn |
| Ia-33 | —NHSO$_2$CH$_3$ | ditto | —CH$_3$ | ditto | Zn |

-continued

| Ia-34 | 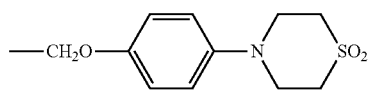 | ditto | ditto | ditto | Zn |

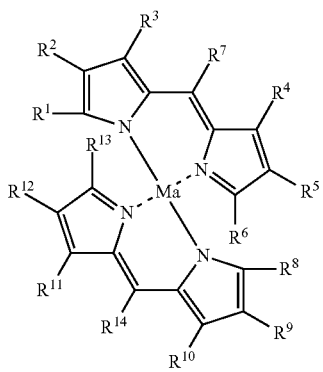

| Compound No. | $R^1=R^6=R^8=R^{13}$ | $R^2=R^5=R^9=R^{12}$ | $R^3=R^4=R^{10}=R^{11}$ | $R^7=R^{14}$ | Ma |
|---|---|---|---|---|---|
| Ia-35 | 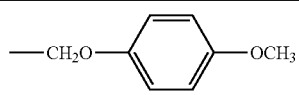 | 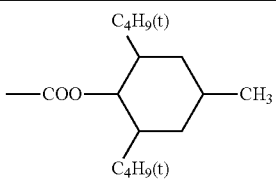 | 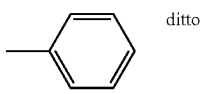 | —CH$_3$ | Zn |
| Ia-36 | 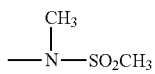 | ditto | ditto | ditto | Zn |
| Ia-37 | 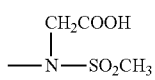 | ditto | ditto | ditto | Zn |
| Ia-38 | —Cl | ditto | ditto | ditto | Cu |
| Ia-39 | —S—CH$_2$COOH | ditto | ditto | ditto | Cu |
| Ia-40 | 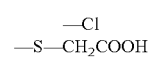 | ditto | —CH$_3$ | ditto | Cu |
| Ia-41 | ditto | ditto | ditto | ditto | V=O |
| Ia-42 | —SO$_2$CH$_3$ | ditto | ditto | ditto | V=O |
| Ia-43 | ditto | ditto | 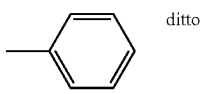 | ditto | Cu |
| Ia-44 | 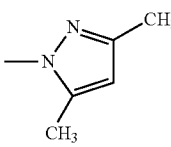 | ditto | ditto | ditto | Cu |
| Ia-45 | —CH$_3$ | ditto | —CH$_3$ | —H | Cu |
| Ia-46 | ditto | ditto | ditto | —CH$_3$ | Zn |
| Ia-47 | ditto | ditto | ditto | ditto | Cu |
| Ia-48 | ditto | ditto | ditto | ditto | Ni |
| Ia-49 | —C$_4$H$_9$(t) | ditto | ditto | ditto | Zn |
| Ia-50 | ditto | ditto | ditto | ditto | Pd |
| Ia-51 | —CH$_2$CH$_2$COOH | ditto | ditto | ditto | Zn |

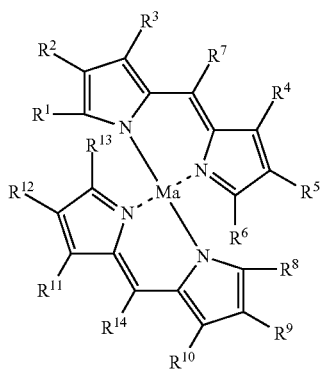

| Compound No. | $R^1=R^6=R^8=R^{13}$ | $R^2=R^5=R^9=R^{12}$ |
|---|---|---|
| Ia-52 | —CH₂CH₂COOH | —COO—C₆H₉(2,6-di-t-C₄H₉-4-CH₃) |
| Ia-53 | —CH₃ | ditto |
| Ia-54 | ditto | ditto |
| Ia-55 | ditto | ditto |
| Ia-56 | ditto | ditto |
| Ia-57 | —C₆H₅ (phenyl) | ditto |
| Ia-58 | ditto | ditto |
| Ia-59 | —C₆H₄-COOH (4-) | ditto |
| Ia-60 | ditto | —COOCH₂—CH(C₆H₁₃)C₈H₁₇ |
| Ia-61 | —C₆H₄-NHCOCH₂CH₂COOH (3-) | —COOCH₂—CH(C₂H₅)C₄H₉ |
| Ia-62 | 2-pyridyl | —COO—C₆H₉(2,6-di-t-C₄H₉-4-CH₃) |
| Ia-63 | —CH₃ | ditto |

| Compound No. | $R^3=R^4=R^{10}=R^{11}$ | $R^7=R^{14}$ | Ma |
|---|---|---|---|
| Ia-52 | —C₆H₅ (phenyl) | —CH₃ | Zn |
| Ia-53 | ditto | ditto | Zn |

-continued

| Compound No. | | | Metal |
|---|---|---|---|
| Ia-54 | ![4-methylbenzoic acid group] —C6H4—COOH | ditto | Zn |
| Ia-55 | ditto | ditto | Cu |
| Ia-56 | ditto | —C6H5 (phenyl) | Zn |
| Ia-57 | —CH₃ | —H | Zn |
| Ia-58 | ditto | —CH₃ | Zn |
| Ia-59 | —CH₂O—C6H4—N(morpholino-SO₂) | ditto | Zn |
| Ia 60 | —CH₂CH₂—O—C6H4—OCH₃ | ditto | Zn |
| Ia-61 | ditto | ditto | Zn |
| Ia-62 | ditto | ditto | Zn |
| Ia-63 | ditto | ditto | Cu |

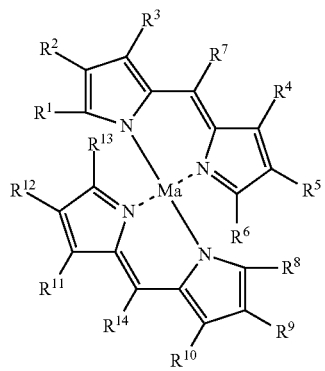

| Compound No. | $R^1=R^6=R^8=R^{13}$ | $R^2=R^5=R^9=R^{12}$ |
|---|---|---|
| Ia-67 | —NH₂ | —CN |
| Ia-68 | —NHCOCH₃ | ditto |
| Ia-69 | —CH₃ | ditto |
| Ia-70 | ditto | ditto |
| Ia-71 | —C₁₃H₂₇ | ditto |
| Ia-72 | —NH₂ | ditto |
| Ia-73 | —NHCOCH₂OCH₂COOH | ditto |
| Ia-74 | —NHCO—CH(C₄H₉)O—C6H4—N(morpholino-SO₂) | ditto |
| Ia-75 | —C6H4—CO—N(CH₂CH₂OCH₃)₂ | ditto |
| Ia-76 | ditto | ditto |
| Ia-77 | ditto | ditto |
| Ia-78 | —NHCOCH₂OCH₂COOH | ditto |

-continued

| | | |
|---|---|---|
| Ia-79 | 2-methylpyridinyl | —COO-(2,6-di-t-butyl-4-methylcyclohexyl) |
| Ia-80 | ditto | ditto |
| Ia-81 | —C₁₃H₂₇ | ditto |
| Ia-82 | —NHCOCH₂OCH₂COOH | —COOC₂H₅ |
| Ia-83 | 3-methylphenyl-SO₂—N(CH₂COOH)₂ | —COO-(2,6-di-t-butyl-4-methylcyclohexyl) |

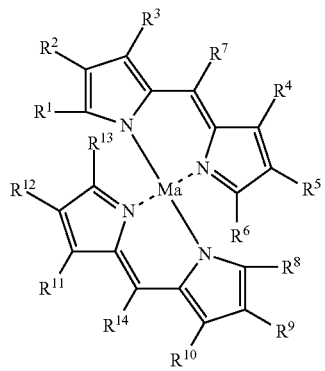

| Compound No. | R3=R4=R10=R11 | R7=R14 | Ma |
|---|---|---|---|
| Ia-67 | —CH₃ | —H | Zn |
| Ia-68 | ditto | —CH₃ | Zn |
| Ia-69 | ditto | ditto | Zn |
| Ia-70 | phenyl | ditto | Zn |
| Ia-71 | —CH₃ | phenyl | Cu |
| Ia-72 | —CF₃ | ditto | Cu |
| Ia-73 | ditto | ditto | Cu |
| Ia-74 | ditto | —CH₃ | Zn |
| Ia-75 | —C₃H₇(iso) | ditto | Zn |
| Ia-76 | phenyl | ditto | Zn |
| Ia-77 | —CF₃ | ditto | Zn |
| Ia-78 | 4-(—CO—N(CH₂CH₂OCH₃)₂)phenyl | ditto | Zn |

-continued
| | | | |
|---|---|---|---|
| Ia-79 | 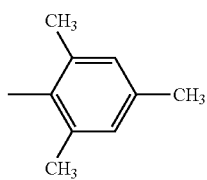 | —H | Zn |
| Ia-80 | —C$_4$H$_9$(t) | ditto | Zn |
| Ia-81 | 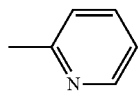 | ditto | Zn |
| Ia-82 | 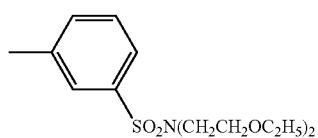 | ditto | Cu |
| Ia-83 | —CH$_3$ | ditto | Zn |
IIa-1
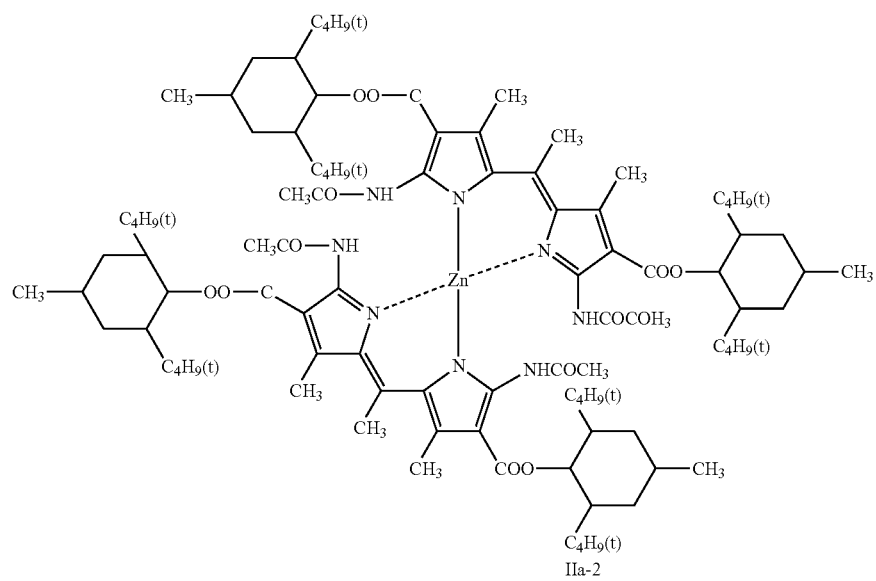
IIa-2  IIa-3
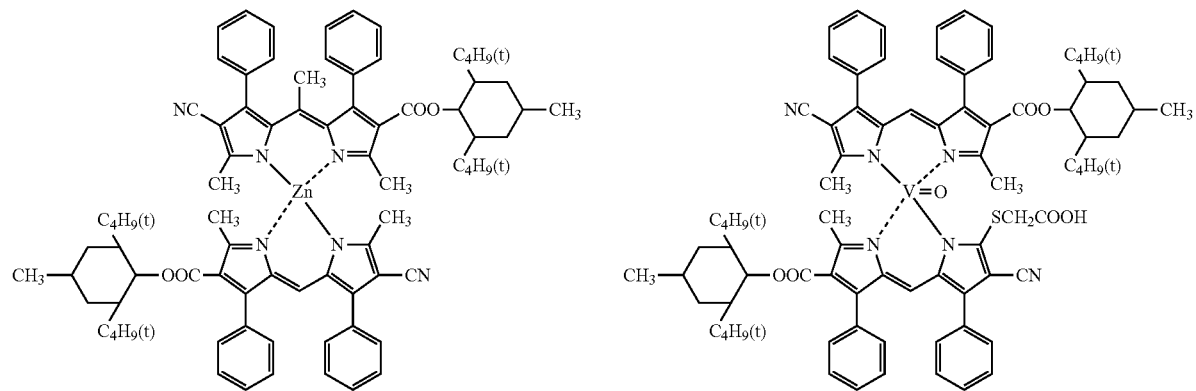

-continued
IIa-4
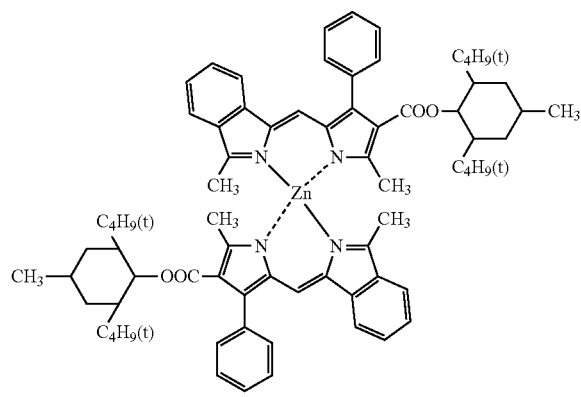
IIa-5
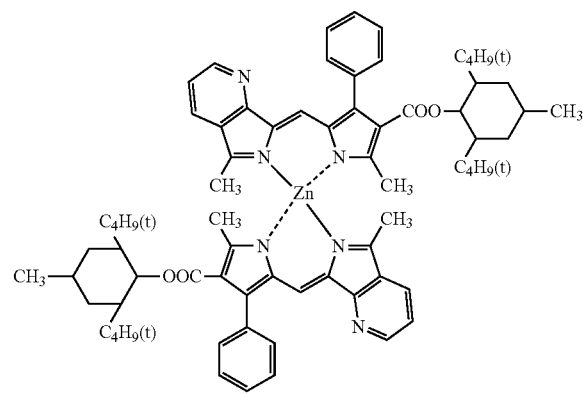
IIa-6
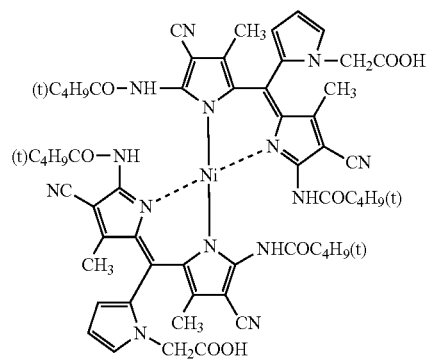
IIa-7
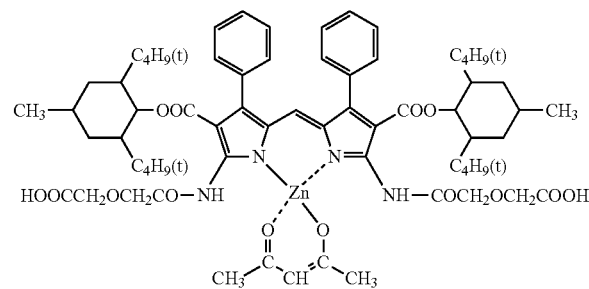
IIa-8
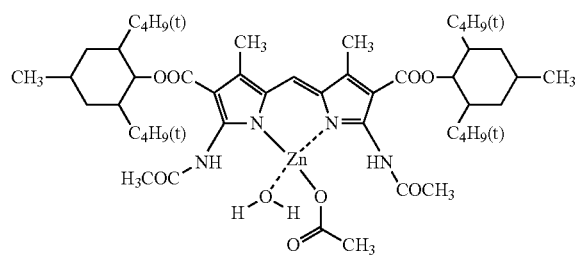
IIa-10
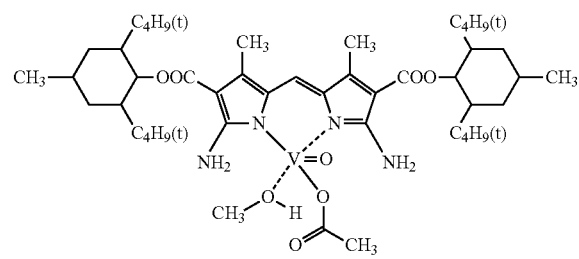
IIa-11
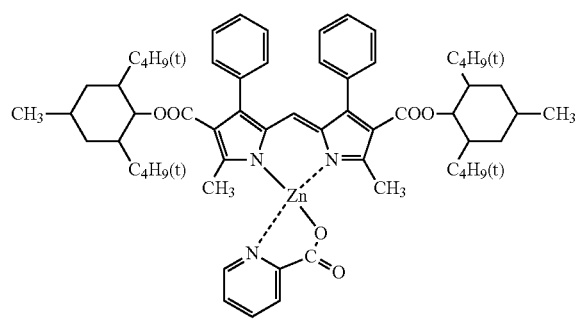
IIa-12
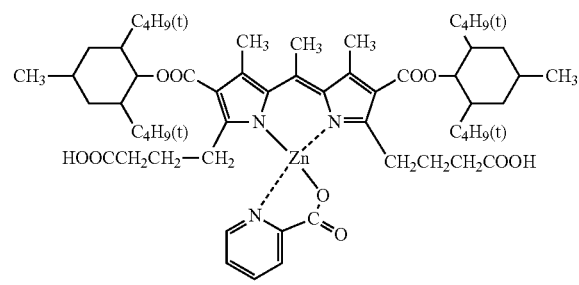

-continued
IIa-13
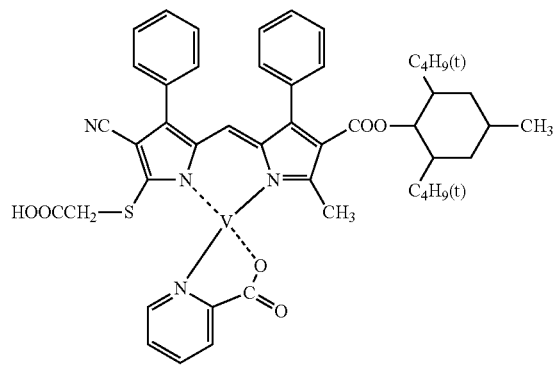
IIa-14
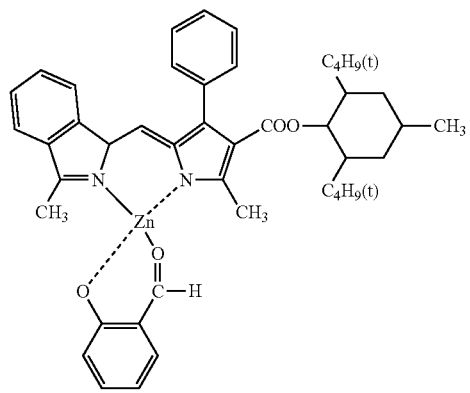
IIa-15
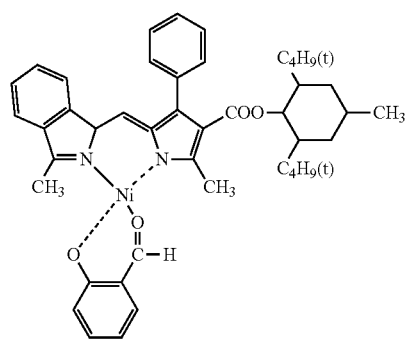
IIa-16
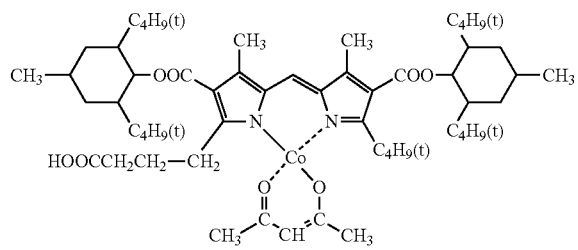
IIa-17
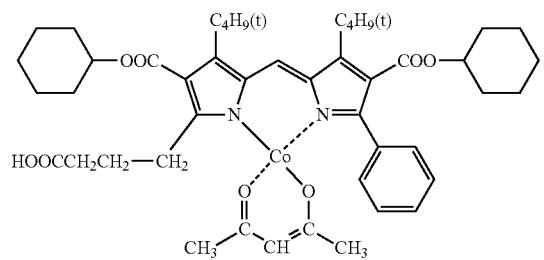
IIa-18
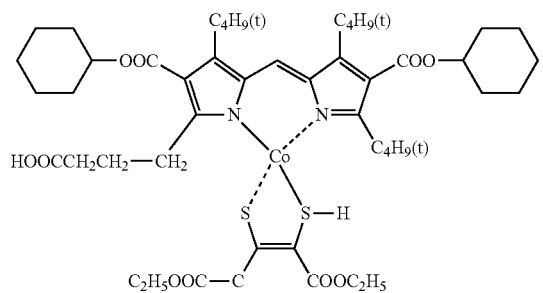
IIa-19
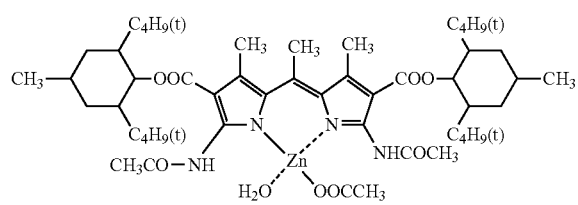
IIa-20
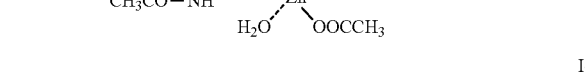
I-1
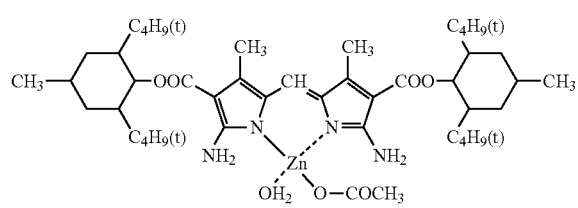
I-2
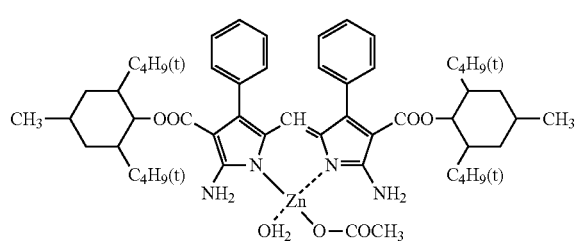

-continued
I-3
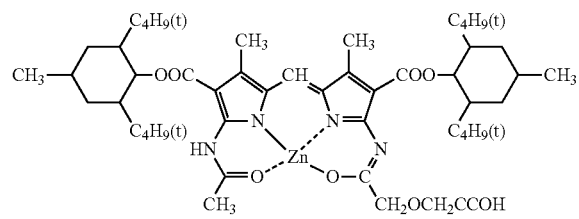
I-4
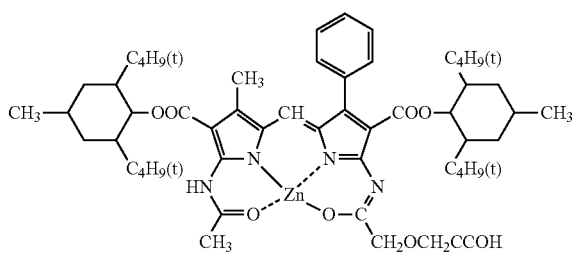
I-5
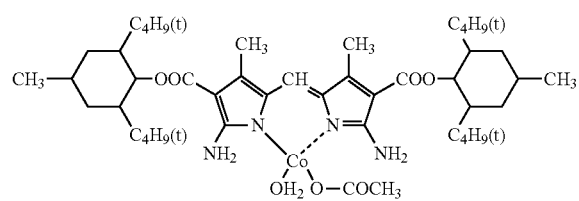
I-6
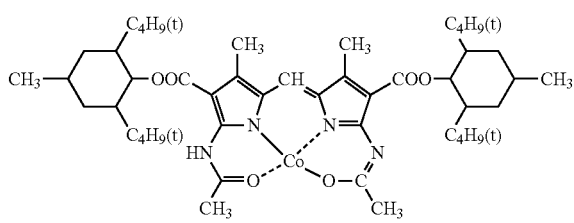
I-7
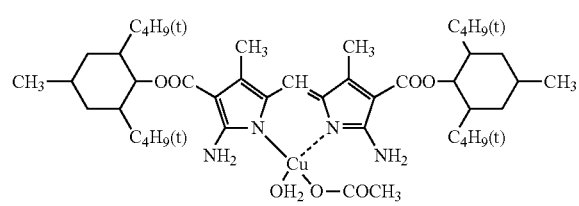
I-8
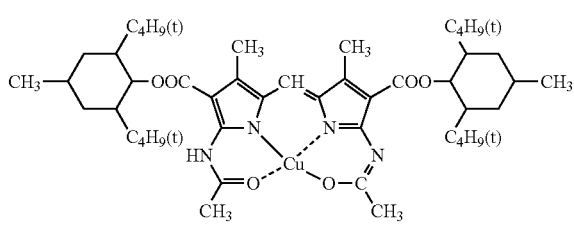
I-9
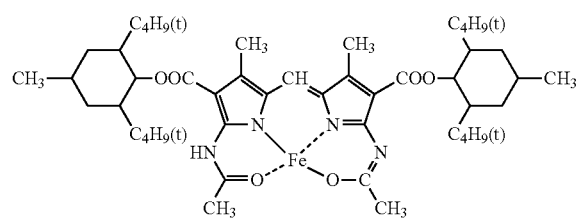
I-10
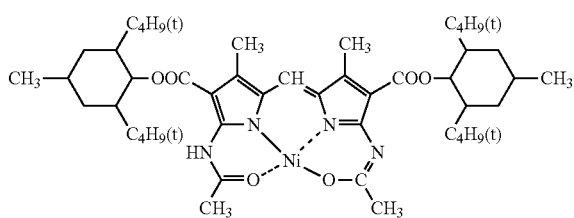
I-11
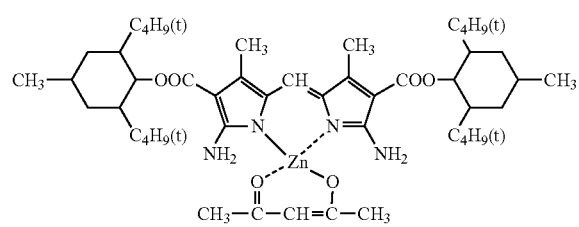
I-12
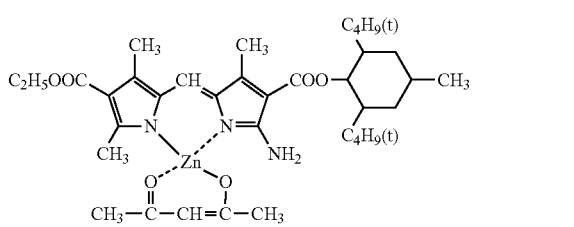
I-13
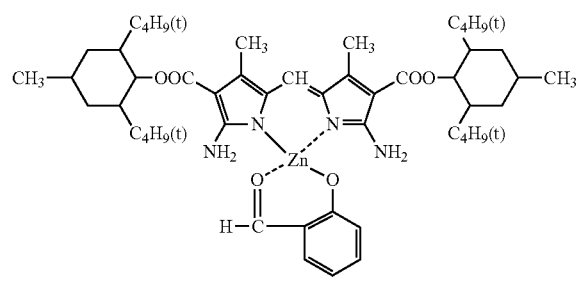
I-14
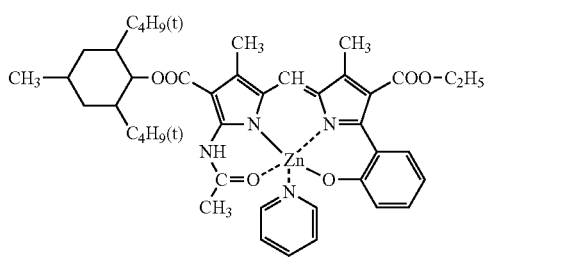

-continued
I-15
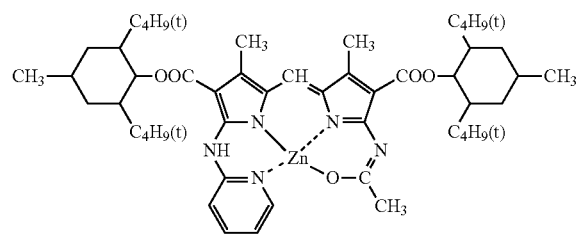
I-16
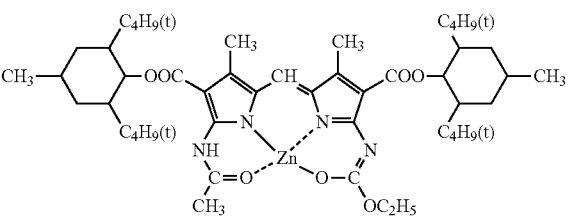
I-17
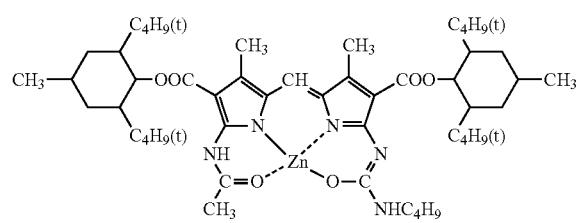
I-18
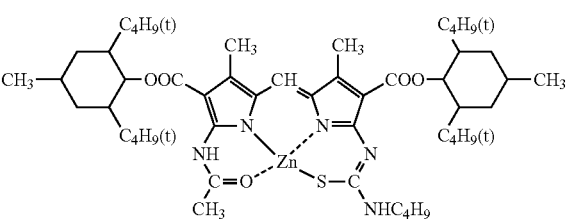
I-19
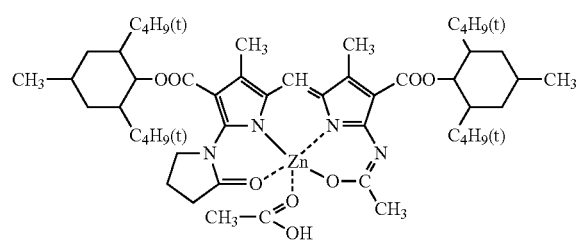
I-20
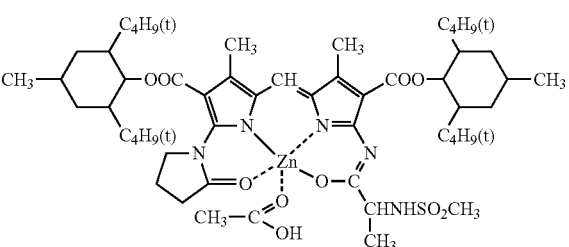
I-21
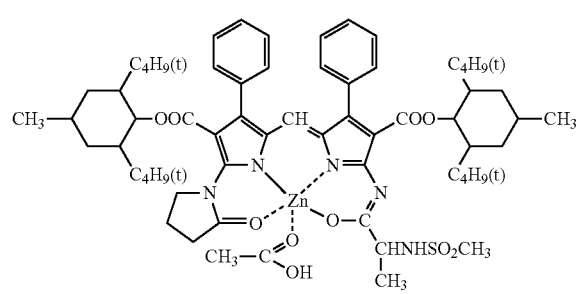
I-22
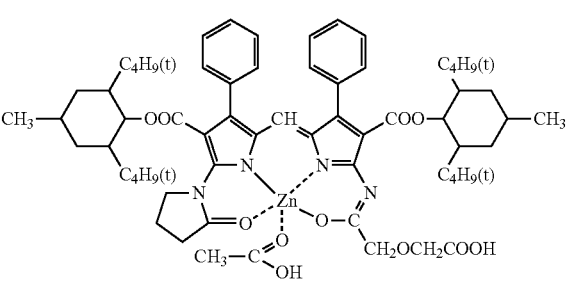
I-23
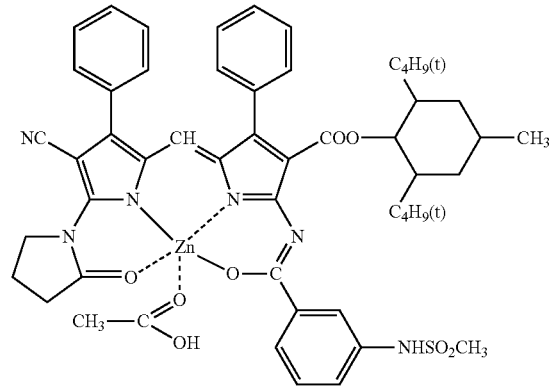
I-24
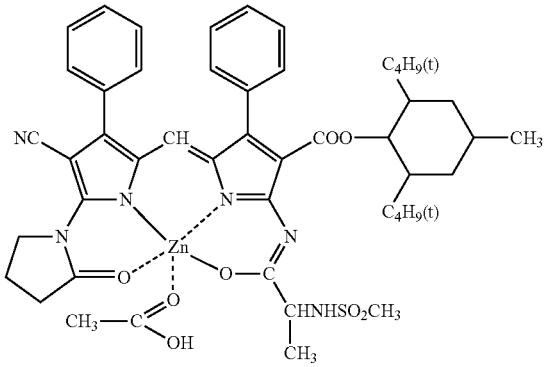

-continued
I-25
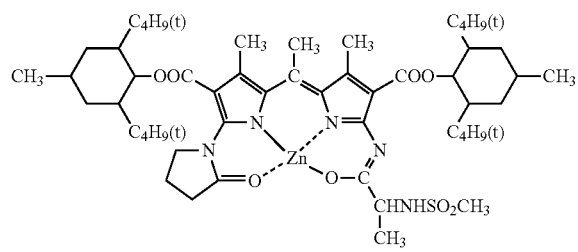
I-26
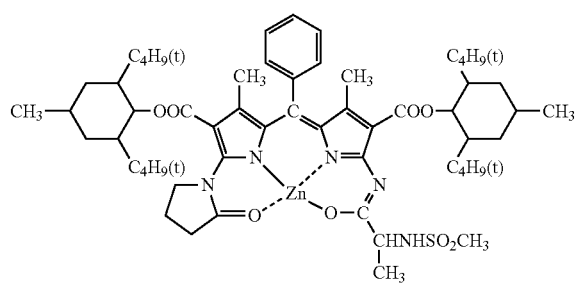
I-27
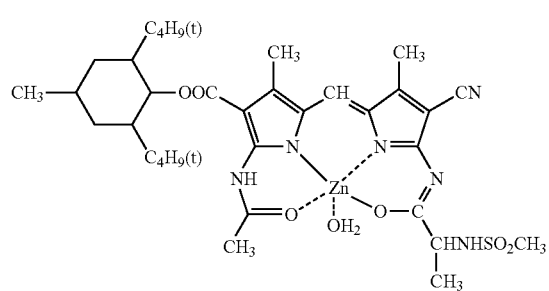
I-28
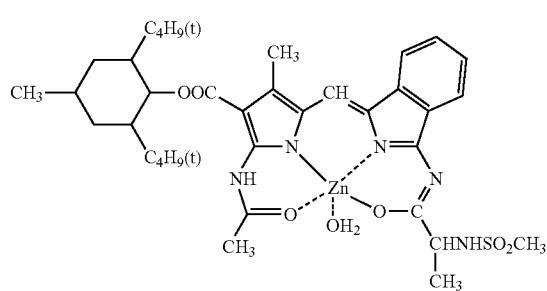
I-29
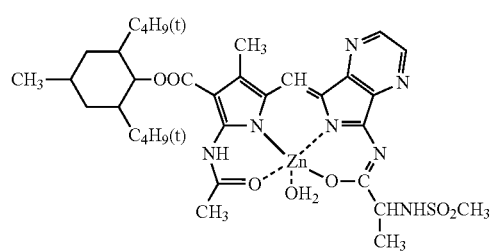
I-30
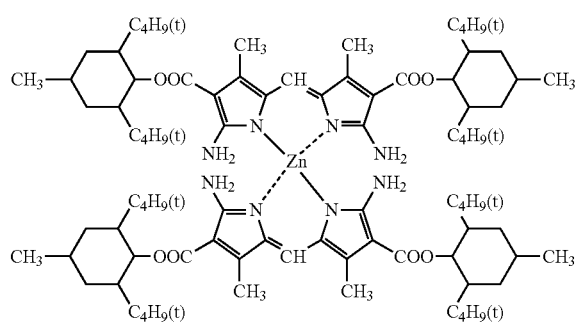
I-31
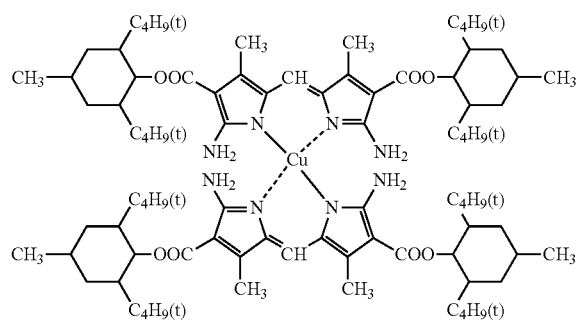
I-32
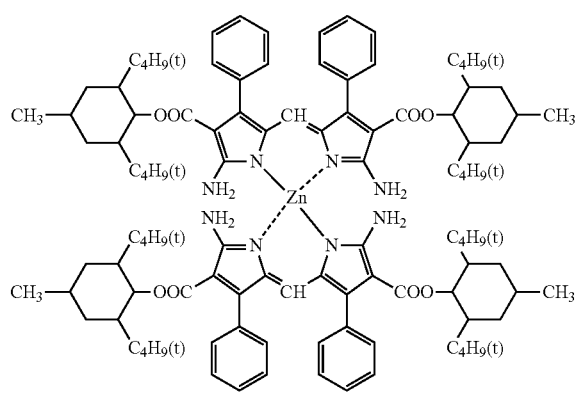

-continued
I-33
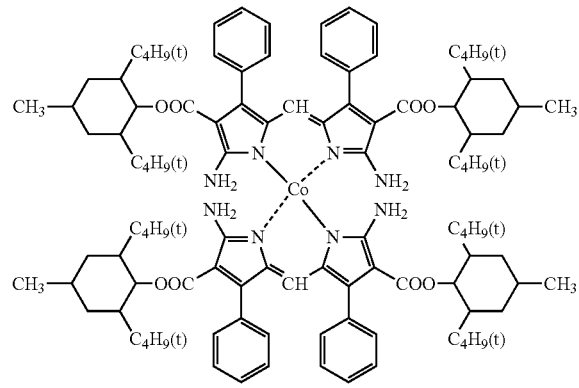
I-34
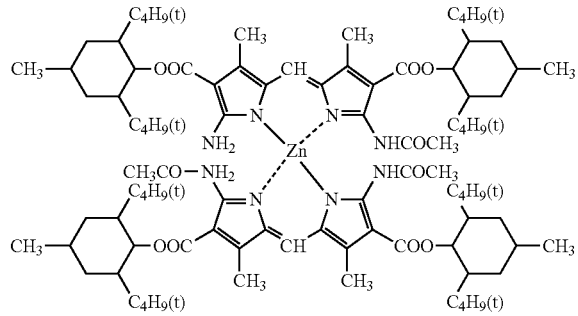
I-35
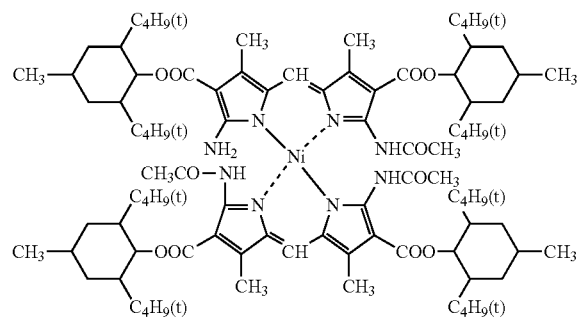
I-36
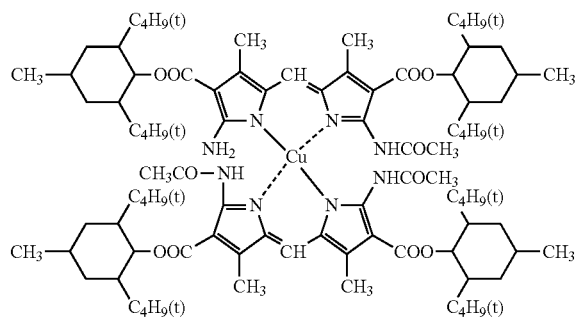
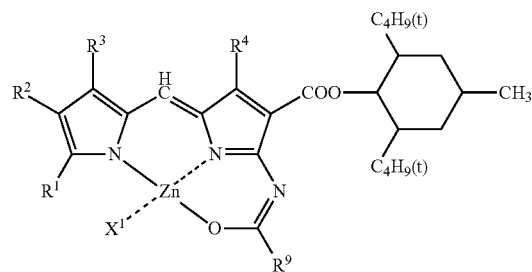
| Compound No. | R$^1$ | R$^2$ | R$^3$ | R$^4$ | R$^9$ | X$^1$ |
|---|---|---|---|---|---|---|
| II-1 | —CH$_3$ | —COOC$_2$H$_5$ | —CH$_3$ | —CH$_3$ | —CH$_3$ | H$_2$O |
| II-2 | ditto | ditto | ditto | ditto | —CH(CH$_3$)NHSO$_2$CH$_3$ | ditto |
| II-3 | ditto | ditto | ditto | ditto | m-(CH$_3$)C$_6$H$_4$NHSO$_2$CH$_3$ | ditto |

-continued

| Compound No. | | | | | | |
|---|---|---|---|---|---|---|
| II-4 | 3-(NHSO₂CH₃)-phenyl | —COOCH₃ | ditto | phenyl | —CH₃ | ditto |
| II-5 | 3-(NHSO₂CH₃)-phenyl | —COOC₂H₅ | ditto | ditto | —CH₂OCH₂COOH | ditto |
| II-6 | ditto | ditto | ditto | ditto | —CH₃ | ditto |

Structure: Zn complex with dipyrromethene bearing R¹ on pyrrole N-substituent, R², R³ on one pyrrole ring, R⁴ on other pyrrole ring, —COO-(2,6-di-t-butyl-4-methylcyclohexyl) ester, and N=C(R⁹)—O coordinated to Zn with X¹ axial ligand.

| Compound No. | R¹ | R² | R³ | R⁴ | R⁹ | X¹ |
|---|---|---|---|---|---|---|
| II-7 | —CH₃ | —COOC₂H₅ | phenyl | phenyl | —CH₃ | H₂O |
| II-8 | 3-pyridyl | ditto | ditto | ditto | ditto | ditto |
| II-9 | 3-(NHSO₂CH₃)-phenyl | ditto | —CH₃ | —CH₃ | ditto | ditto |
| II-10 | 3-(NHSO₂CH₃)-phenyl | ditto | ditto | ditto | 3-(NHSO₂CH₃)-phenyl | ditto |
| II-11 | ditto | ditto | phenyl | phenyl | —CH₃ | ditto |

Specific examples of the particular metal complex compounds III are shown below (exemplary compounds III-1 to III-103), however the preferable examples are not limited thereto in the invention.

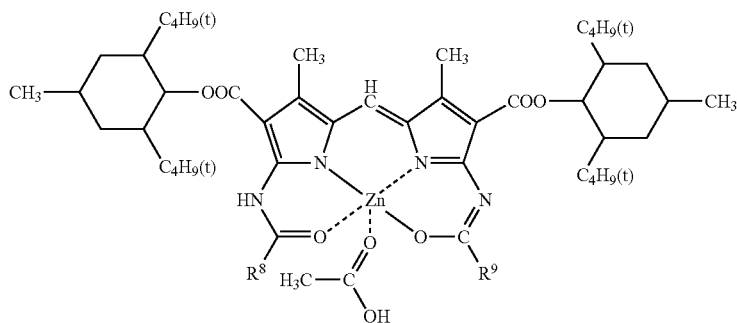

| Compound No | R⁸ | R⁹ | Compound No. | R⁸ | R⁹ |
|---|---|---|---|---|---|
| III-1 | —CH$_3$ | —CH$_3$ | III-2 | —CH(C$_2$H$_5$)C$_4$H$_9$ | —CH$_3$ |
| III-3 | —C$_4$H$_9$(t) | ditto | III-4 | —CH(C$_2$H$_5$)C$_4$H$_9$ | —CH(C$_2$H$_5$)C$_4$H$_9$ |
| III-5 | —C$_4$H$_9$(t) | —C$_4$H$_9$(t) | III-6 | —C$_6$H$_{11}$ (cyclohexyl) | —CH$_3$ |
| III-7 | —CH(CH$_3$)S—C$_4$H$_9$ | —CH$_3$ | III-8 | —CH$_2$OCH$_3$ | ditto |
| III-9 | —CH(C$_2$H$_5$)—O—C$_6$H$_4$—OCH$_3$ | ditto | III-10 | —CH(C$_2$H$_5$)—O—C$_6$H$_4$—N(SO$_2$)(morpholine-sulfonyl) | ditto |
| III-11 | —CH(CH$_3$)—S—CH$_2$COOC$_2$H$_5$ | ditto | III-12 | —C(CH$_3$)=CH$_2$ | ditto |
| III-13 | —C(CH$_3$)$_2$—COOCH$_3$ | ditto | III-14 | —CO—CH(CH$_3$)—COCH$_3$ | ditto |
| III-15 | —CH$_2$OCH$_2$COOC$_2$H$_5$ | ditto | III-16 | —CH$_2$NHSO$_2$CH$_3$ | ditto |
| III-17 | —CH(CH$_3$)NHSO$_2$CH$_3$ | ditto | III-18 | —CH(C$_2$H$_5$)NHSO$_2$CH$_3$ | ditto |
| III-19 | —CH(C$_4$H$_9$)NHSO$_2$CH$_3$ | ditto | III-20 | —CH(CH(CH$_3$)$_2$)NHSO$_2$CH$_3$ | ditto |
| III-21 | —CH(CH$_3$)NHSO$_2$—C$_4$H$_9$ | ditto | III-22 | —CH(CH$_3$)NHSO$_2$—C$_6$H$_4$—CH$_3$ | ditto |
| III-23 | —CH(CH$_3$)NHSO$_2$—C$_6$H$_4$—NHSO$_2$CH$_3$ | ditto | III-24 | —CH(CH$_3$)NHSO$_2$—N(C$_2$H$_5$)$_2$ | ditto |

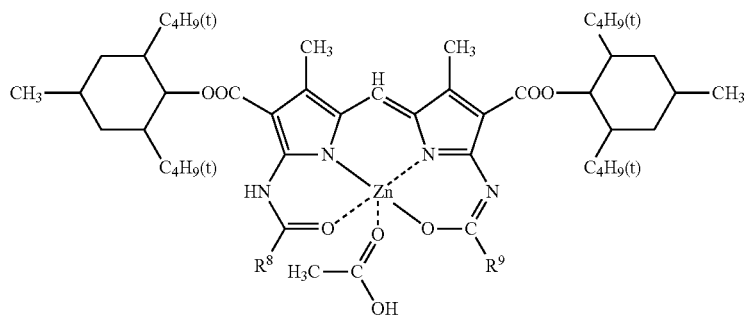

| Compound No. | R⁸ | R⁹ | Compound No. | R⁸ | R⁹ |
|---|---|---|---|---|---|
| III-25 | (1-phthalimidoethyl, —CH(CH₃)—N(phthalimide)) | —CH₃ | III-26 | —CH₂CH₂COOC₂H₅ | —CH₃ |
| III-27 | —CH(CH₃)—S—(2-COOCH₃-phenyl) | ditto | III-28 | —CH(CH₃)—S—(2-pyridyl) | ditto |
| III-29 | —CH₂NHSO₂CH₃ | —CH₂NHSO₂CH₃ | III-30 | —CH₂—CH(CH₃)NHSO₂CH₃ | —CH₂—CH(CH₃)NHSO₂CH₃ |
| III-31 | —CH₂NHSO₂CH₃ | —CH(C₂H₅)C₄H₉ | III-32 | —CH₂—CH(CH₃)NHSO₂CH₃ | —C₄H₉(t) |
| III-33 | —C₆H₅ (phenyl) | —CH₃ | III-34 | —C₆H₅ (phenyl) | —CH₂—CH(CH₃)NHSO₂CH₃ |

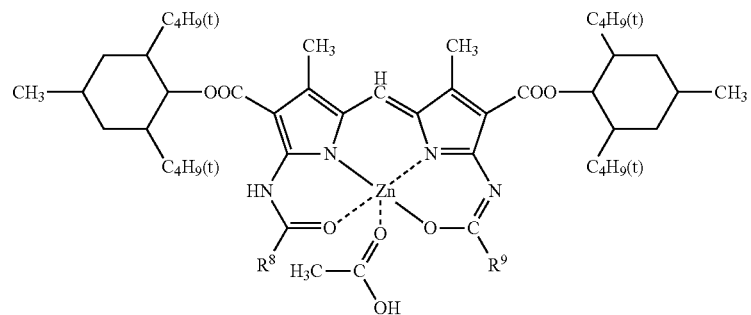

| Compound No. | R⁸ | R⁹ | Compound No. | R⁸ | R⁹ |
|---|---|---|---|---|---|
| III-35 | —(4-C₄H₉(t)-phenyl) | —CH₃ | III-36 | —(3-NHSO₂CH₃-phenyl) | —CH₃ |

-continued

| | | | | | |
|---|---|---|---|---|---|
| III-37 | 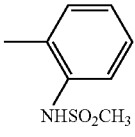 | ditto | III-38 | 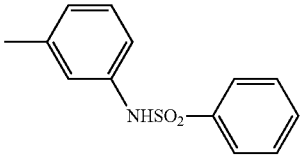 | ditto |
| III-39 | 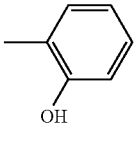 | ditto | III-40 | 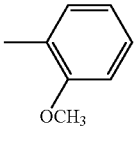 | ditto |
| III-41 | 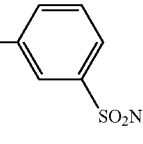 | ditto | III-42 | 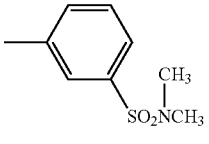 | ditto |
| III-43 | 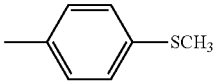 | ditto | III-44 | 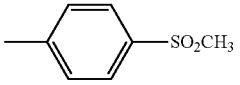 | ditto |

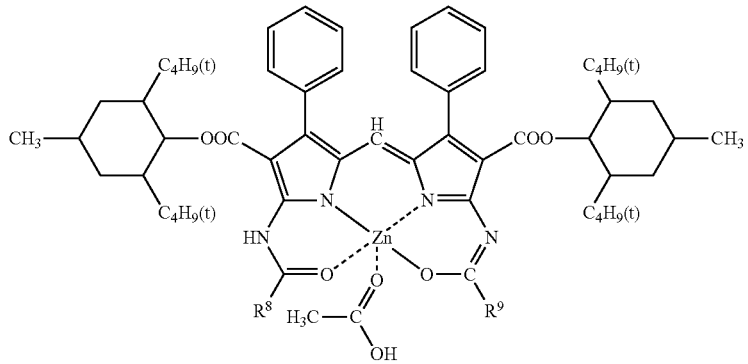

| Compound No. | $R^8$ | $R^9$ | Compound No. | $R^8$ | $R^9$ |
|---|---|---|---|---|---|
| III-45 | —$CH_3$ | —$CH_3$ | III-46 | $\underset{\underset{C_2H_5}{\vert}}{-CHC_4H_9}$ | $\underset{\underset{C_2H_5}{\vert}}{-CHC_4H_9}$ |
| III-47 | —$C_4H_9(t)$ | —$C_4H_9(t)$ | III-48 |  |  |
| III-49 | —$CH_2NHSO_2CH_3$ | —$CH_3$ | III-50 | —$CH_2NHSO_2CH_3$ | —$CH_2NHSO_2CH_3$ |
| III-51 | $\underset{\underset{CH_3}{\vert}}{-CHNHSO_2CH_3}$ | ditto | III-52 | $\underset{\underset{CH_3}{\vert}}{-CHNHSO_2CH_3}$ | $\underset{\underset{CH_3}{\vert}}{-CHNHSO_2CH_3}$ |
| III-53 | $\underset{\underset{C_4H_9}{\vert}}{-CHNHSO_2CH_3}$ | ditto | III-54 | 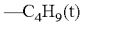 | ditto |
| III-55 | 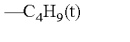 | 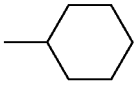 | III-56 | 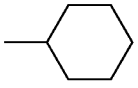 | ditto |

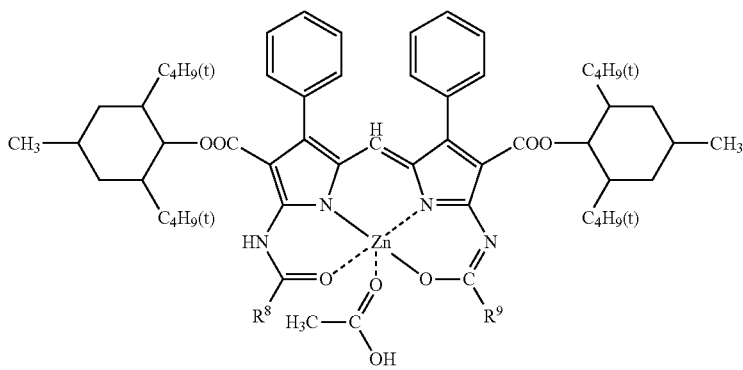

| Compound No. | R⁸ | R⁹ | Compound No. | R⁸ | R⁹ |
|---|---|---|---|---|---|
| III-57 | 2,3,4,6-tetramethylphenyl | —CH₃ | III-58 | 2,3,4,6-tetramethylphenyl | 2,3,4,6-tetramethylphenyl |
| III-59 | 2-methyl-6-(OCH₂CH₂OH)phenyl | ditto | III-60 | 3-methyl-4-(COOCH₃)phenyl | —CH₃ |
| III-61 | 2-methyl-3-OCH₃-6-OCH₃-phenyl | ditto | III-62 | 2-methyl-6-(NHSO₂CH₃)phenyl | ditto |
| III-63 | 2-pyridyl | ditto | III-64 | 2-pyridyl | 2-pyridyl |

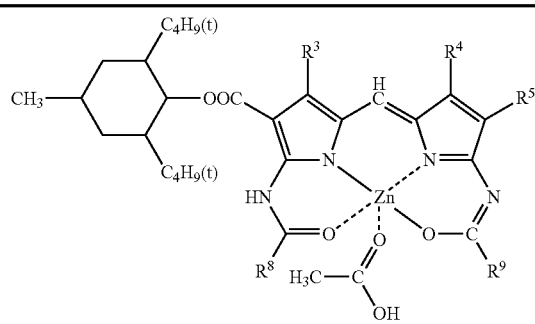

| Compound No. | R³ | R⁴ | R⁵ | R⁸ | R⁹ |
|---|---|---|---|---|---|
| III-65 | —CH₃ | —CH₃ | —COOC₂H₅ | —CH₃ | —CH₃ |
| III-66 | ditto | ditto | ditto | —CH(CH₃)NHSO₂CH₃ | —CH(CH₃)NHSO₂CH₃ |
| III-67 | ditto | ditto | ditto | 3-(NHSO₂CH₃)phenyl | 3-(NHSO₂CH₃)phenyl |

-continued

| Compound No. | | | | | |
|---|---|---|---|---|---|
| III-68 | ⌬ (phenyl) | ditto | ditto | —CH₃ | —CH₃ |
| III-69 | ⌬ (phenyl) | ⌬ (phenyl) | ditto | ditto | ditto |
| III-70 | —CH₃ | ⌬ (phenyl) | —COO-(2,6-di-t-Bu-4-Me-cyclohexyl) | ditto | —CH₂NHSO₂-C₆H₄-CH₃ |

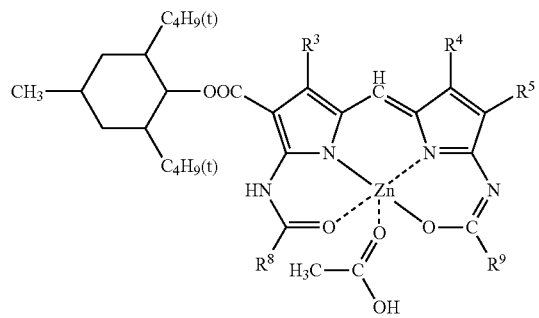

| Compound No. | R³ | R⁴ | R⁵ | R⁸ | R⁹ |
|---|---|---|---|---|---|
| III-71 | ⌬ (phenyl) | ⌬ (phenyl) | —CO—N(CH₃)(CH₃) | —CH₃ | —CH₂NHSO₂-C₆H₄-CH₃ |
| III-72 | ditto | ditto | —CO—N(C₃H₇(iso))(C₃H₇(iso)) | ditto | ditto |
| III-73 | ditto | ditto | —CONH-cyclohexyl | ditto | ditto |
| III-74 | ditto | ditto | —CONH-(2,4,6-trimethylphenyl) | ditto | ditto |
| III-75 | ditto | ditto | —CON(CH₃)-C₆H₅ | ditto | ditto |

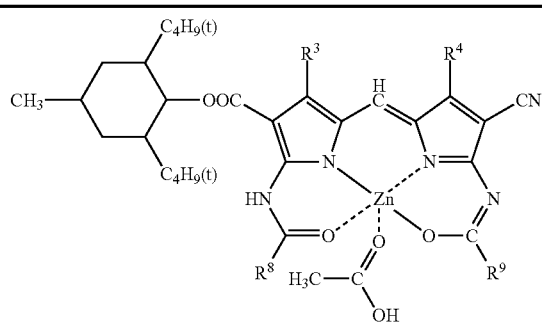

| Compound No | R³ | R⁴ | R⁸ | R⁹ |
|---|---|---|---|---|
| III-76 | —CH₃ | —CH₃ | —CH₃ | —CH₃ |
| III-77 | ditto | ditto | —CH(CH₃)NHSO₂CH₃ | ditto |
| III-78 | ditto | ditto | ditto | —CH(CH₃)NHSO₂CH₃ |
| III-79 | ditto | ditto | —CH(CH₃)NHSO₂CH₃ | —CH(CH₃)NHSO₂CH₃ |
| III-80 | ditto | —C₆H₅ | —CH₃ | —CH₃ |
| III-81 | ditto | ditto | ditto | —CH(CH₃)NHSO₂CH₃ |
| III-82 | ditto | ditto | —CH(CH₃)NHSO₂CH₃ | ditto |

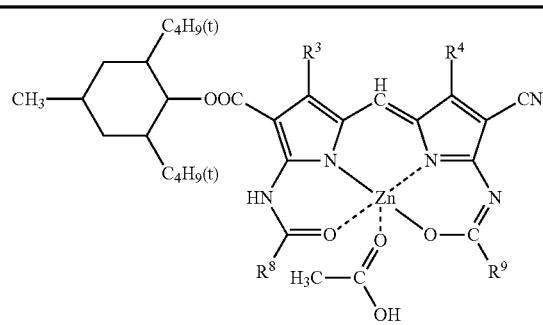

| Compound No. | R³ | R⁴ | R⁸ | R⁹ |
|---|---|---|---|---|
| III-83 | —CH₃ | —C₆H₅ | —CH(CH₃)NHSO₂CH₃ | —CH(CH₃)NHSO₂CH₃ |
| III-84 | ditto | ditto | ditto | —C₆H₄(NHSO₂CH₃) (m) |
| III-85 | ditto | ditto | —C₄H₉(t) | ditto |

-continued
| | | | | |
|---|---|---|---|---|
| III-86 | 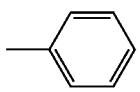 | —CH₃ | —CH₃ | —CH₃ |
| III-87 | ditto | ditto | —CH₂NHSO₂CH₃ | —CH₂NHSO₂CH₃ |
| III-88 | 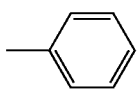 | 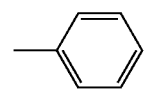 | —CH₃ | —CH₃ |
| III-89 | —CH₃ | 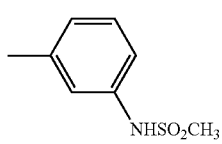 | ditto | ditto |
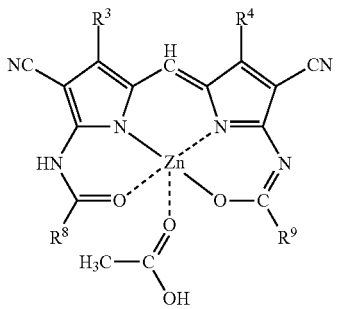
| Compound No. | R³ | R⁴ | R⁸ | R⁹ |
|---|---|---|---|---|
| III-90 | —CH₃ | —CH₃ | —CH₃ | —CH₃ |
| III-91 | ditto | ditto | ditto | —CHNHSO₂CH₃<br>\|<br>C₄H₉ |
| III-92 | ditto | ditto | —CHNHSO₂CH₃<br>\|<br>C₄H₉ | ditto |
| III-93 | 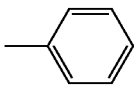 | 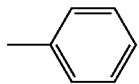 | —CH₃ | —CH₃ |
| III-94 | ditto | ditto | —C₄H₉(t) | —C₄H₉(t) |
| III-95 | ditto | ditto | —CHNHSO₂CH₃<br>\|<br>C₄H₉ | ditto |
| III-96 | ditto | ditto | 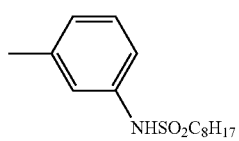 | —CH₃ |
| III-97 | 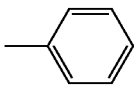 | 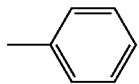 | —CH₃ | —CH₃ |

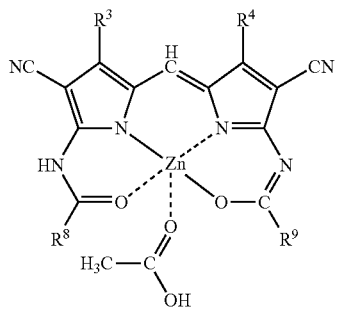

| Compound No. | R³ | R⁴ | R⁸ | R⁹ |
|---|---|---|---|---|
| III-98 | 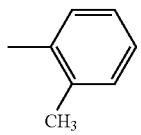 | 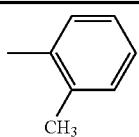 | —CH₃ | —CH₃ |
| III-99 | 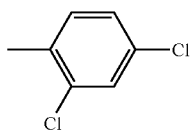 | 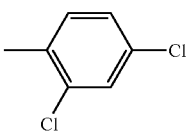 | ditto | ditto |
| III-100 | 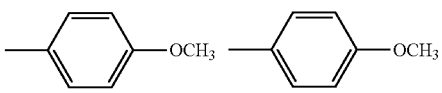 | | ditto | ditto |
| III-101 | 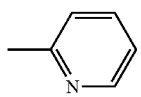 | 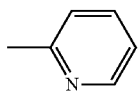 | ditto | ditto |
| III-102 | 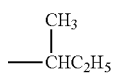 | 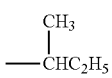 | 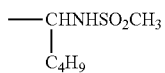 | 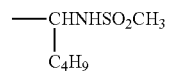 |
| III-103 | 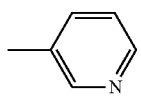 | 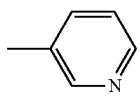 | 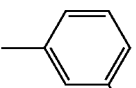 | 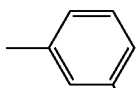 |

The metal complex compounds I obtained from the compounds represented by Formula (I) (including particular metal complex compounds II-1, II-2, III, and IV) can be synthesized by the methods described in U.S. Pat. Nos. 4,774,339 and 5,433,896, JP-A Nos. 2001-240,761 and 2002-155,052, Japanese Patent No. 3,614,586, Aust. J. Chem. 1, 965, 11, 1835-1,845, J. H. Boger et al, Heteroatom Chemistry, Vol. 1, No. 5, 389 (1990), and others. The method of synthesizing the dipyrromethene-based metal complex compound of the invention will be described below in detail along the following reaction schemes A, B, and C, by taking the exemplary compound I-30, I-31, III-1 or III-80 as an example.

Reaction scheme A

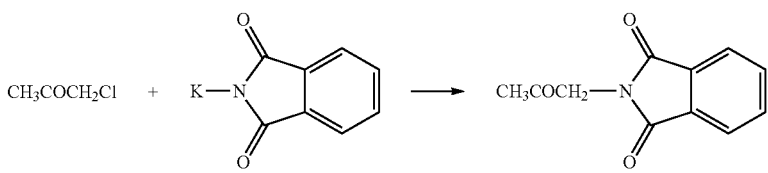

Intermediate 1

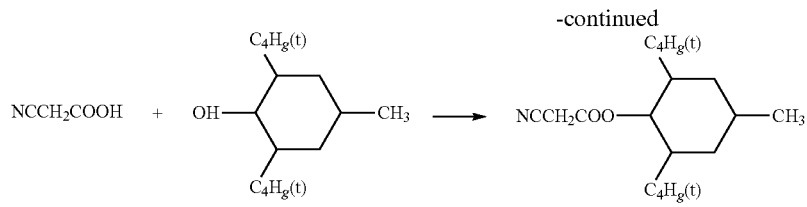

-continued

Intermediate 2

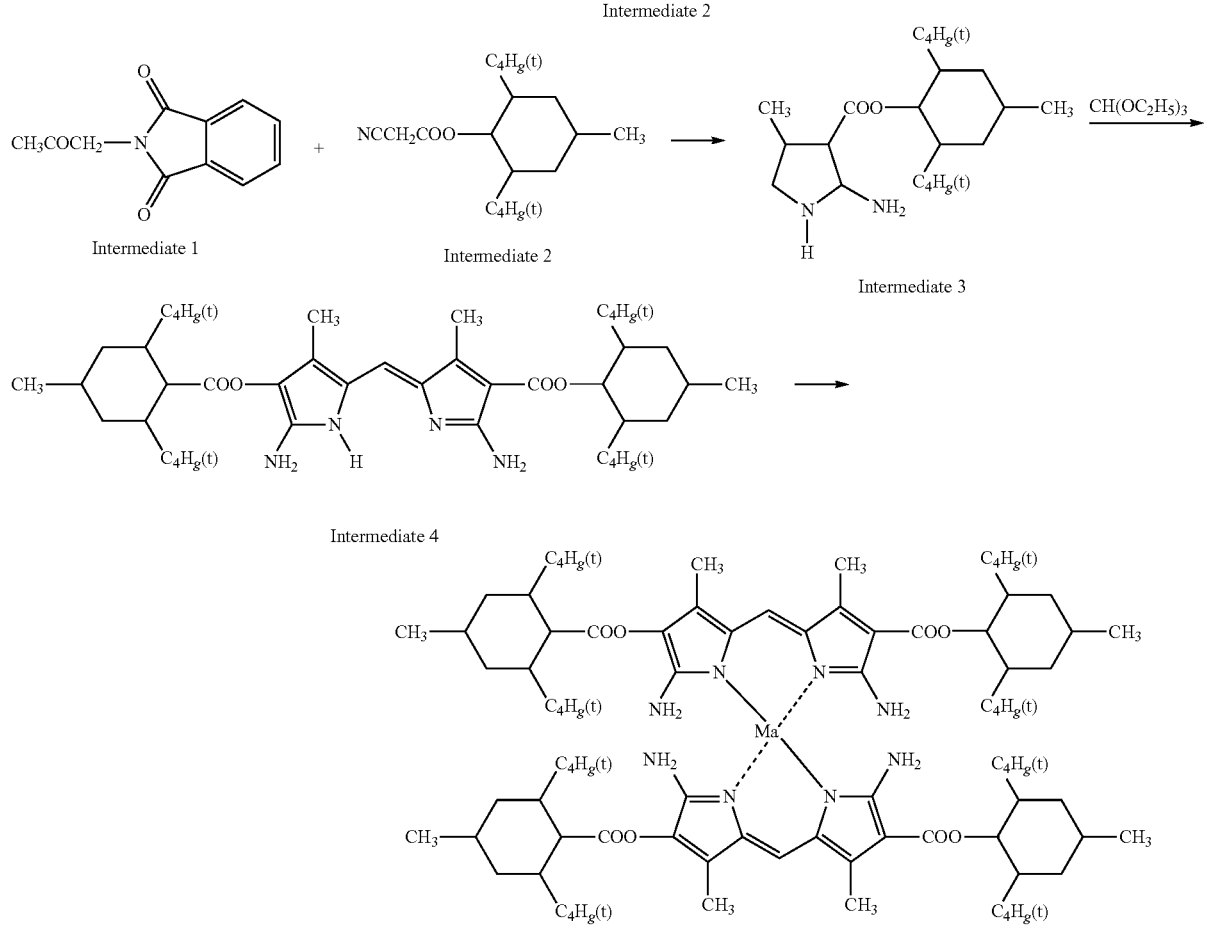

Intermediate 4

Exemplary compound I-30 Ma=Zn

Exemplary compound I-31 Ma=Cu

Synthesis of Intermediate 1

96.2 g (1.04 mol) of chloroacetone was added to 300 ml of N-methylpyrrolidone (NMP), and the mixture was stirred at 15 to 20° C. 175 g (0.945 mol) of phthalimide potassium was added in portions to the solution, while the temperature of reaction solution was kept at 30° C. or lower. After addition, the mixture was stirred at room temperature for two hours, to complete the reaction. After reaction, the reaction solution was poured into 3,000 ml of water, allowing precipitation of the crystal. The crystal was filtered, washed with water and dried, to give 163 g of an intermediate 1 (yield: 84.9%).

Synthesis of Intermediate 2

56.2 g (0.66 mol) of cyanoacetic acid and 136 g (0.6 mol) of 2,6-di-tert-butyl-4-methylcyclohexanol were added to 400 ml of toluene, and the mixture was stirred at room temperature. 53.5 ml of pyridine was added dropwise to the solution. Then, 125 ml (0.132 mol) of acetic anhydride was added dropwise to the reaction solution, while the temperature was kept at 30° C. or lower. After dropwise addition, the mixture was stirred at room temperature 4 hours, to complete the reaction. The reaction solution was poured slowly into an aqueous solution of 110 g of sodium bicarbonate in 2,000 ml of water. The solution was then extracted with 1,200 ml of ethyl acetate. The ethyl acetate solution was washed with water and dried over anhydrous magnesium sulfate. The ethyl acetate solution was concentrated under reduced pressure; 400 ml of methanol was added to the residue; and the mixture was stirred, allowing precipitation of the crystal. 100 ml of water was added dropwise additionally at room temperature over 1 hour. The crystal was filtered, washed with a liquid mixture of methanol/water:4/1, and dried, to give 137 g of an intermediate 2 (yield: 77.8%).

Synthesis of Intermediate 3

102 g (0.5 mol) of the intermediate 1 and 147 g (0.5 mol) of the intermediate 2 thus obtained were mixed with 500 ml of ethanol, and the mixture was stirred while cooled to 5° C. to 10° C. 201 ml of SM-28 (28% sodium methoxide methanol solution) was added dropwise to the dispersion. The temperature of the reaction solution was kept to 10° C. or lower. After dropwise addition, the mixture was allowed to warm to room temperature and stirred additionally for 30 minutes, and then, after addition of 20 ml of water, stirred as heated under reflux additionally for 4 hours. After reaction, the reaction solution was cooled to room temperature, and 750 ml of water was added dropwise, allowing precipitation of the crystal. The crystal was filtered, washed with water and dried. The crystal was washed ad dispersed and stirred in 1,000 ml of n-hexane, filtered and dried, to give 143 g of an intermediate 3 (yield: 82.2%).

Synthesis of Intermediate 4

50 ml of acetic acid was added to 14.0 g (0.04 mol) of the intermediate 3 obtained by the method above, and the mixture was stirred at room temperature. 3.3 g (0.022 mol) of triethyl orthoformate was added to the solution dropwise. After dropwise addition, the mixture was stirred at room temperature for 12 hours. The precipitated crystal was filtered, washed with acetonitrile, and dried, to give 9.5 g of an intermediate 4 (yield: 67.2%).

The molar absorption coefficient ($\epsilon$) thereof in ethyl acetate solution at the maximum absorption wavelength ($\lambda max=531.7$ nm) was 65,400. The melting point was 236 to 238° C.

Synthesis of Exemplary Compound I-30

100 ml of ethyl acetate and 10 ml of methanol were added to 5.8 g (0.0082 mol) of the intermediate 4 obtained by the method above, and the mixture was stirred at room temperature. 0.9 g (0.0041 mol) of zinc acetate (II) was added to the solution. After addition, the mixture was stirred at room temperature for 8 hours, allowing precipitation of the crystal. 200 ml of water was added to the reaction solution, and the mixture was stirred at room temperature for 2 hours. The precipitated crystal was then filtered and washed with acetonitrile and finally with ethyl acetate, to give 4.8 g of an exemplary compound Ia-1 (yield: 79.2%).

The melting point was 300° C. or higher. The maximum absorption wavelength $\lambda max$ and the molar absorption coefficient $\epsilon$ of 1-30 in ethyl acetate solution were respectively 550.5 nm and 200,000.

Synthesis of Exemplary Compound I-31

50 ml of ethyl acetate and 50 ml of methanol were added to 7.07 g (0.01 mol) of the intermediate 4 obtained by the method above, and the mixture was stirred at room temperature. 0.91 g (0.005 mol) of copper acetate (II) was added to the solution. The mixture was stirred at 45° C. to 50° C. for 4 hours, and then allowed to cool to room temperature. 150 ml of water was added to the solution; the mixture was stirred for 1 hour; and the precipitated crystal was filtered and washed with water. The crystal was washed with acetonitrile and then with methanol and dried, to give 6.3 g of an exemplary compound Ia-2 (yield: 85.4%).

The melting point was 300° C. or higher. The maximum absorption wavelength $\lambda max$ and the molar absorption coefficient $\epsilon$ of 1-31 in ethyl acetate solution were respectively 548.9 nm and 156,200.

Synthesis of Exemplary Compounds I-32, I-33 and I-36

The following exemplary compounds were synthesized in a similar manner to I-30. The maximum absorption wavelength and the molar absorption coefficient thereof in ethyl acetate solution are shown below.

TABLE 1

| Exemplary compound | $\lambda_{max}$ | $\epsilon$ |
| --- | --- | --- |
| I-32 | 571.2 | 195800 |
| I-33 | 573.2 | 168000 |
| I-36 | 523.7 | 158000 |

Another method of synthesizing the particular metal complex compound of the invention will be described, by taking the exemplary compound III-1 as an example, along the following reaction scheme B.

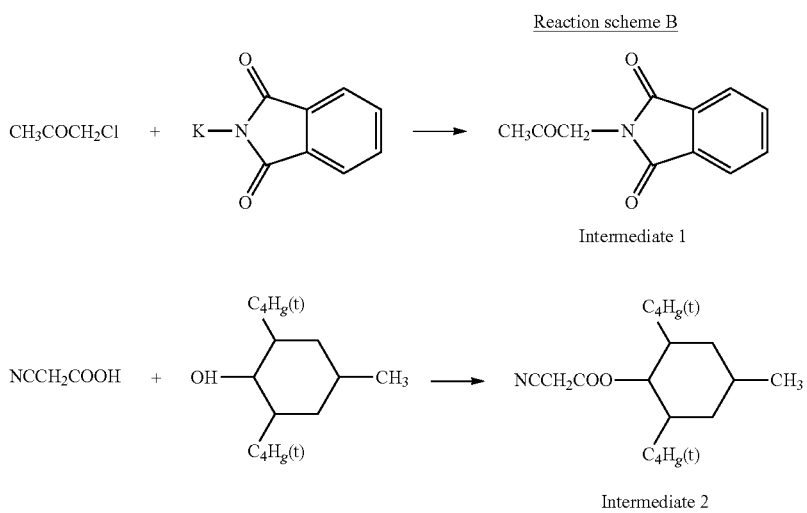

Reaction scheme B

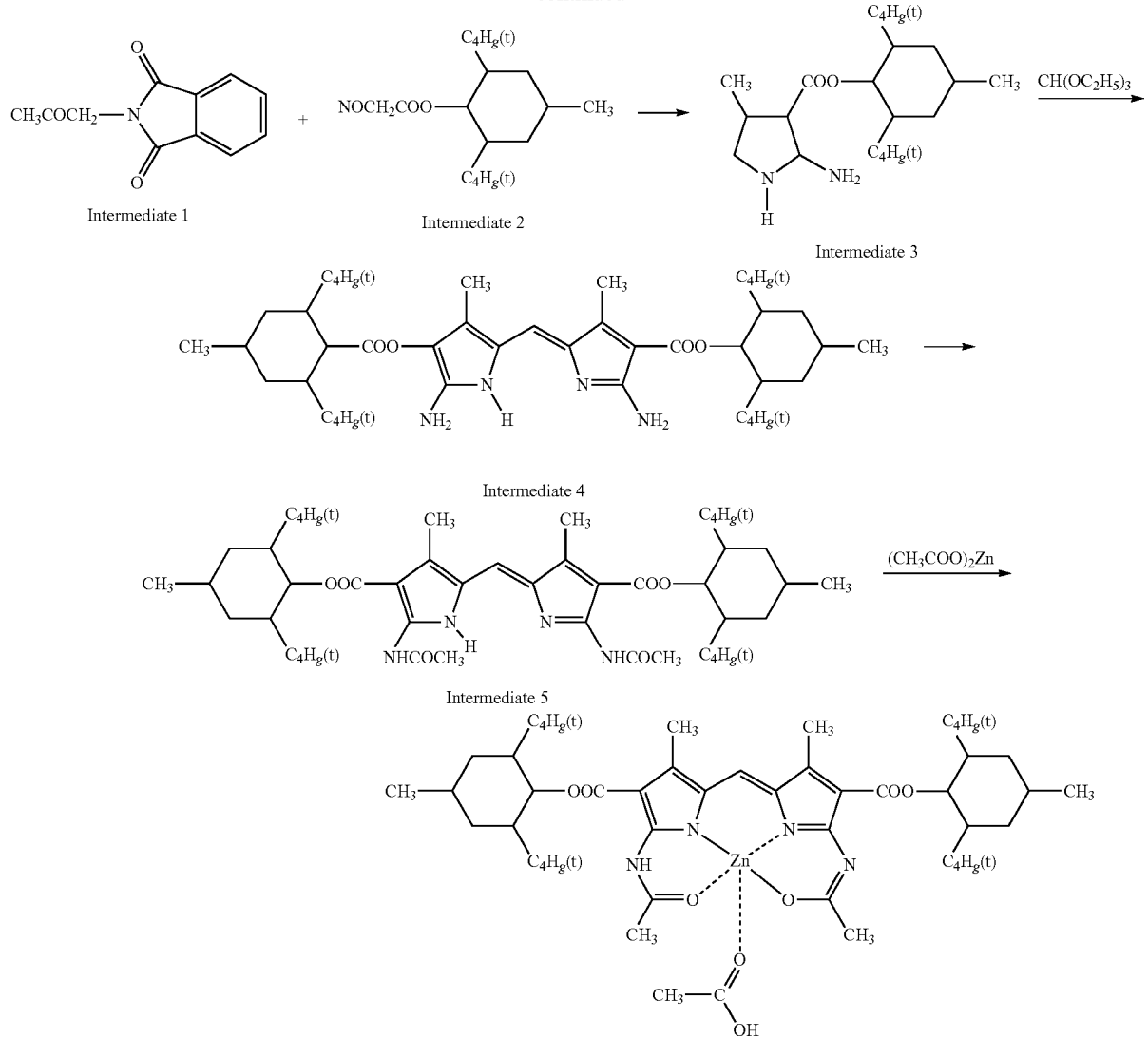

Exemplary compound III-1

Synthesis of Intermediate 5

31.0 (0.0438 mol) of the intermediate 4 obtained by the method above and 4.5 g (0.0438 mol) of dimethylaminopyridine were mixed with 200 ml of acetonitrile and 10 ml of N-methylpyrrolidone, and the mixture was stirred as heated under reflux. 10.5 ml of acetic anhydride was added dropwise to the solution, and the mixture was stirred as heated under reflux for 6 hours, to complete the reaction. After reaction, the mixture was cooled, and the precipitated crystal was filtered, washed with acetonitrile, and dried, to give 25.8 g of an intermediate 5 (yield: 74.4%). The maximum absorption wavelength λmax and the molar absorption coefficient E of the intermediate 5 in ethyl acetate solution were respectively 498.9 nm and 58,900.

Synthesis of Exemplary Compound III-1

250 ml of methanol was added to 15.8 g (0.02 mol) of the intermediate 5 obtained by the method above, and the mixture was stirred as room temperature. 5.49 g (0.025 mol) of zinc acetate dihydrate was added to the solution. After addition, the mixture was stirred at room temperature for 5 hours. The precipitated crystal was filtered, washed with methanol, and dried, to give 16.3 g of an exemplary compound III-1 (yield: 89.1%). The maximum absorption wavelength in ethyl acetate solution was 533.1 nm, and the molar absorption coefficient, 130,000.

$^1$HNMR (CDCl$_3$): 10.87 (s, 1H), 7.25 (s, 1H), 6.00 (s, 1H), 2.52 (s, 6H), 2.42 (s, 6H), 1.94 (s, 3H), 1.79 to 1.43 (br, 8H), 1.38 to 1.17 (m, 8H), 1.05 (d, 6H), and 0.96 to 0.74 (br, 36H)

Synthesis of Exemplary Compounds I-1, I-2, I-6, I-8, and III-45

The exemplary compounds I-1, I-2, I-6, I-8, and III-45 were synthesized according to the reaction scheme B, and the maximum absorption wavelength and the molar absorption coefficient thereof in ethyl acetate solution are shown below:

TABLE 2

| Exemplary compound | $\lambda_{max}$ | $\epsilon$ |
|---|---|---|
| I-1 | 558.2 | 129000 |
| I-2 | 578.3 | 122500 |
| I-6 | 536.6 | 104000 |
| I-8 | 524.0 | 78900 |
| III-45 | 546.7 | 128300 |

Synthesis of Exemplary Compound III-80

The compound III-80 was synthesized along the following reaction scheme C.

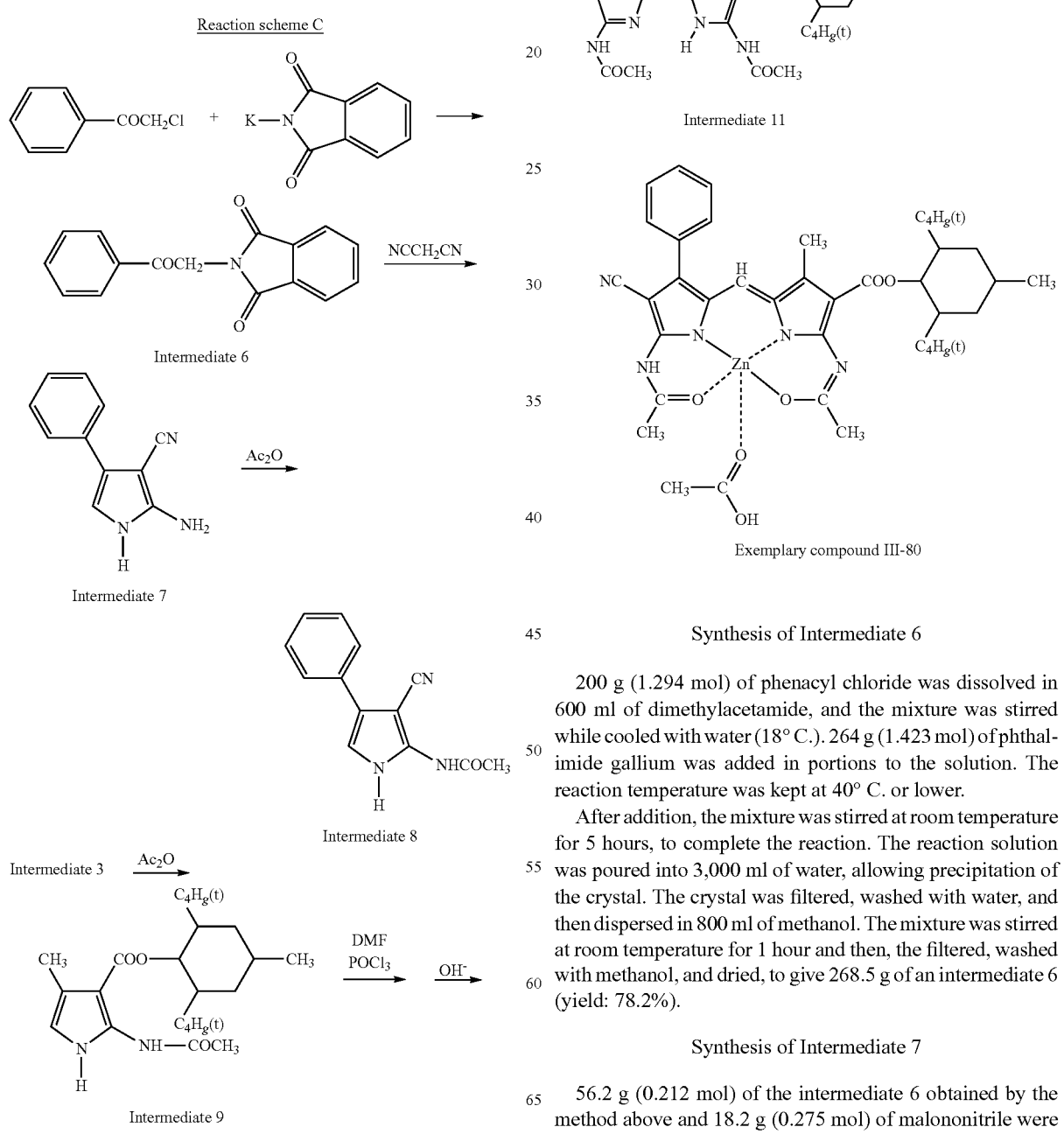

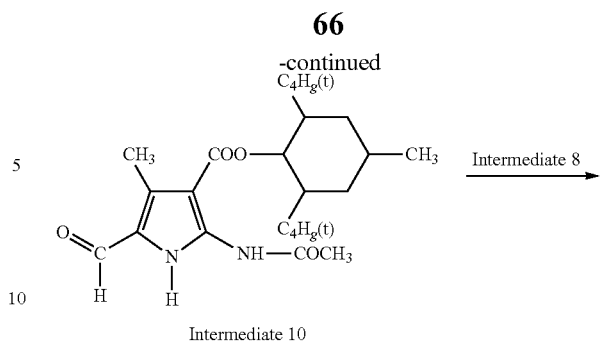

Synthesis of Intermediate 6

200 g (1.294 mol) of phenacyl chloride was dissolved in 600 ml of dimethylacetamide, and the mixture was stirred while cooled with water (18° C.). 264 g (1.423 mol) of phthalimide gallium was added in portions to the solution. The reaction temperature was kept at 40° C. or lower.

After addition, the mixture was stirred at room temperature for 5 hours, to complete the reaction. The reaction solution was poured into 3,000 ml of water, allowing precipitation of the crystal. The crystal was filtered, washed with water, and then dispersed in 800 ml of methanol. The mixture was stirred at room temperature for 1 hour and then, the filtered, washed with methanol, and dried, to give 268.5 g of an intermediate 6 (yield: 78.2%).

Synthesis of Intermediate 7

56.2 g (0.212 mol) of the intermediate 6 obtained by the method above and 18.2 g (0.275 mol) of malononitrile were added to 220 ml of methanol, and the mixture was stirred as cooled on ice (5° C.). 85.2 ml of 20% by mass sodium methoxide methanol solution (SM-28) was added to the solution dropwise. After dropwise addition, the mixture was stirred at 50 C. to 10° C. for 1 hour, additionally at room temperature for 1 hour, and then, as heated under reflux for 4 hours, to complete the reaction. After reaction, the reaction solution was poured into an aqueous solution of 10 ml of acetic acid and 1,500 ml of water while the mixture was stirred, allowing precipitation of the crystal. The crystal was filtered, washed with water, and dried, to give 28.5 g of an intermediate 7 (yield: 73.5%).

Synthesis of Intermediate 8

130 ml of acetonitrile was added to 26.0 g (0.142 mol) of the intermediate 7 obtained by the method above, and the mixture was stirred as heated under reflux. 16.1 ml of acetic anhydride was added to the solution dropwise. After dropwise addition, the mixture was stirred as heated under reflux for 5 hours, to complete the reaction. After reaction, the mixture was cooled to room temperature, and the precipitated crystal was filtered, washed with acetonitrile, and dried, to give 18.8 g of an intermediate 8 (yield: 58.8%).

Synthesis of Intermediate 9

41.7 g (0.12 mol) of the intermediate 3 obtained by the method of Synthesis Example-1 was mixed with 120 ml of acetonitrile, and the mixture was stirred at room temperature. 14.7 ml of acetic anhydride was added to the solution. After addition, the mixture was stirred as heated to 50° C. to 55° C. for 3 hours. After reaction, reaction solution was cooled to room temperature, and the precipitated crystal was filtered, washed with acetonitrile, and dried, to give 31.0 g of an intermediate 9 (yield: 66.1%).

Synthesis of Intermediate 10

60 ml of dimethylformamide was stirred while ice-cooled (5° C.). 14.4 ml of phosphorus oxychloride was added to the solution dropwise. After dropwise addition, the mixture was stirred at 5° C. for 30 minutes, and a solution of 30.6 g (0.0783 mol) of the intermediate 9 obtained by the method above dissolved in 30 ml of dimethylformamide was added thereto dropwise. After dropwise addition, the mixture was stirred at 5° C. to 10° C. for 1 hour, to complete the reaction.

After reaction, the reaction solution was poured into 250 ml of water dropwise while the mixture was stirred. An aqueous solution containing 30 g of sodium hydroxide dissolved in 120 ml of water was added to the aqueous solution dropwise, and the resulting mixture was stirred at room temperature for 30 minutes. The reaction solution was extracted with 300 ml of ethyl acetate. The ethyl acetate solution was washed with aqueous saturated sodium chloride solution and dried over anhydrous magnesium sulfate. The ethyl acetate solution was concentrated under reduced pressure, and 120 ml of acetonitrile was added to the residue, allowing precipitation of the crystal. The crystal was filtered, washed with acetonitrile, and dried, to give 20.5 g of an intermediate 10 (yield: 62.5%).

Synthesis of Intermediate 11

18.8 g (0.05 mol) of the intermediate 10 obtained by the method above was mixed with 60 ml of acetic anhydride, and the mixture was stirred as room temperature. A solution of 11.3 g (0.05 mol) of the intermediate 8 dissolved in a mixed solvent of 3.0 ml of trifluoroacetic acid and 60 ml of acetic acid was added dropwise to the solution. After addition, the solution was stirred at room temperature for 2 hours, to complete the reaction. After reaction, the reaction solution was poured into 800 ml of water, while the mixture was stirred. The precipitated crystal was filtered, washed with water, and dried, to give 22.5 g of an intermediate 11 (yield: 71.9%).

Synthesis of Exemplary Compound III-80

2.2 g (0.01 mol) of zinc acetate dihydrate was dissolved in 200 ml of methanol, and the mixture was stirred at room temperature. 6.26 g (0.01 mol) of the intermediate 11 obtained by the method above was added in portions to the solution. After addition, the mixture was stirred at room temperature for 5 hours, allowing complexation. After reaction, the precipitated crystal was filtered, washed with methanol, and dried, to give 6.48 g of an exemplary compound III-80 (yield 86.5%).

The maximum absorption wavelength λmax and the molar absorption coefficient £ of 111-80 in ethyl acetate solution were respectively 540.0 nm and 123,000.

Synthesis of Exemplary Compounds II-5, II-4, I-4, and III-70

The following exemplary compounds were synthesized in a similar manner to the reaction scheme C. The properties of the ethyl acetate solutions are described below.

TABLE 3

| Exemplary compound | $\lambda_{max}$ | $\epsilon$ |
|---|---|---|
| II-5 | 514.6 | 80700 |
| II-4 | 518.9 | 85000 |
| I-4 | 540.0 | 114000 |
| III-70 | 540.0 | 126000 |

The particular metal complex compounds I to IV may be used alone or in combination of two or more kinds as the colored photosensitive curing composition of the invention.

The content of any one of the particular metal complex compounds I to IV of the invention in the UV-sensitive-colored curing composition may vary according to the molecular weight and the molar absorption coefficient thereof, but preferably 0.5 to 80% by mass, more preferably 0.5 to 60% by mass, and most preferably 0.5 to 50% by mass, with respect to the total solid content in the UV-sensitive colored curing composition.

<Tetraazaporphyrin-Based Cyan Colorant Represented by Formula (A)>

It is possible to prepare a color filter of the colored photosensitive curing composition superior in color purity and rigidity, by using the colored photosensitive curing composition of the invention containing a particular metal complex compound I (including the particular metal complex compound II), a particular boron complex compound, and a tetraazaporphyrin-based cyan colorant represented by the following Formula (A) (hereinafter, suitably referred to as "particular colorant A"), such a color filter is used particularly favorably in charge coupled devices (CCDs) and CMOSs.

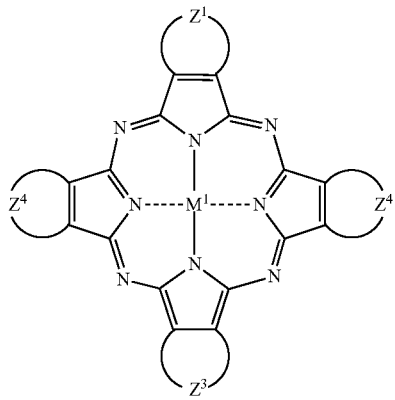

Formula (A)

In Formula (A), $M^1$ represents a metal or a metal compound; and $Z^1$, $Z^2$, $Z^3$, and $Z^4$ each independently represent an atom group forming a six-membered ring with atoms selected from carbon, nitrogen, and hydrogen atoms.

The metal or metal compound is not particularly limited, if it is a metal or metal compound capable of forming a complex, and examples thereof include bivalent metal atoms, bivalent metal oxides, bivalent metal hydroxides, and bivalent metal chlorides.

Examples of $M^1$ in Formula (A) include metals such as Zn, Mg, Si, Sn, Rh, Pt, Pd, Mo, Mn, Pb, Cu, Ni, Co, and Fe, metal chlorides such as AlCl, InCl, FeCl, $TiCl_2$, $SnCl_2$, $SiCl_2$, and $GeCl_2$, metal oxides such as TiO and VO; and metal hydroxides such as $Si(OH)_2$.

In Formula (A), $Z^1$, $Z^2$, $Z^3$, and $Z^4$ each independently represent an atom group needed for forming a six-membered ring with atoms selected from carbon, nitrogen, and hydrogen atoms. The six-membered ring may be a saturated or unsaturated ring and may be unsubstituted or substituted. It may be fused with another five- or six-membered ring additionally. Examples of the six-membered rings include benzene, cyclohexane, pyridine, pyrimidine, pyrazine, and other rings.

The maximum absorption wavelength λmax of the particular colorant A of the invention is preferably 580 nm to 700 nm, more preferably 600 nm to 680 nm, from the viewpoint of improvement in color purity. The maximum absorption wavelength thereof was determined similarly to the particular metal complex compound I.

<Phthalocyanine-Based Colorant Represented by the Following Formula (B)>

Among the tetraazaporphyrin-based colorants represented by the Formula (A), the phthalocyanine colorants represented by the following Formula (B) (hereinafter, suitably referred to as "particular colorant B") are particularly preferable.

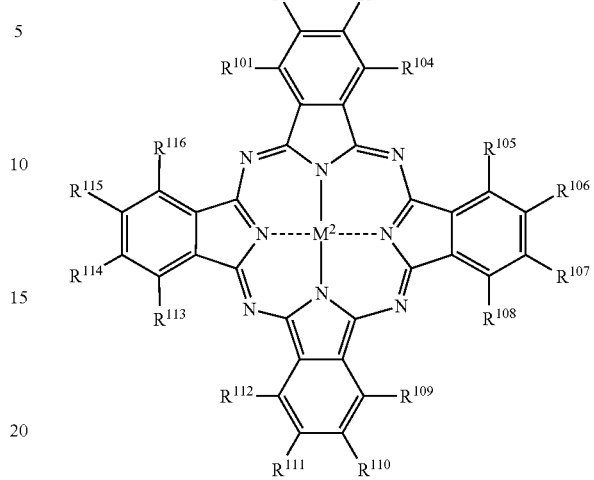

Formula (B)

In Formula (B), $R^{101}$ to $R^{116}$ each independently represent a hydrogen atom or a substituent group; and $M^2$ represents a metal or metal compound.

In Formula (B), $M^2$ is the same as $M^1$ in the compound represented by Formula (A), and the preferable examples thereof are also the same.

$R^{101}$ to $R^{116}$ each independently represent a hydrogen atom or a substituent group; the substituent group represented by $R^{101}$ to $R^{116}$ is the same as those for $R^1$ to $R^6$ in Formula (I); and the preferable examples thereof are also the same. The substituent group of $R^{101}$ to $R^{116}$ in the compound represented by Formula (B) is a group that may be substituted additionally, and it may be substituted with one or more substituent groups for $R^1$ to $R^6$; and when two or more substituent groups are substituted, the substituent groups may be the same as or different from each other.

Hereinafter, examples of the substituent groups $R^{101}$ to $R^{116}$ in the particular colorant B are listed below (T-1 to T141). However, the invention is not limited to thereto.

| | |
|---|---|
| —F | T-1 |
| —Cl | T-2 |
| —Br | T-3 |
| —CH₃ | T-4 |
| —C₄H₉(t) | T-5 |
| —CF₃ | T-6 |
| —CN | T-7 |
| —NO₂ | T-8 |
| —COONa | T-9 |
| —CONH₂ | T-10 |
| —N(pyrazolyl) | T-11 |

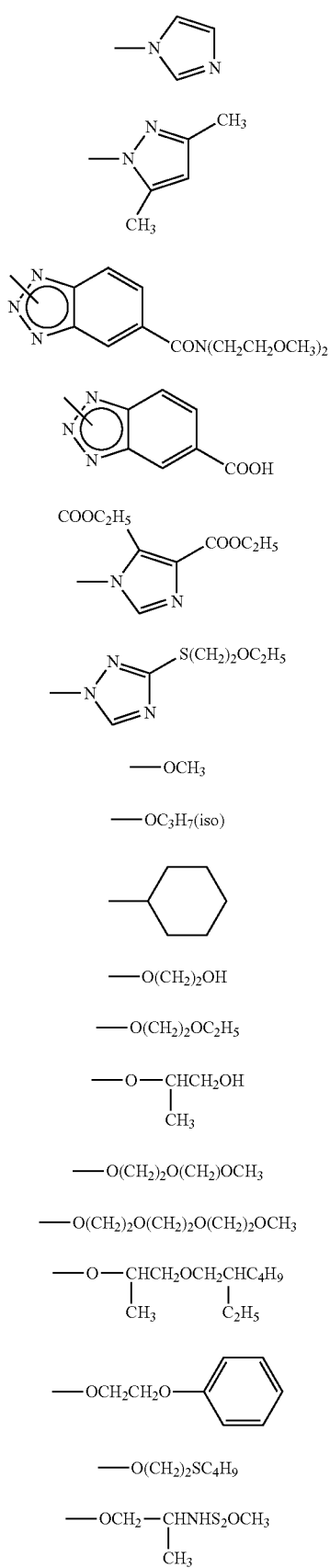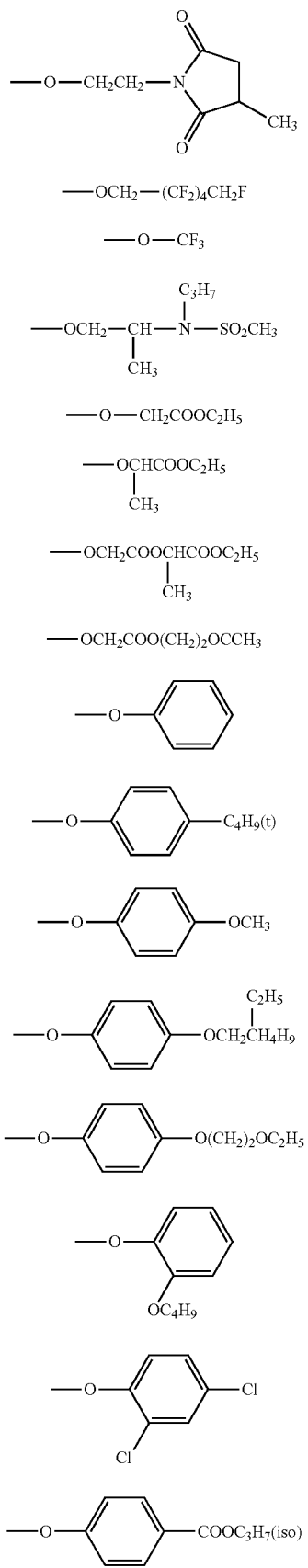

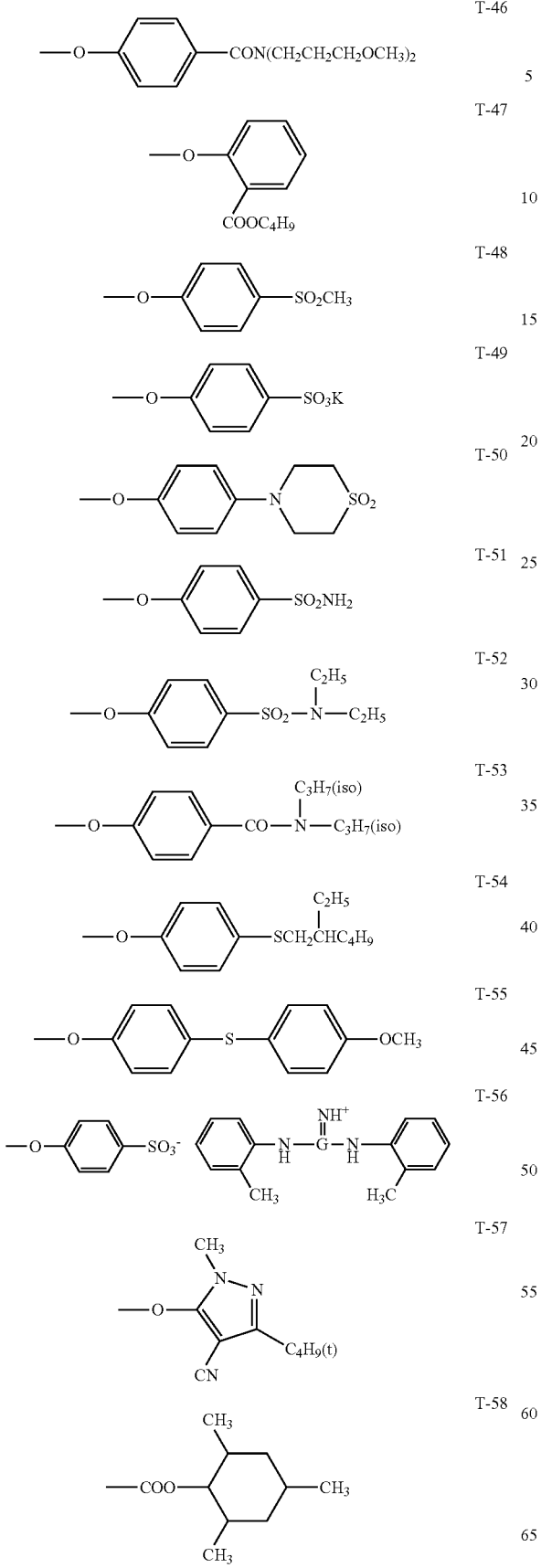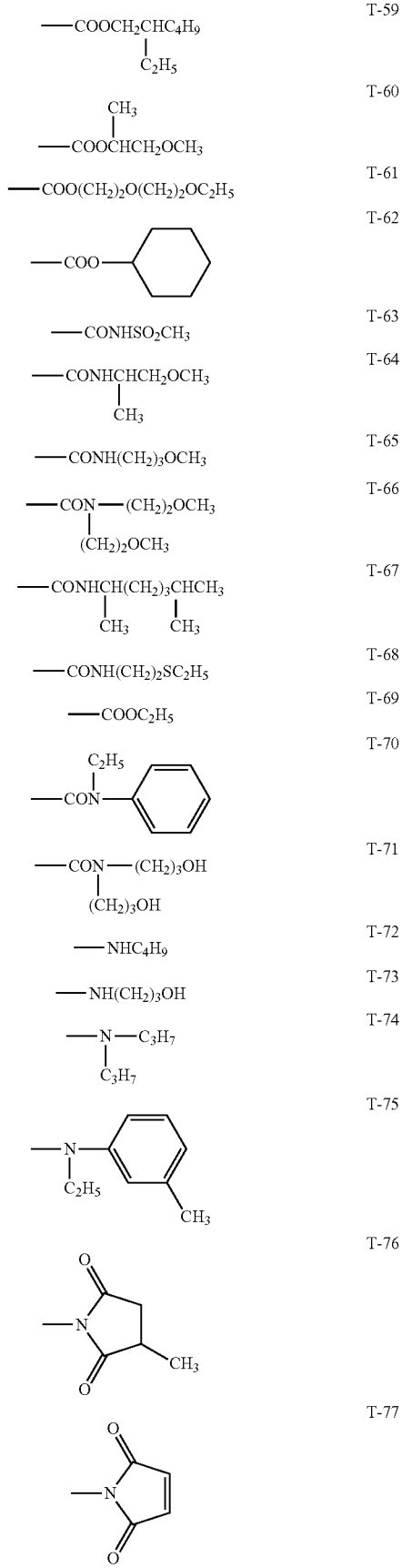

-continued

T-78: 3-methylene-1-methylpyrrolidine-2,5-dione (N-methyl with =CH$_2$ group)

T-79: 4-methylmorpholine-3,5-dione (N-methyl morpholinedione)

T-80: —NHSO$_2$CH$_3$

T-81: —N(SO$_2$CH$_3$)(CH$_2$)$_2$O(CH$_2$)$_2$OCH$_3$

T-82: —SCH$_3$

T-83: —S—C$_6$H$_5$ (phenylthio)

T-84: —SO$_2$CH$_3$

T-85: —SO$_2$(CH$_2$)$_2$OC$_2$H$_5$

T-86: —SO$_2$(CH$_2$)$_2$O(CH$_2$)$_2$OCH$_3$

T-87: —SO$_2$(CH$_2$)$_3$CONH(CH$_2$)$_3$OC$_2$H$_5$

T-88: —SO$_2$CH$_2$CH$_2$CH$_2$SO$_3$Na

T-89: —SO$_2$(CH$_2$)$_3$SO$_2$N(CH$_2$CH$_2$CH$_2$OCH$_3$)$_2$

T-90: —SO$_2$CH$_2$—CH(C$_2$H$_5$)C$_4$H$_9$

T-91: —SO$_2$(CH$_2$)$_2$O(CH$_2$)$_2$O(CH$_2$)$_2$OCH$_3$

T-92: —SO$_2$(CH$_2$)$_3$COOH

T-93: —SO$_2$(CH$_2$)$_3$COOCH$_5$

T-94: —SO$_2$(CH$_2$)$_2$COOCH$_2$CH(C$_2$H$_5$)C$_4$H$_9$

T-95: —SO$_2$(CH$_2$)$_3$SO$_2$NH—CH(CH$_3$)CH$_2$OCH$_3$

T-96: —SO$_2$(CH$_2$)$_3$SO$_2$NH(CH$_2$)$_3$OC$_4$H$_9$

T-97: —SO$_2$(CH$_2$)$_3$SO$_2$NH(CH$_2$)$_3$OC$_2$H$_5$

T-98: —SO$_2$—CH(CH$_3$)CON(CH$_2$CH$_2$OC$_3$H$_7$)$_2$

T-99: —SO$_2$—NHCOCH$_3$

T-100: —CONHSO$_2$CH$_3$

T-101: —SO$_2$—cyclohexyl

T-102: —SO$_2$—CH$_2$CH$_2$COOC$_2$H$_5$

T-103: —SO$_2$CH(CH$_3$)OOC$_4$H$_9$

T-104: —SO$_2$CH(C$_4$H$_9$)COOCH(CH$_3$)

T-105: —SO$_2$CH(C$_4$H$_9$)CON(C$_2$H$_5$)

T-106: —SO$_2$CH$_2$CH(OH)CH$_2$OH

T-107: —SO$_2$—C$_6$H$_5$ (phenyl)

T-108: —SO$_2$—C$_6$H$_4$—CH$_3$ (4-methylphenyl)

T-109: —SO$_2$—C$_6$H$_4$—OCH$_3$ (4-methoxyphenyl)

T-110: —SO$_2$—C$_6$H$_4$—SO$_3$K (3-sulfonato-K-phenyl)

T-111: —SO$_2$—C$_6$H$_4$—COOH (2-carboxyphenyl)

T-112: —SO$_2$—C$_6$H$_4$—COOH (4-carboxyphenyl)

T-113: —SO$_2$—2,4,6-trimethylphenyl (mesityl)

T-114: —SO$_2$—C$_6$H$_4$—CONHSO$_2$CH$_3$

T-115: —SO$_2$—C$_6$H$_4$—CONH(CH$_2$)$_3$OC$_2$H$_5$

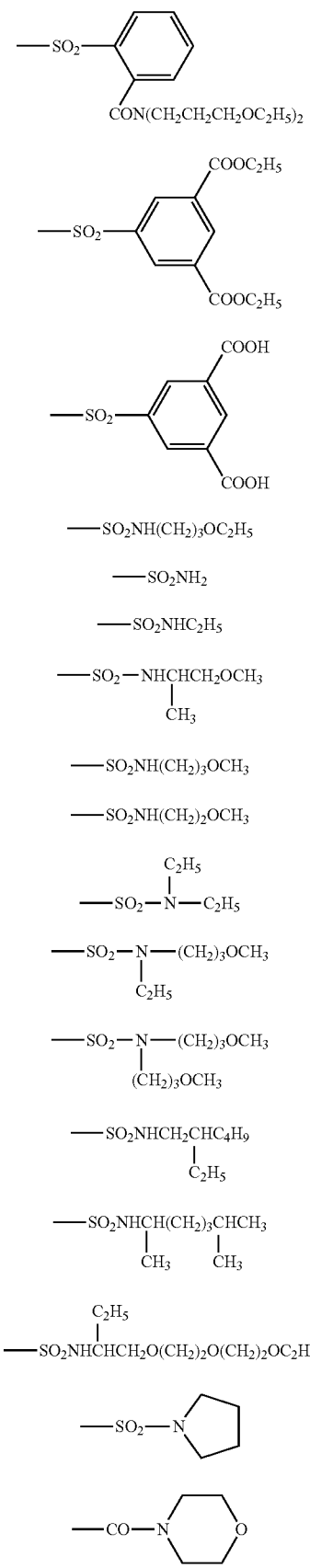

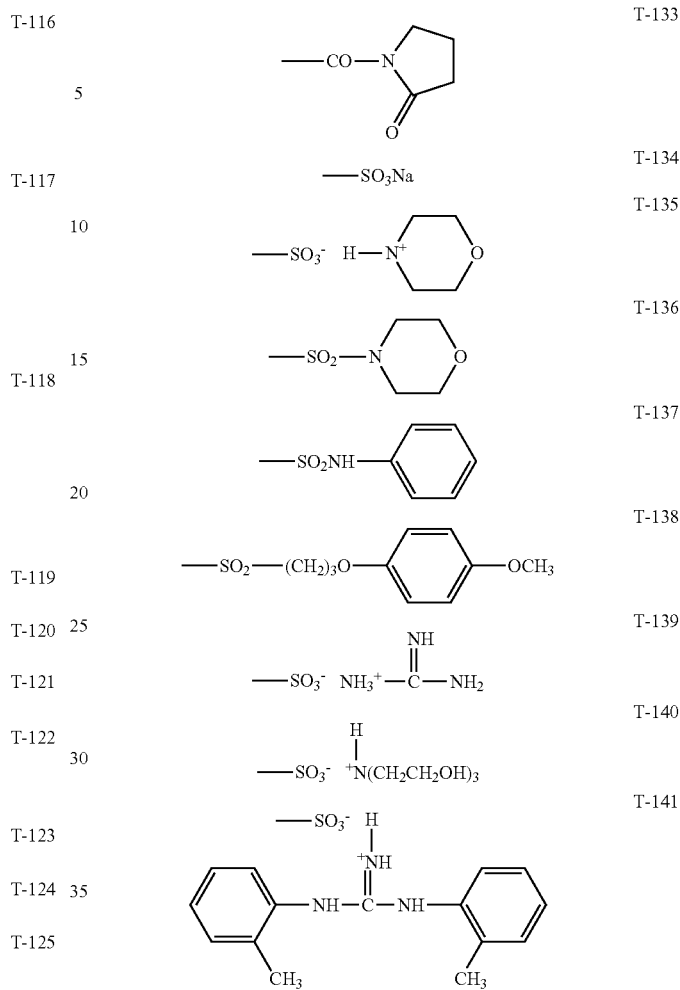

Preferable examples of the phthalocyanine colorants represented by Formula (B) will be described below.

The phthalocyanine colorants represented by the Formula (B) are α-site substituted derivatives (α-substituted derivatives) having substituent groups in at least one combination of ($R^{101}$ and $R^{104}$), ($R^{105}$ and $R^{108}$), ($R^{109}$ and $R^{112}$), and ($R^{113}$ and $R^{116}$); β-site substituted derivatives (β-substituted derivatives) having substituent groups in at least one combination of ($R^{102}$ and $R^{103}$), ($R^{106}$ and $R^{107}$), ($R^{110}$ and $R^{111}$), ($R^{114}$ and $R^{115}$); α- and β-substituted derivatives having substituent groups in at least one combination of ($R^{101}$ and $R^{103}$ and/or $R^{102}$ and $R^{104}$), ($R^{105}$ and $R^{107}$ and/or $R^{106}$ and $R^{108}$), ($R^{109}$ and $R^{111}$ and/or $R^{110}$ and $R^{112}$), and ($R^{113}$ and $R^{115}$ and/or $R^{114}$ and $R^{116}$).

Examples of the substituent groups represented by $R^{101}$ to $R^{116}$ above include halogen atoms and alkyl, alkenyl, aryl, heterocyclic, silyl, hydroxyl, carboxyl, cyano, nitro, alkoxy, aryloxy, heterocyclic oxy, silyloxy, acyloxy, alkoxycarbonyloxy, aryloxycarbonyloxy, carbamoyloxy, sulfamoyloxy, alkylsulfonyloxy, arylsulfonyloxy, acyl, alkoxycarbonyl, aryloxycarbonyl, carbamoyl, amino, anilino, carbonamido, ureido, imido, alkoxycarbonylamino, aryloxycarbonylamino, sulfonamido, sulfamoylamino, azo, alkylthio, arylthio, heterocyclic thio, alkylsulfinyl, arylsulfinyl, alkylsulfonyl, arylsulfonyl, sulfamoyl, sulfo, sulfonyl, and phosphinoylamino groups. $M^2$ is, for example, Zn, Mg, Si, Sn, Rh, Pt, Pd, Mo, Mn, Pb, Cu, Ni, Co, Fe, TiO, or VO.

Preferable examples of the phthalocyanine colorants represented by the Formula (B) include α-substituted derivatives (monosubstituted derivatives) having a substituent group as at least one of ($R^{101}$ or $R^{104}$), ($R^{105}$ or $R^{108}$), ($R^{109}$ or $R^{112}$), and ($R^{113}$ or $R^{116}$); and β substituted derivatives (monosubstituted derivatives) having a substituent group a at least one of ($R^{102}$ or $R^{103}$), ($R^{106}$ or $R^{107}$), ($R^{110}$ or $R^{111}$), and ($R^{114}$ or $R^{115}$).

Examples of the substituent groups represented by $R^{101}$ to $R^{116}$ above include halogen atoms and alkyl, alkenyl, aryl, heterocyclic, silyl, hydroxyl, carboxyl, cyano, nitro, alkoxy, aryloxy, heterocyclic oxy, acyloxy, carbamoyloxy, acyl, alkoxycarbonyl, aryloxycarbonyl, carbamoyl, amino, anilino, carbonamido, ureido, imido, alkoxycarbonylamino, aryloxycarbonylamino, sulfonamido, sulfamoylamino, azo, alkylthio, arylthio, heterocyclic thio, alkylsulfinyl, arylsulfinyl, alkylsulfonyl, arylsulfonyl, sulfamoyl, sulfo, and phosphinoylamino groups. $M^2$ is, for example, Zn, Pd, Cu, Ni, Co, TiO, or VO.

More preferable examples of the phthalocyanine colorants represented by the Formula (B) include α-substituted derivatives having substituents as at least three of ($R^{101}$ or $R^{104}$), ($R^{105}$ or $R^{108}$), ($R^{109}$ or $R^{112}$), and ($R^{113}$ or $R^{116}$); and β-substituted derivatives having substituents as at least three of ($R^{102}$ or $R^{103}$), ($R^{106}$ or $R^{107}$), ($R^{110}$ or $R^{111}$), and ($R^{114}$ or $R^{115}$).

Examples of the substituent groups represented by $R^{101}$ to $R^{116}$ above include halogen atoms and alkyl, alkenyl, aryl, heterocyclic, hydroxyl, carboxyl, cyano, nitro, alkoxy, aryloxy, heterocyclic oxy, acyl group. alkoxycarbonyl, carbamoyl, amino, anilino, carbonamido, ureido, imido, alkoxycarbonylamino, aryloxycarbonylamino, sulfonamido, sulfamoylamino, azo, alkylsulfinyl, arylsulfinyl, alkylsulfonyl, arylsulfonyl, sulfamoyl, and sulfo groups. $M^1$ is, for example, Zn, Pd, Cu, Ni, Co, or VO.

Still more preferable examples of the phthalocyanine colorants represented by the Formula (B) include α-substituted derivatives having the same substituents as at least three of ($R^{101}$ or $R^{104}$), ($R^{105}$ or $R^{108}$), ($R^{109}$ or $R^{112}$), and ($R^{113}$ or $R^{116}$); and β-substituted derivatives having the same substituents as at least three of ($R^{102}$ or $R^{103}$), ($R^{106}$ or $R^{107}$), ($R^{110}$ or $R^{111}$), and ($R^{114}$ or $R^{115}$).

Examples of the substituent groups represented by $R^{101}$ to $R^{116}$ above include halogen atoms and alkyl, alkenyl, aryl, heterocyclic, carboxyl, cyano, alkoxy, aryloxy, heterocyclic oxy, acyl, alkoxycarbonyl, carbamoyl, carbonamido, ureido, imido, sulfonamido, alkylsulfinyl, arylsulfinyl, alkylsulfonyl, arylsulfonyl, sulfamoyl, and sulfo groups. $M^2$ is, for example, Zn, Pd, Cu, Ni, Co, or VO.

Particularly preferable examples of the phthalocyanine colorants represented by the Formula (B) include α-substituted derivatives having substituents as at least three of ($R^{101}$ or $R^{104}$), ($R^{105}$ or $R^{108}$), ($R^{109}$ or $R^{112}$), and ($R^{113}$ or $R^{116}$) and β-substituted derivatives having substituents as at least three of ($R^{102}$ or $R^{103}$), ($R^{106}$ or $R^{107}$), ($R^{110}$ or $R^{111}$), and ($R^{114}$ or $R^{115}$), wherein all of the substituent groups are the same as each other.

Examples of the substituent groups represented by $R^{101}$ to $R^{116}$ above include halogen atoms and alkyl, heterocyclic, carboxyl, cyano, alkoxy, aryloxy, heterocyclic oxy, alkoxycarbonyl, carbamoyl, alkylsulfonyl, arylsulfonyl, sulfamoyl, and sulfo groups. $M^2$ is, for example, Zn, Pd, Cu, Ni, Co, or VO.

The most preferable examples of the phthalocyanine colorants represented by the Formula (B) include α-substituted derivatives having substituents as at least three of ($R^{101}$ or $R^{104}$), ($R^{105}$ or $R^{108}$), ($R^{109}$ or $R^{112}$) and ($R^{113}$ or $R^{116}$) and β-substituted derivatives having substituents as at least three of ($R^{102}$ or $R^{103}$), ($R^{106}$ or $R^{107}$), ($R^{110}$ or $R^{111}$), and ($R^{114}$ or $R^{115}$), wherein all of the substituent groups are the same as each other, and examples of the substituent groups of $R^{101}$ to $R^{116}$ include halogen atoms and alkyl, heterocyclic, carboxyl, alkoxy, aryloxy, heterocyclic oxy, alkoxycarbonyl, carbamoyl, alkylsulfonyl, arylsulfonyl, sulfamoyl, and sulfo groups. $M^2$ is, for example, Zn, Cu, Co, or VO.

Hereinafter, specific examples of the tetraazaporphyrin-based colorants represented by Formula (A) (including phthalocyanine-based colorants represented by Formula (B)) are shown below (exemplary compounds CA-1 to CA-46, CB-1 to CB-46, CC-1 to CC-10, CK-1 to CK-19, CE-1 to CE-46, CF-1 to CF-46, CG-1 to CG-46, CI-1 to CI-46, and CH-1 to CH-46). However, the specific examples are not limited thereto in the invention.

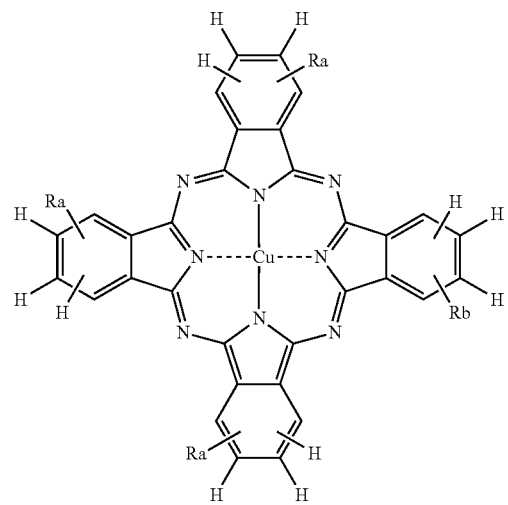

| Exemplary Compound | Ra | Rb | Exemplary Compound | Ra | Rb |
|---|---|---|---|---|---|
| CA-1 | T-14 | T-14 | CA-2 | T-14 | T-15 |
| CA-3 | T-14 | T-88 | CA-4 | T-14 | T-99 |
| CA-5 | T-14 | T-141 | CA-6 | T-46 | T-46 |
| CA-7 | T-46 | T-49 | CA-8 | T-46 | T-56 |
| CA-9 | T-89 | T-89 | CA-10 | T-89 | T-88 |
| CA-11 | T-89 | T-99 | CA-12 | T-89 | T-141 |
| CA-13 | T-95 | T-95 | CA-14 | T-95 | T-88 |
| CA-15 | T-95 | T-112 | CA-16 | T-95 | T-15 |
| CA-17 | T-95 | T-114 | CA-18 | T-95 | T-134 |
| CA-19 | T-95 | T-141 | CA-20 | T-96 | T-96 |
| CA-21 | T-96 | T-88 | CA-22 | T-96 | T-99 |
| CA-23 | T-96 | T-112 | CA-24 | T-96 | T-134 |
| CA-25 | T-96 | T-135 | CA-26 | T-96 | T-141 |
| CA-27 | T-97 | T-97 | CA-28 | T-97 | T-15 |
| CA-29 | T-97 | T-88 | CA-30 | T-97 | T-99 |
| CA-31 | T-97 | T-112 | CA-32 | T-97 | T-120 |
| CA-33 | T-97 | T-134 | CA-34 | T-97 | T-141 |
| CA-35 | T-115 | T-115 | CA-36 | T-115 | T-112 |
| CA-37 | T-115 | T-118 | CA-38 | T-115 | T-134 |
| CA-39 | T-115 | T-141 | CA-40 | T-116 | T-116 |
| CA-41 | T-116 | T-112 | CA-42 | T-116 | T-134 |
| CA-43 | T-116 | T-141 | CA-44 | T-130 | T-130 |
| CA-45 | T-130 | T-134 | CA-46 | T-130 | T-141 |

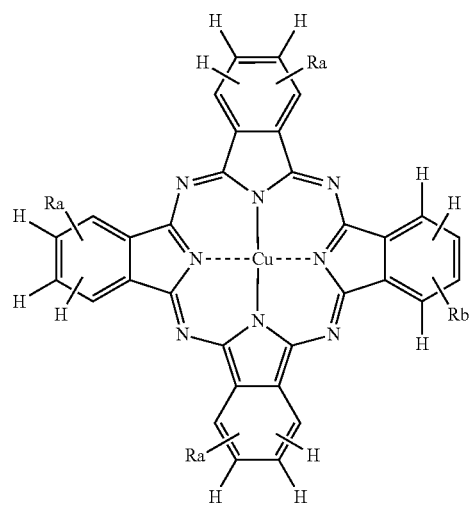

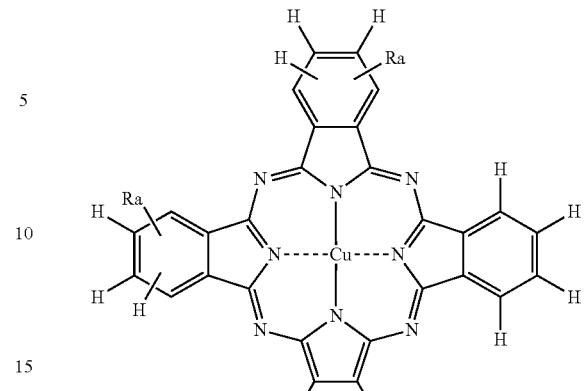

| Exemplary Compound | Ra | Rb | Exemplary Compound | Ra | Rb |
| --- | --- | --- | --- | --- | --- |
| CB-1 | T-14 | T-14 | CB-2 | T-14 | T-15 |
| CB-3 | T-14 | T-88 | CB-4 | T-14 | T-99 |
| CB-5 | T-14 | T-141 | CB-6 | T-46 | T-46 |
| CB-7 | T-46 | T-49 | CB-8 | T-46 | T-56 |
| CB-9 | T-89 | T-89 | CB-10 | T-89 | T-88 |
| CB-11 | T-89 | T-99 | CB-12 | T-89 | T-141 |
| CB-13 | T-95 | T-95 | CB-14 | T-95 | T-88 |
| CB-15 | T-95 | T-112 | CB-16 | T-95 | T-15 |
| CB-17 | T-95 | T-114 | CB-18 | T-95 | T-134 |
| CB-19 | T-95 | T-141 | CB-20 | T-96 | T-96 |
| CB-21 | T-96 | T-88 | CB-22 | T-96 | T-99 |
| CB-23 | T-96 | T-112 | CB-24 | T-96 | T-134 |
| CB-25 | T-96 | T-135 | CB-26 | T-96 | T-141 |
| CB-27 | T-97 | T-97 | CB-28 | T-97 | T-15 |
| CB-29 | T-97 | T-88 | CB-30 | T-97 | T-99 |
| CB-31 | T-97 | T-112 | CB-32 | T-97 | T-120 |
| CB-33 | T-97 | T-134 | CB-34 | T-97 | T-141 |
| CB-35 | T-115 | T-115 | CB-36 | T-115 | T-112 |
| CB-37 | T-115 | T-118 | CB-38 | T-115 | T-134 |
| CB-39 | T-115 | T-141 | CB-40 | T-116 | T-116 |
| CB-41 | T-116 | T-112 | CB-42 | T-116 | T-134 |
| CB-43 | T-116 | T-141 | CB-44 | T-130 | T-130 |
| CB-45 | T-130 | T-134 | CB-46 | T-130 | T-141 |

| Exemplary Compound | Ra | Exemplary Compound | Ra | Exemplary Compound | Ra |
| --- | --- | --- | --- | --- | --- |
| CC-1 | T-14 | CC-2 | T-46 | CC-3 | T-89 |
| CC-4 | T-89 | CC-5 | T-95 | CC-6 | T-96 |
| CC-7 | T-97 | CC-8 | T-115 | CC-9 | T-116 |
| CC-10 | T-130 | — | — | — | — |

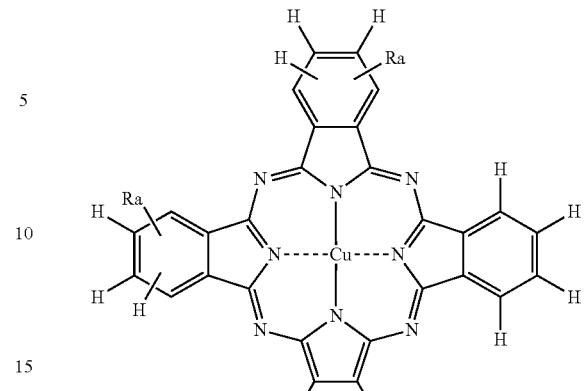

| Exemplary Compound | Ra | Rb | Ma |
| --- | --- | --- | --- |
| CK-1 | T-14 | T-15 | Zn |
| CK-2 | T-14 | T-15 | Co |
| CK-3 | T-14 | T-15 | V=O |
| CK-4 | T-14 | T-15 | Pd |
| CK-5 | T-14 | T-134 | Zn |
| CK-6 | T-14 | T-134 | Co |
| CK-7 | T-14 | T-141 | Zn |
| CK-8 | T-46 | T-112 | Zn |
| CK-9 | T-46 | T-134 | V=O |
| CK-10 | T-46 | T-141 | V=O |
| CK-11 | T-95 | T-112 | Zn |
| CK-12 | T-96 | T-88 | Zn |
| CK-13 | T-96 | T-112 | Co |
| CK-14 | T-96 | T-134 | V=O |
| CK-15 | T-96 | T-141 | Pd |
| CK-16 | T-130 | T-134 | Zn |
| CK-17 | T-130 | T-134 | Fe |
| CK-18 | T-130 | T-141 | Ni |
| CK-19 | T-130 | T-141 | Ti |

| | | | | | | | | | | |
|---|---|---|---|---|---|---|---|---|---|---|
| 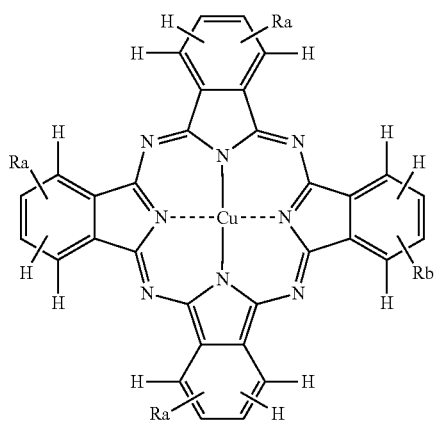 | | | | | | 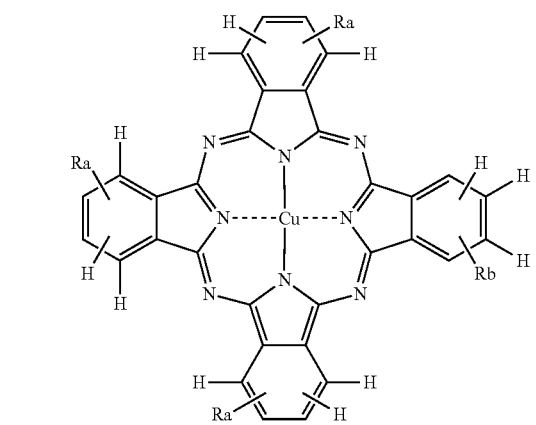 | | | | |
| Exemplary Compound | Ra | Rb | Exemplary Compound | Ra | Rb | Exemplary Compound | Ra | Rb | Exemplary Compound | Ra | Rb |

| Exemplary Compound | Ra | Rb | Exemplary Compound | Ra | Rb | Exemplary Compound | Ra | Rb | Exemplary Compound | Ra | Rb |
|---|---|---|---|---|---|---|---|---|---|---|---|
| CE-1 | T-14 | T-14 | CE-2 | T-14 | T-15 | CF-1 | T-14 | T-14 | CF-2 | T-14 | T-15 |
| CE-3 | T-14 | T-88 | CE-4 | T-14 | T-99 | CF-3 | T-14 | T-88 | CF-4 | T-14 | T-99 |
| CE-5 | T-14 | T-141 | CE-6 | T-46 | T-46 | CF-5 | T-14 | T-141 | CF-6 | T-46 | T-46 |
| CE-7 | T-46 | T-49 | CE-8 | T-46 | T-56 | CF-7 | T-46 | T-49 | CF-8 | T-46 | T-56 |
| CE-9 | T-89 | T-89 | CE-10 | T-89 | T-88 | CF-9 | T-89 | T-89 | CF-10 | T-89 | T-88 |
| CE-11 | T-89 | T-99 | CE-12 | T-89 | T-141 | CF-11 | T-89 | T-99 | CF-12 | T-89 | T-141 |
| CE-13 | T-95 | T-95 | CE-14 | T-95 | T-88 | CF-13 | T-95 | T-95 | CF-14 | T-95 | T-88 |
| CE-15 | T-95 | T-112 | CE-16 | T-95 | T-15 | CF-15 | T-95 | T-112 | CF-16 | T-95 | T-15 |
| CE-17 | T-95 | T-114 | CE-18 | T-95 | T-134 | CF-17 | T-95 | T-114 | CF-18 | T-95 | T-134 |
| CE-19 | T-95 | T-141 | CE-20 | T-96 | T-96 | CF-19 | T-95 | T-141 | CF-20 | T-96 | T-96 |
| CE-21 | T-96 | T-88 | CE-22 | T-96 | T-99 | CF-21 | T-96 | T-88 | CF-22 | T-96 | T-99 |
| CE-23 | T-96 | T-112 | CE-24 | T-96 | T-134 | CF-23 | T-96 | T-112 | CF-24 | T-96 | T-134 |
| CE-25 | T-96 | T-135 | CE-26 | T-96 | T-141 | CF-25 | T-96 | T-135 | CF-26 | T-96 | T-141 |
| CE-27 | T-97 | T-97 | CE-28 | T-97 | T-15 | CF-27 | T-97 | T-97 | CF-28 | T-97 | T-15 |
| CE-29 | T-97 | T-88 | CE-30 | T-97 | T-99 | CF-29 | T-97 | T-88 | CF-30 | T-97 | T-99 |
| CE-31 | T-97 | T-112 | CE-32 | T-97 | T-120 | CF-31 | T-97 | T-112 | CF-32 | T-97 | T-120 |
| CE-33 | T-97 | T-134 | CE-34 | T-97 | T-141 | CF-33 | T-97 | T-134 | CF-34 | T-97 | T-141 |
| CE-35 | T-115 | T-115 | CE-36 | T-115 | T-112 | CF-35 | T-115 | T-115 | CF-36 | T-115 | T-112 |
| CE-37 | T-115 | T-118 | CE-38 | T-115 | T-134 | CF-37 | T-115 | T-118 | CF-38 | T-115 | T-134 |
| CE-39 | T-115 | T-141 | CE-40 | T-116 | T-116 | CF-39 | T-115 | T-141 | CF-40 | T-116 | T-116 |
| CE-41 | T-116 | T-112 | CE-42 | T-116 | T-134 | CF-41 | T-116 | T-112 | CF-42 | T-116 | T-134 |
| CE-43 | T-116 | T-141 | CE-44 | T-130 | T-130 | CF-43 | T-116 | T-141 | CF-44 | T-130 | T-130 |
| CE-45 | T-130 | T-134 | CE-46 | T-130 | T-141 | CF-45 | T-130 | T-134 | CF-46 | T-130 | T-141 |

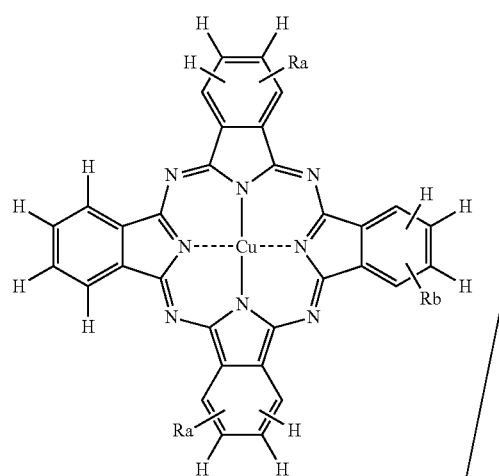

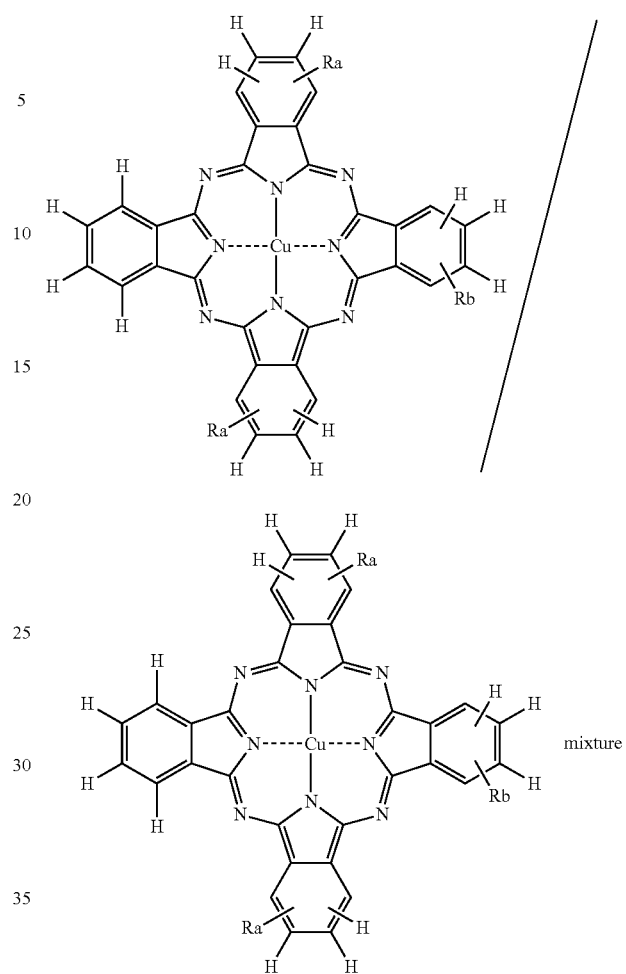

mixture mixture

| Exemplary Compound | Ra | Rb | Exemplary Compound | Ra | Rb | Exemplary Compound | Ra | Rb | Exemplary Compound | Ra | Rb |
|---|---|---|---|---|---|---|---|---|---|---|---|
| CG-1 | T-14 | T-14 | CG-2 | T-14 | T-15 | CI-1 | T-14 | T-14 | CI-2 | T-14 | T-15 |
| CG-3 | T-14 | T-88 | CG-4 | T-14 | T-99 | CI-3 | T-14 | T-88 | CI-4 | T-14 | T-99 |
| CG-5 | T-14 | T-141 | CG-6 | T-46 | T-46 | CI-5 | T-14 | T-141 | CI-6 | T-46 | T-46 |
| CG-7 | T-46 | T-49 | CG-8 | T-46 | T-56 | CI-7 | T-46 | T-49 | CI-8 | T-46 | T-56 |
| CG-9 | T-89 | T-89 | CG-10 | T-89 | T-88 | CI-9 | T-89 | T-89 | CI-10 | T-89 | T-88 |
| CG-11 | T-89 | T-99 | CG-12 | T-89 | T-141 | CI-11 | T-89 | T-99 | CI-12 | T-89 | T-141 |
| CG-13 | T-95 | T-95 | CG-14 | T-95 | T-88 | CI-13 | T-95 | T-95 | CI-14 | T-95 | T-88 |
| CG-15 | T-95 | T-112 | CG-16 | T-95 | T-15 | CI-15 | T-95 | T-112 | CI-16 | T-95 | T-15 |
| CG-17 | T-95 | T-114 | CG-18 | T-95 | T-134 | CI-17 | T-95 | T-114 | CI-18 | T-95 | T-134 |
| CG-19 | T-95 | T-141 | CG-20 | T-96 | T-96 | CI-19 | T-95 | T-141 | CI-20 | T-96 | T-96 |
| CG-21 | T-96 | T-88 | CG-22 | T-96 | T-99 | CI-21 | T-96 | T-88 | CI-22 | T-96 | T-99 |
| CG-23 | T-96 | T-112 | CG-24 | T-96 | T-134 | CI-23 | T-96 | T-112 | CI-24 | T-96 | T-134 |
| CG-25 | T-96 | T-134 | CG-26 | T-96 | T-141 | CI-25 | T-96 | T-135 | CI-26 | T-96 | T-141 |
| CG-27 | T-97 | T-97 | CG-28 | T-97 | T-15 | CI-27 | T-97 | T-97 | CI-28 | T-97 | T-15 |
| CG-29 | T-97 | T-88 | CG-30 | T-97 | T-99 | CI-29 | T-97 | T-88 | CI-30 | T-97 | T-99 |
| CG-31 | T-97 | T-112 | CG-32 | T-97 | T-120 | CI-31 | T-97 | T-112 | CI-32 | T-97 | T-120 |
| CG-33 | T-97 | T-134 | CG-34 | T-97 | T-141 | CI-33 | T-97 | T-134 | CI-34 | T-97 | T-141 |
| CG-35 | T-115 | T-115 | CG-36 | T-115 | T-112 | CI-35 | T-115 | T-115 | CI-36 | T-115 | T-112 |
| CG-37 | T-115 | T-118 | CG-38 | T-115 | T-134 | CI-37 | T-115 | T-118 | CI-38 | T-115 | T-134 |
| CG-39 | T-115 | T-141 | CG-40 | T-116 | T-116 | CI-39 | T-115 | T-141 | CI-40 | T-116 | T-116 |
| CG-41 | T-116 | T-112 | CG-42 | T-116 | T-134 | CI-41 | T-116 | T-112 | CI-42 | T-116 | T-134 |
| CG-43 | T-116 | T-141 | CG-44 | T-130 | T-130 | CI-43 | T-116 | T-141 | CI-44 | T-130 | T-130 |
| CG-45 | T-130 | T-134 | CG-46 | T-130 | T-141 | CI-45 | T-130 | T-134 | CI-46 | T-130 | T-141 |

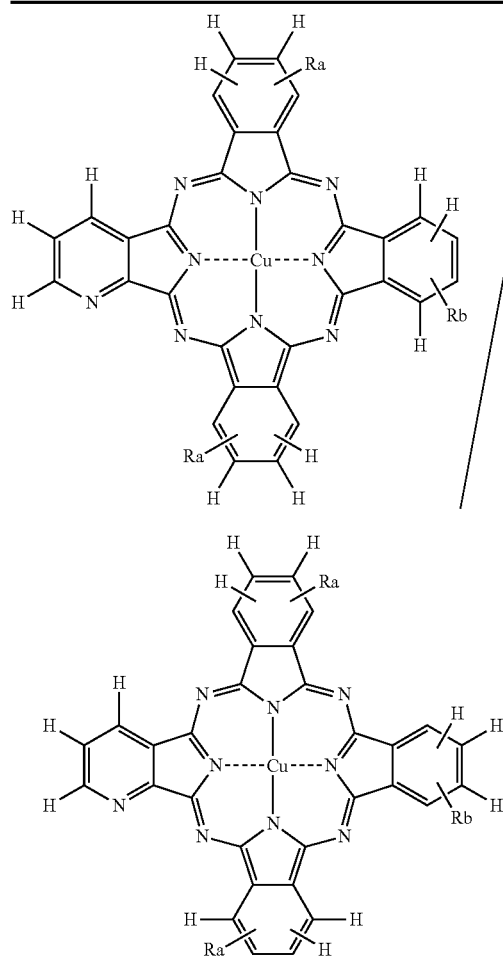

| Exemplary Compound | Ra | Rb | Exemplary Compound | Ra | Rb |
|---|---|---|---|---|---|
| CH-1 | T-14 | T-14 | CH-2 | T-14 | T-15 |
| CH-3 | T-14 | T-88 | CH-4 | T-14 | T-99 |
| CH-5 | T-14 | T-141 | CH-6 | T-46 | T-46 |
| CH-7 | T-46 | T-49 | CH-8 | T-46 | T-56 |
| CH-9 | T-89 | T-89 | CH-10 | T-89 | T-88 |
| CH-11 | T-89 | T-99 | CH-12 | T-89 | T-141 |
| CH-13 | T-95 | T-95 | CH-14 | T-95 | T-88 |
| CH-15 | T-95 | T-112 | CH-16 | T-95 | T-15 |
| CH-17 | T-95 | T-114 | CH-18 | T-95 | T-134 |
| CH-19 | T-95 | T-141 | CH-20 | T-96 | T-96 |
| CH-21 | T-96 | T-88 | CH-22 | T-96 | T-99 |
| CH-23 | T-96 | T-112 | CH-24 | T-96 | T-134 |
| CH-25 | T-96 | T-135 | CH-26 | T-96 | T-141 |
| CH-27 | T-97 | T-97 | CH-28 | T-97 | T-15 |
| CH-29 | T-97 | T-88 | CH-30 | T-97 | T-99 |
| CH-31 | T-97 | T-112 | CH-32 | T-97 | T-120 |
| CH-33 | T-97 | T-134 | CH-34 | T-97 | T-141 |
| CH-35 | T-115 | T-115 | CH-36 | T-115 | T-112 |
| CH-37 | T-115 | T-118 | CH-38 | T-115 | T-134 |
| CH-39 | T-115 | T-141 | CH-40 | T-116 | T-116 |
| CH-41 | T-116 | T-112 | CH-42 | T-116 | T-134 |
| CH-43 | T-116 | T-141 | CH-44 | T-130 | T-130 |
| CH-45 | T-130 | T-134 | CH-46 | T-130 | T-141 |

Synthesis Example

Hereinafter, methods of synthesizing the colorant represented by the Formula (A) or (B) will be described in detail along the following scheme D, by taking the exemplary compound CI-29 above as an example.

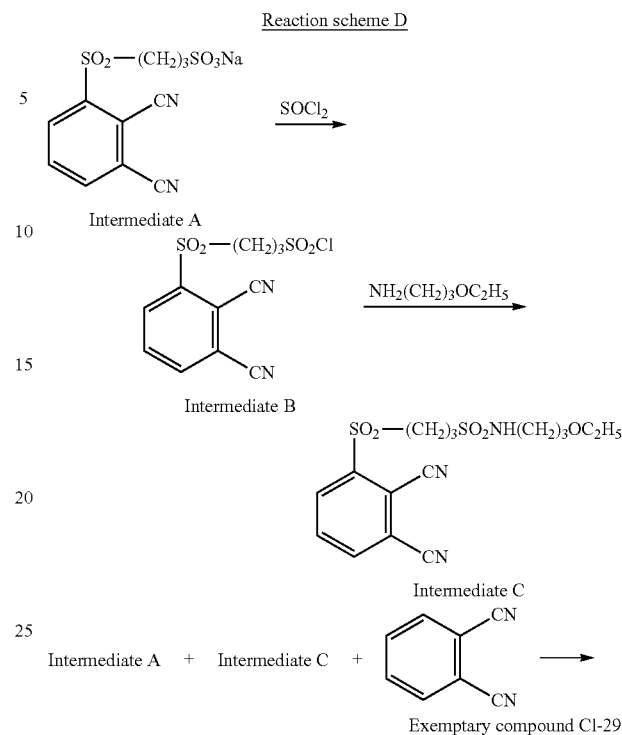

Synthesis of Intermediate A

Sodium carbonate (16.5 g, 0.156 mol) was added to a mixture of 3-nitrophthalonitrile (25 g, 0.144 mol), DMSO (200 ml), and sodium 3-mercaptopropanesulfonate salt (32 g, 0.18 mol), and the mixture was stirred as heated to 60° C. for 3 hours. The reaction mixture was poured into 10% sodium chloride water (300 g), and the precipitated solid was collected by filtration and washed with a mixed liquid of isopropanol/water (3/1). Water (200 ml), acetic acid (3 ml) and $Na_2WO_4$ (2 g) were added to the solid; 31% hydrogen peroxide solution (50 ml) was added thereto; and the mixture was stirred while heated at 60° C. After stirring for 4 hours, the reaction mixture was poured into isopropanol (500 ml), and the precipitated solid was collected by filtration and washed with a mixed liquid of isopropanol/water (3/1). The solid obtained was dried, to give an intermediate A 24 g (yield from 3-nitrophthalonitrile: 49%).

Synthesis of Intermediate B 67.3 g (0.2 mol) of the intermediate A was added to 200 ml of acetonitrile, and the mixture was stirred while heated at 70° C. to 75° C. 37 ml phosphorus oxychloride was added to the dispersion dropwise. After dropwise addition, the mixture was stirred at 70 to 75° C. for 4 hours, to complete the reaction. After reaction, the reaction solution was cooled to room temperature, and poured into 2,000 ml of stirred water, allowing precipitation of the crystal. The crystal was filtered, washed with water, and dispersed in 300 ml of 2-propanol. The dispersion was stirred for 1 hour and filtered, and the filtration residue was dried, to give 63.0 g of an intermediate B (yield: 94.5%).

Synthesis of Intermediate C 250 ml of acetonitrile was added to 50.0 g (0.15 mol) of the intermediate B obtained by the method above, and the mixture was stirred while cooled to 5° C. 31.0 g of 3-ethoxypropylamine was added to the solution dropwise. After dropwise addition, the mixture was allowed to warm to room temperature and stirred additionally for 2 hour, to complete the reaction. The reaction solution was poured into 1,500 ml of stirred water, allowing precipitation of the crystal. The crystal was filtered, washed with water, and dispersed in 500 ml of 2-propanol. The mixture was stirred for 2 hours at room temperature and then filtered, and the crystal was dried, to give 52.6 g of an intermediate C (yield: 87.7%).

Synthesis of CI-29

7.99 g (0.02 mol) of the intermediate C obtained by the method above, 1.28 g (0.01 mol) of o-phthalonitrile and 3.36 g (0.01 mol) of the intermediate A were mixed with 30 ml of diethylene glycol and 100 ml of 2-methoxypropanol, and the mixture was stirred while heated to 100° C. 3.87 g of ammonium benzoate and 1.26 g of copper acetate were added to the solution. After addition, the mixture was stirred at 95° C. to 100° C. for 6 hours, to complete the reaction. The reaction solution was cooled to room temperature; 60 ml of methanol was added; and the mixture was poured into an aqueous solution of 75 ml of hydrochloric acid in 800 ml of water while the mixture was stirred. The precipitated crystal was filtered and washed with water. The crystal was dissolved in 250 ml of methanol under heat, and the solution was filtered to remove the insoluble matter. The filtrate was concentrated under reduced pressure, and 250 ml of ethyl acetate was added to the residue, while the mixture was stirred. The dispersed crystal was filtered and dried, to give 24.7 g of an exemplary compound CI-29 (yield: 92.9%). The maximum absorption wavelength λmax and the molar absorption coefficient ε of CI-29 in chloroform were respectively 665.6 nm and 84,600.

The absorption maximum wavelength (λmax) and the molar absorption coefficient (ε) of the colorant in ethyl acetate, as determined by using a spectrophotometer UV-2400PC (manufactured by Shimadzu Corporation), were respectively 623.4 nm and 47,000.

Exemplary compounds other than the colorant CI-29 described above can be synthesized in a similar manner to the method above.

The maximum absorption wavelength λmax of the particular colorant B of the invention is preferably 580 nm to 700 nm, more preferably 600 nm to 680 nm, from the viewpoint of improvement in color purity. The maximum absorption wavelength was determined by using a spectrophotometer UV-2400PC (manufactured by Shimadzu Corporation).

Pyrroloazole-Based Azomethine Colorant Represented by Formula (C)

A pyrroloazole-based azomethine colorant represented by the following Formula (C) (hereinafter, suitably referred to as "particular colorant C") is used favorably in addition to the particular colorants A and B in the invention, and thus, it is possible to obtain a colored photosensitive curing composition superior in color purity and higher in transmittance particularly at a wavelength of 450 nm or less, and a color filter prepared by using the composition. The color filter can be used favorably, for example, in charge coupled devices (CCDs) and CMOSs.

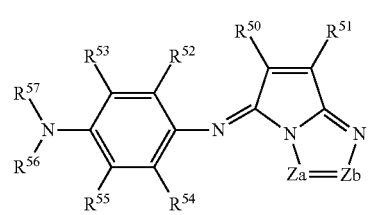

Formula (C)

In Formula (C), $R^{50}$ to $R^{55}$ each independently represent a hydrogen atom or a substituent group; $R^{56}$ and $R^{57}$ each independently represent a hydrogen atom or an alkyl, alkenyl, aryl, or heterocyclic group; and Za and Zb each independently represent —N= or —C($R^{58}$). $R^{58}$ represents a hydrogen atom or a substituent group. $R^{52}$ and $R^{53}$, $R^{53}$ and $R^{57}$, $R^{54}$ and $R^{55}$, $R^{55}$ and $R^{56}$, and/or $R^{56}$ and $R^{57}$ may bind to each other to form a five-, six-, or seven-membered ring.

The substituent groups for $R^{50}$ to $R^{55}$ in Formula (C) are the same as the substituent groups for $R^1$ to $R^6$ in Formula (I) above, and the preferable examples thereof are also the same.

When the substituent group of $R^{50}$ to $R^{55}$ in Formula (C) is a group that may be substituted additionally, the group may be substituted with one or more groups described as the substituent group for $R^1$ to $R^6$ above, and, when two or more substituent groups are substituted, the substituent groups may be the same as or different from each other. In Formula (C), $R^{56}$ and $R^{57}$ each independently represent a hydrogen atom or an alkyl, alkenyl, aryl, or heterocyclic group. Preferable examples of the alkyl, alkenyl, aryl, and heterocyclic group are the same as those for the $R^1$ to $R^6$ in Formula (I) above.

The alkyl, alkenyl, aryl or heterocyclic group for $R^{56}$ and $R^{57}$ in Formula (C) may be substituted with one or more substituent groups described for $R^1$ to $R^6$ above, and when two or more substituent groups are substituted, the substituent groups may be the same as or different from each other.

In Formula (C), Za and Zb each independently represent —N= or —C($R^{58}$). $R^{58}$ represents a hydrogen atom or a substituent group. The substituent group of $R^{58}$ is the same as the substituent group described in Formula (I) above, and the preferable ranges are the same. When the substituent group of $R^{58}$ is a group that may be substituted additionally, it may be the substituted with one or more groups described in Formula (I) above, and when it is substituted with two or more substituent groups, the substituent groups may be the same as or different from each other.

$R^{52}$ and $R^{53}$, $R^{53}$ and $R^{57}$, $R^{54}$ and $R^{55}$, $R^{55}$ and $R^{56}$, and/or $R^{56}$ and $R^{57}$ in the colorant represented by Formula (C) may bind to each other to form a five-, six-, or seven-membered ring.

In the particular colorant C, $R^{50}$ and $R^{51}$ are selected preferably from the substituent groups described for $R^1$ to $R^6$ above, and represent respectively substituent groups that give a total Hammett substituent constant σp value of the substituent groups represented by $R^{50}$ and $R^{51}$ of 0.7 or more, while $R^{59}$ represents a hydrogen atom or an alkyl, aryl or heterocyclic group.

Hammett equation is an empirical equation proposed by L. P. Hammett in 1935 and described in detail in common books, such as J. A. Dean Ed., "Lange's and Book of Chemistry", 12th Ed., 1979 (McGrew-Hill) and "Kagaku no Ryoiki" Special Issue No., 122, pp 96-103, 1979 (Nankodo). However, in the invention, even when each substituent group is restricted or specified by Hammett substituent constant σp value, the groups are not limited to substituent group having values known in the books above, and thus, include substituent groups having the σp values in the favorable range above when measured according to the Hammett equation. The "Hammett substituent constant σp value" used as the indicator of the electronic effect of the substituent group in the invention is a σp value independent of the substitution site, even for the substituent group is bound to a ring other than benzene.

Examples of the electron-withdrawing groups having a Hammett substituent constant σp value of 0.3 or more include acyl groups (preferably acyl groups having 1 to 24 carbon atoms, more preferably 2 to 18 carbon atoms, such as acetyl, pivaloyl, 2-ethylhexyl, benzoyl, and cyclohaxanoyl), acyloxy groups (preferably acyloxy groups having 2 to 24 carbon atoms, more preferably 2 to 12 carbon atoms, such as acetoxy and pivaloyloxy), carbamoyl groups (preferably carbamoyl groups having 1 to 24 carbon atoms, more preferably 1 to 18 carbon atoms, such as carbamoyl, N-methylcarbamoyl, N-ethylcarbamoyl, N-t-butylcarbamoyl, N-cyclohexylcarbamoyl, N-pheylcarbamoyl, N,N-diethylcarbamoyl, N,N-diisopropylcarbamoyl, and N-ethyl-N-pheylcarbamoyl), alkoxycarbonyl groups (preferably alkoxycarbonyl groups having 1 to 24 carbon atoms, more preferably 1 to 18 carbon atoms, such as methoxycarbonyl, ethoxycarbonyl, isopropyloxycarbonyl, and cyclohexylcarbonyl), aryloxycarbonyl groups (preferably aryloxycarbonyl groups having 7 to 24 carbon atoms, more preferably 7 to 18 carbon atoms, such as phenoxycarbonyl), a cyano group, a nitro group, alkylsulfinyl groups (preferably alkylsulfinyl groups having 1 to 24 carbon atoms, more preferably 1 to, 18, such as methylsulfinyl, ethylsulfinyl, butylsulfinyl, 2-ethylhexylsulfinyl, and cyclopentylsulfinyl), arylsulfinyl groups (preferably arylsulfinyl groups having 6 to 24 carbon atoms, more preferably 6 to 18 carbon atoms, such as phenylsulfinyl and p-toluene sulfinyl), alkylsulfonyl groups (preferably alkyl sulfonyl groups having 1 to 24 carbon atoms, more preferably 1 to 18 carbon atoms, such as methylsulfonyl, ethylsulfonyl, isopropylsulfonyl, and cyclohexylsulfonyl), arylsulfonyl groups (preferably arylsulfonyl groups having 6 to 24 carbon atoms, more preferably 6 to 18 carbon atoms, such as phenylsulfonyl and naphthylsulfonyl), sulfamoyl groups (preferably sulfamoyl groups having 24 or less carbon atoms, more preferably 18 or less, such as N-ethylsulfamoyl, N,N-dipropylsulfamoyl, N-ethyl-N-phenylsulfamoyl, N-phenylsulfamoyl, and N-cyclohexylsulfamoyl), alkyl halide groups (preferably alkyl halide groups having 1 to 24 carbon atoms, more preferably 1 to 12 carbon atoms, such as trifluoromethyl and pentafluoropropyl), halogenated alkoxy groups (preferably halogenated alkoxy groups having 1 to 24 carbon atoms, more preferably 1 to 18 carbon atoms, such as trifluoromethoxy), halogenated aryloxy groups (preferably halogenated aryloxy groups having 6 to 24 carbon atoms, more preferably 6 to 12 carbon atoms, such as pentafluorophenyloxy), heterocyclic groups (preferably heterocyclic groups having 1 to 24 carbon atoms, more preferably 1 to 12 carbon atoms, such as 2-benzoxazolyl, 2-benzothiazolyl, 1-phenyl-2-benzimidazolyl, 5-chloro-1-tetrazolyl, and 1-pyrrolyl), and the like.

Specific examples of the compounds represented by Formula (C) (CD-1 to CD-46) are shown below, however the examples are not limited thereto in the invention.

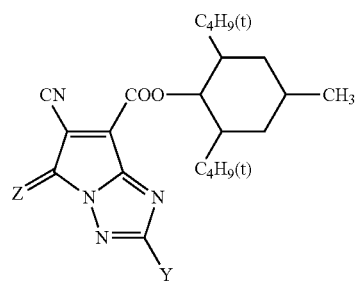

| Dye No. | Y | Z |
|---|---|---|
| CD-1 | 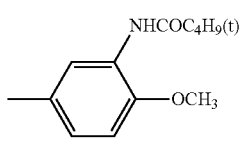 | 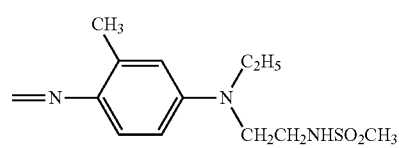 |
| CD-2 | ditto | 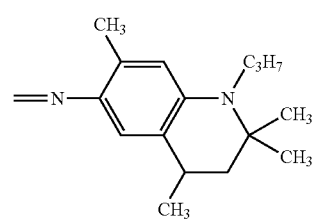 |

-continued

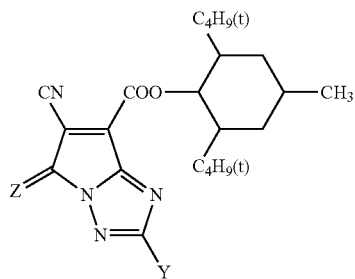

| Dye No. | Y | Z |
|---|---|---|
| CD-3 | ditto | (6-imino-1-(2-hydroxyethyl)-2,2,4,7-tetramethyl-1,2,3,4-tetrahydroquinoline; N-substituent: CH₂CH₂CH₂OH) |
| CD-4 | ditto | (6-imino-1-(3-carboxypropyl)-2,2,4,7-tetramethyl-1,2,3,4-tetrahydroquinoline; N-substituent: CH₂CH₂CH₂COOH) |
| CD-5 | ditto | (6-imino-1-(2-methanesulfonamidoethyl)-2,2,4,7-tetramethyl-1,2,3,4-tetrahydroquinoline; N-substituent: CH₂CH₂NHSO₂CH₃) |
| CD-6 | ditto | (6-imino-2,2,4,7-tetramethyl-1,2,3,4-tetrahydroquinoline; N-substituent: CH₂CH₂CH₂CH₂CH₂COONa) |
| CD-7 | ditto | (6-imino-2,2,4,7-tetramethyl-1,2,3,4-tetrahydroquinoline; N-substituent: CH₂CH₂CH₂SCH(COOH)CH₂COOH) |

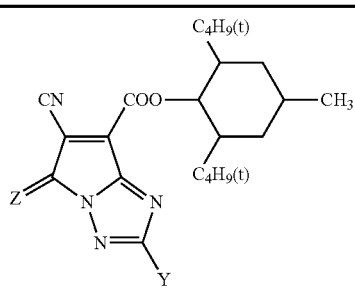

| Dye No. | Y | Z |
|---|---|---|
| CD-8 | (5-methyl-2-methoxyphenyl)-NHCOC₄H₉(t) | =N-C₆H₃(NHCOCH₃)-N(CH₂CH₂CN)₂ |
| CD-9 | ditto | =N-C₆H₃(NHCOC₂H₅)-N(CH₂COOH)₂ |
| CD-10 | ditto | =N-C₆H₃(CH₃)-N(C₂H₅)(CH₂CH₂OH) |
| CD-11 | ditto | =N-C₆H₃(F)-N(CH₂COOC₂H₅)₂ |
| CD-12 | ditto | =N-C₆H₃(NHCOC₄H₉(t))-(pyrrolidino) |
| CD-13 | ditto | =N-(6-NHCOCH₃-tetrahydroquinolinyl)-N-CH₂CH₂CH₂SCH₂COOH |
| CD-14 | (5-methyl-2-methoxyphenyl)-NHCOCH₂CH₂COOH | =N-(7-CH₃-2,2,4-trimethyl-tetrahydroquinolinyl)-N-CH₂CH₂CH₂COOH |
| CD-15 | (5-methyl-2-methoxyphenyl)-NHSO₂CH₃ | ditto |

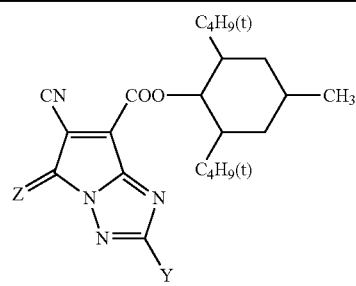

| Dye No. | Y | Z |
|---|---|---|
| CD-16 | 2-OC₄H₉, 5-methyl phenyl with NHCOC₄H₉(t) | 7-CH₃, 2,2,4-trimethyl-1-(CH₂CH₂CH₂COOH)-1,2,3,4-tetrahydroquinolin-6-ylimino |
| CD-17 | 3-methylphenyl with NHCOC₄H₉(t) | ditto |
| CD-18 | 4-C₄H₉(t)-phenyl | ditto |
| CD-19 | 3-methylphenyl with NHSO₂CH₃ | ditto |
| CD-20 | —C₄H₉(t) | ditto |
| CD-21 | —CF₃ | ditto |
| CD-22 | 2-pyridyl (methyl-substituted) | ditto |
| CD-23 | 3-pyridyl (methyl-substituted) | ditto |
| CD-24 | 2-NHCOCH₃, 4-methyl phenyl with N(C₂H₅)(CH₂CH₂COOH) | 7-CH₃, 2,2,4-trimethyl-1-(CH₂CH(C₂H₅)C₄H₉)-1,2,3,4-tetrahydroquinolin-6-ylimino |
| CD-25 | 2-OCH₂CH₂CH₂COOH, 5-methyl phenyl with NHCOC₄H₉(t) | ditto |

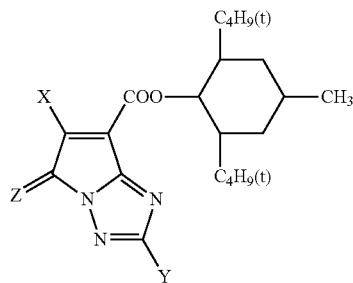

| Dye No. | X | Y | Z |
|---|---|---|---|
| CD-26 | —CF₃ | 5-methyl-2-methoxy phenyl with NHCOCH₃ | N=... 1,2,3,4-tetrahydroquinoline with 2,2,4,7-tetramethyl and N-CH₂CH₂CH₂COOH |
| CD-27 | —SO₂CH₃ | 5-methyl-2-methoxy phenyl with NHCOC₄H₉(t) | ditto |
| CD-28 | —SO₂—C₆H₄—CH₃ | ditto | ditto |
| CD-29 | 2-methylpyridinyl | ditto | ditto |
| CD-30 | —SO₂NHCH₂CH(C₂H₅)C₄H₉ | ditto | ditto |
| CD-31 | —COOC₂H₅ | ditto | ditto |
| CD-32 | —CN | 3-methylphenyl with SO₃K | ditto |
| CD-33 | ditto | —CH(CH₃)CH₂NHSO₂CH₃ | ditto |
| CD-34 | ditto | —CH(CH₃)CH₂—N(succinimide) | ditto |

CD-35
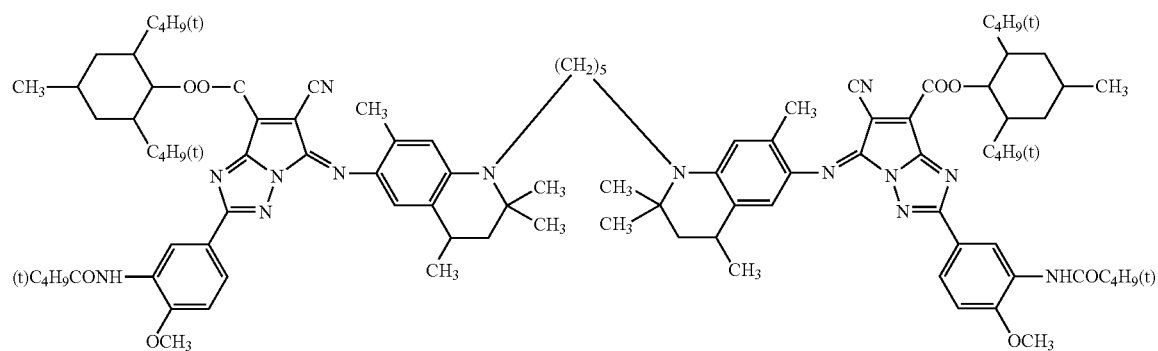
CD-36
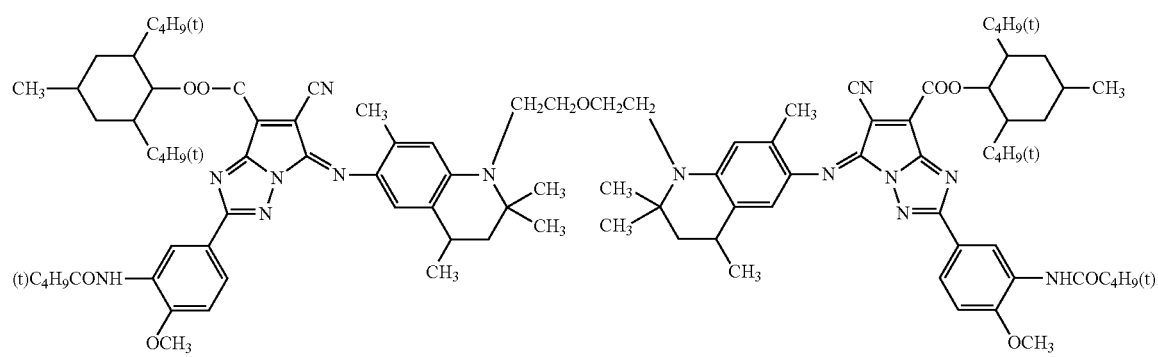
CD-37
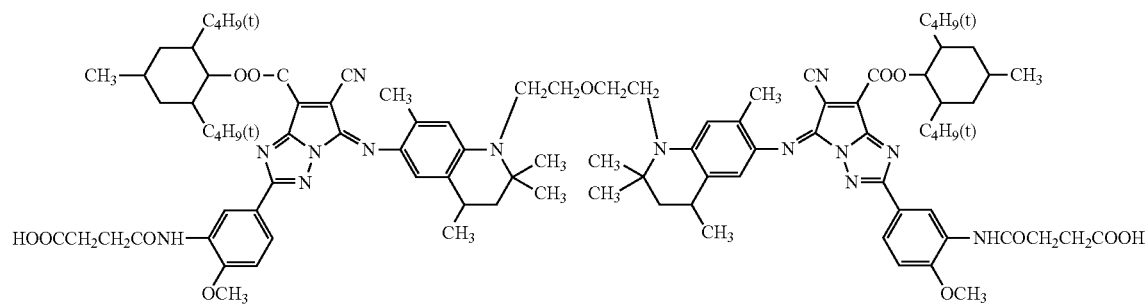

-continued
CD-38
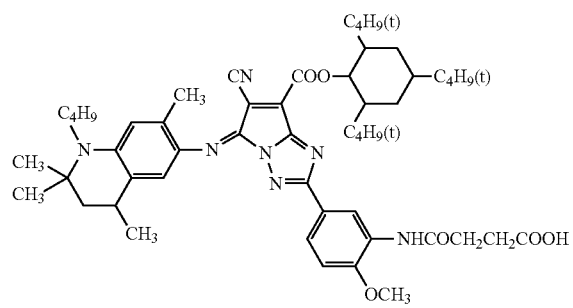
CD-39
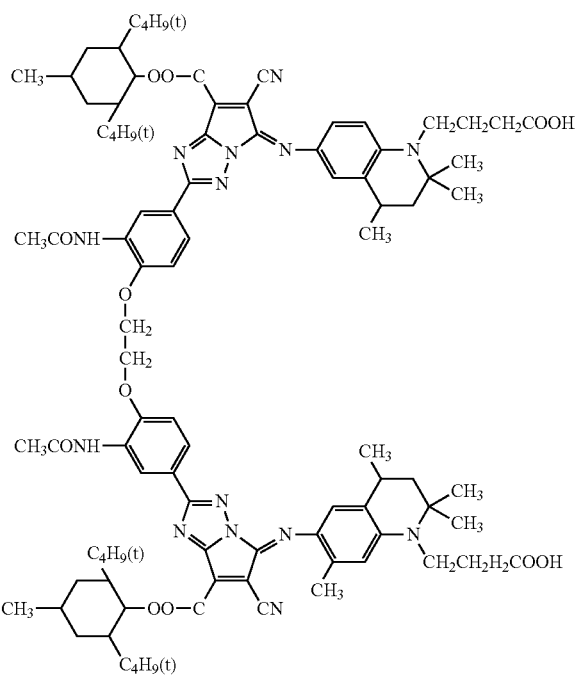
CD-40
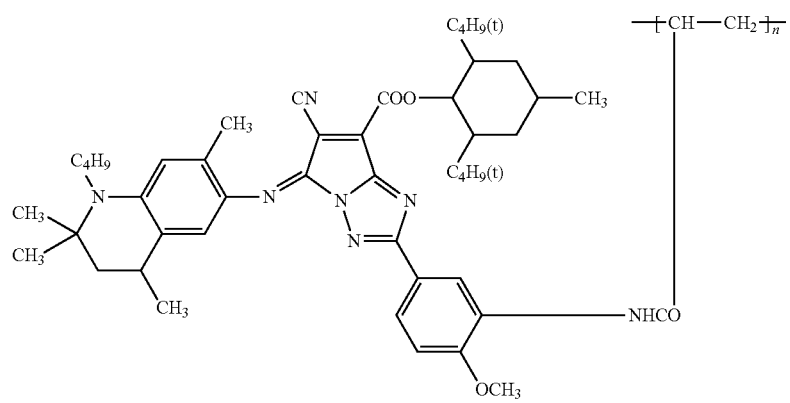
CD-41
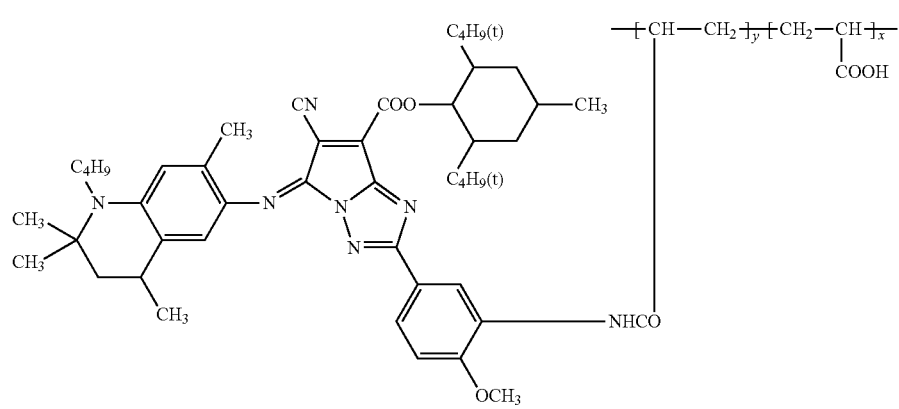
Y/X = 90/10wt%

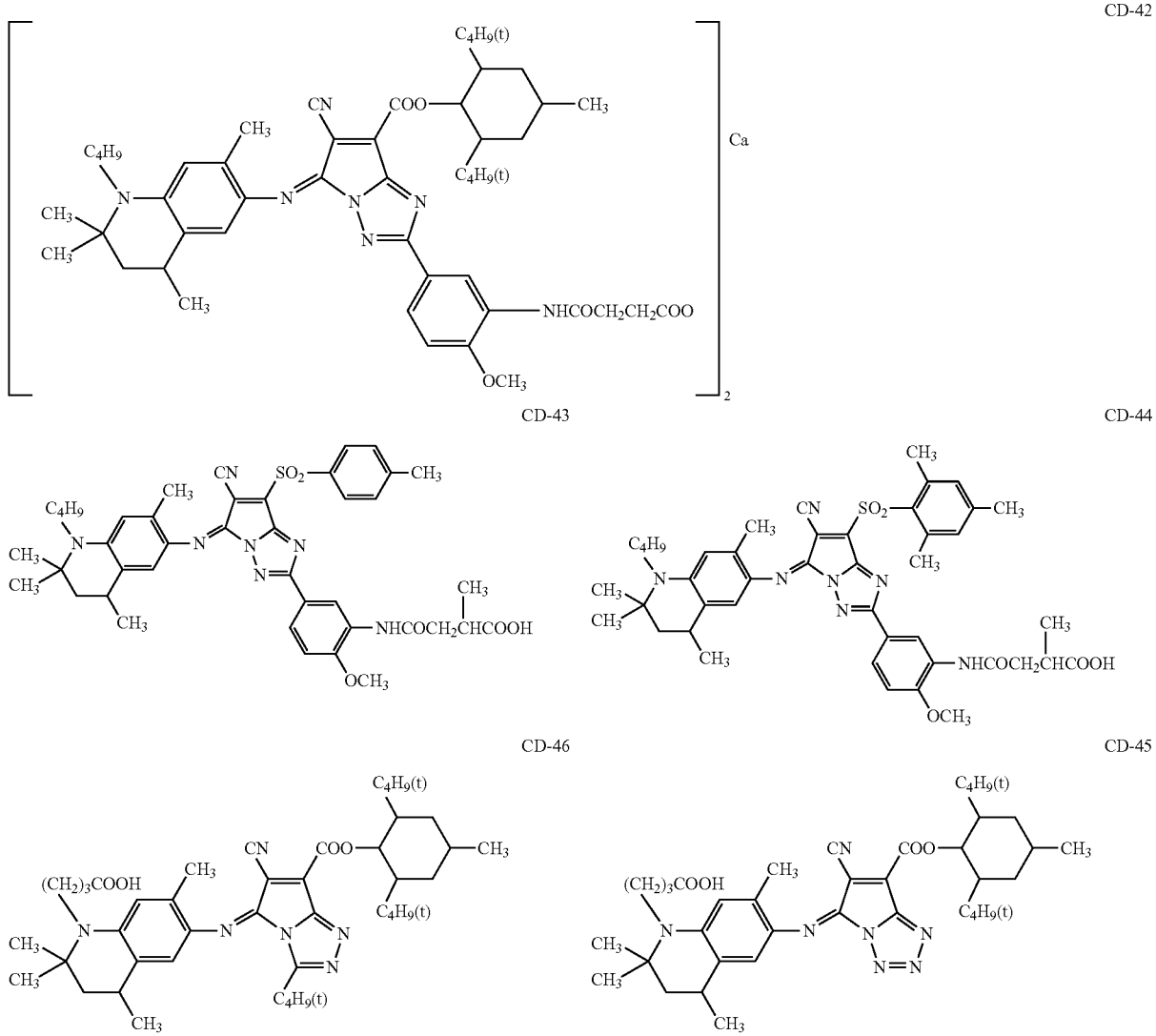

The compounds represented by Formula (C) are synthesized by the methods described in JP-A No. 5-177959, paragraph numbers [0070] to [0072], JP-A No. 2003-96326, paragraph numbers [0041] to [0054], JP-A No. 2003-96327, paragraph numbers [0043] to [0056], and others.

The maximum absorption wavelength λmax of the particular colorant C of the invention is preferably 580 nm to 700 nm, more preferably 600 nm to 680 nm, from the viewpoint of improvement in color purity. The maximum absorption wavelength and the molar absorption coefficient were determined by using a spectrophotometer UV-2400PC (manufactured by Shimadzu Corporation).

The content of the particular colorant A, B, or C, when present, may vary, for example, according to the molar absorption coefficient of the colorant and desired spectroscopic properties and film thickness of the color filter, but is preferably 1 to 80% by mass, more preferably 10% by mass to 70% by mass, with respect to the total solid content in the colored ultraviolet-sensitive curing composition of the invention. These colorants may be contained alone or in combination of two or more kinds in colored photosensitive curing composition of the invention.

The colored photosensitive curing composition of the invention and the color filter using the colored photosensitive curing composition may contain a triarylmethane-based colorant having the absorption maximum at 550 to 650 nm such as C.I. Acid Blue 7, C.I. Acid Blue 83, C.I. Acid Blue 90, C.I. Solvent Blue 38, C.I. Acid Violet 17, C.I. Acid Violet 49 or C.I. Acid Green 3, in addition to the colorant of the invention.

Alternatively, a xanthene-based colorant having the absorption maximum at 500 to 600 nm such as C.I. Acid Red 289 may be used.

The content of the triarylmethane-based colorant is arbitrary in the range that does not impair the advantageous effects of the invention, and preferably 0.5 to 50% by mass, with respect to the total solid content in the colored photosensitive curing composition of the invention.

Preferably in preparing a blue filter array, the particular metal complex compound I (including particular metal complex compound II) or the particular boron complex compound is used together with at least one of the particular colorants A, B, and C as they are mixed.

The blending ratio then may vary, for example, according to the molar absorption coefficient of the colorant and the desired spectroscopic properties and film thickness of the color filter, however generally, the content ratio (total content of particular metal complex compound I (including particular metal complex compound II) or the particular boron complex compound):(total content of the particular colorants A, B, and C) is in the range of 20:1 to 1:20. It is more preferably in the range of 10:1 to 1:10.

<Binder>

It is preferable that the colored curable composition of the present invention may contain at least one kind of binder. The binder used in the invention is not particularly limited as long as it is alkali-soluble, and is preferably selected in view of heat-resistance, developability, availability, and the like.

The alkali-soluble binder is preferably a linear organic polymer soluble in organic solvents and developable with an aqueous weakly alkaline solution. Examples of such linear organic polymer include polymers having a carboxylic acid at their side chain, for example methacrylic acid copolymers, acrylic acid copolymers, itaconic acid copolymers, crotonic acid copolymers, maleic acid copolymers and partially esterified maleic acid copolymers as described in the specifications of JP-A Nos. 59-44615, 59-53836 and 59-71048, and JP-B Nos. 54-34327, 58-12577 and 54-25957. Acidic cellulose derivatives having a carboxylic acid at the side chain are particularly useful. Other useful binders include polymers prepared by adding an acid anhydride to a polymer having a hydroxyl group, polyhydroxystyrene resins, polysiloxane resins, poly(2-hydroxyethyl (meth)acrylate), polyvinyl pyrrolidone, polyethylene oxide and polyvinyl alcohol.

A Hydrophilic monomer may be copolymerized with the alkali-soluble binder. Examples of such monomer include alkoxyalkyl (meth)acrylate, hydroxyalkyl (meth)acrylate, glycerol (meth)acrylate, (meth)acrylamide, N-methylol acrylamide, secondary or tertiary alkyl acrylamide, dialkylaminoalkyl (meth)acrylate, morpholine (meth)acrylate, N-vinyl pyrrolidone, N-vinyl caprolactam, vinyl imidazole, vinyl triazole, methyl (meth)acrylate, ethyl (meth)acrylate, branched or linear propyl (meth)acrylate, branched or linear butyl (meth)acrylate, and phenoxyhydroxypropyl (meth)acrylate.

Other preferable hydrophilic monomers include those containing tetrahydrofurfulyl group, phosphate, phosphate ester, quaternary ammonium salt, ethyleneoxy chain, propyleneoxy chain, sulfonic acid group and salts thereof, and morpholinoethyl groups.

The alkali-soluble binder may have polymerizable groups at the side chain for improving the cross-linking efficiency. Polymers having allyl group, (meth)acrylic or allyloxyalkyl groups at the side chains are also preferable.

Examples of polymer having these polymerizable groups include KS Resist-106 (manufactured by Osaka Chemical Industry Ltd.), and Cyclomer P Series (manufactured by Daicel Chemical Industries, Ltd.). To increase the strength of the cured film, alcohol soluble nylon, and polyether of 2,2-bis(4-hydroxyphenyl)-propane and epichlorhydrine are also useful.

Among the binders, the alkali-soluble binder that can be used in the invention includes, from the viewpoint of heat resistance, polyhydroxy styrene resin, polysiloxane resin, acrylic resin, acrylamide resin, and acryl/acrylamide copolymer resin. From the viewpoint of control of developing performance, preferred examples include an acrylic resin, an acrylamide resin, and an acryl/acrylamide copolymer resin. Acrylic resin preferably includes copolymer prepared by polymerizing monomer selected from a benzyl (meth)acrylate, a (meth)acryl acid, a hydroxyethyl (meth)acrylate, and a (meth)acrylamide, KS Resist-106 (manufactured by Osaka Chemical Industry Ltd.), and Cyclomer P Series (manufactured by Daicel Chemical Industries, Ltd.).

As the alkali-soluble binder, alkali-soluble phenol resin can be used. The alkali-soluble phenol resin is suitably used when the photosensitive colored curable composition of the invention is composed as a positive working composition. The alkali-soluble phenol resin includes novolak resin and vinyl polymer.

The novolak resin is produced, for example, by condensing phenols and aldehydes in the presence of acid catalyst. The phenols include a phenol, a cresol, an ethyl phenol, a butyl phenol, a xylenol, a phenyl phenol, a catechol, a resorcinol, a pyrogallol, a naphthol, and a bisphenol A.

Aldehydes include a formaldehyde, a paraformaldehyde, an acetaldehyde, a propionaldehyde, and a benzaldehyde.

The phenols and the aldehydes may be used either alone or in combination of two or more types.

Specific examples of novolak resin include a methacresol, a paracresol, and a condensation product of their mixture and formalin.

Molecular weight distribution of novolak resin may be adjusted by sorting or other means. The novolak resin may also contain low molecular weight component having a phenolic hydroxy group such as a bisphenol C or a bisphenol A.

The alkali-soluble binder is preferably polymers having a weight-average molecular weight (polystyrene-equivalent value measured by GPC method) of 1000 to $2 \times 10^5$, more preferably polymer having a weight-average molecular weight of 2000 to $1 \times 10^5$, and particularly polymer having a weight-average molecular weight of 5000 to $5 \times 10^4$.

The content of the above described binder in the photosensitive colored curable composition is preferably 10 to 90% by mass, more preferably 20 to 80% by mass, particularly 30 to 70% by mass, relative to the total solid content of the composition.

<Crosslinking Agent>

The colored photosensitive curing composition of the invention, which contains the particular metal complex compound I (including particular metal complex compounds II-1, II-2, III, and IV) described above as a colorant, is higher in color purity, has a higher absorption coefficient allowing reduction in the thickness, and is better in fastness than conventional compositions, and it is possible to obtain a more extensively cured film by using a crosslinking agent additionally.

The cross-linking agent available in the invention is not particularly restricted, so long as it is able to cure the layer with the cross-linking agent, and examples of the cross-linking agent include (a) epoxy resins, (b) melamine compounds, guanamine compounds, glycoluryl compounds or urea compounds substituted with at least one substituent selected from methylol group, alkoxymethyl group and acyloxymethyl group, and (c) phenol compounds, naphthol compounds or hydroxyanthrathene compounds substituted with at least one substituent selected from methylol group, alkoxymethyl group and acyloxymethyl group. A multifunctional epoxy resins are particularly preferable.

Any resins may be used as the epoxy resin in the (a) so long as the resin comprises epoxy groups and has a cross-linking property. Examples of the epoxy resin include bis(glycidyl group)-containing low molecular weight compounds such as bisphenol A diglycidyl ether, ethyleneglycol diglycidyl ether, butanediol diglycidyl ether, hexanediol diglycidyl ether, dihydroxybiphenyl diglycidyl ether, diglycidyl phthalate and N,N-diglycidylaniline; tris(glycidyl group)-containing low molecular weight compounds represented by trimethylolpropane triglycidyl ether, trimethylolphenol triglycidyl ether and tris P-PA triglycidyl ether; tetrakis(glycidyl group)-containing low molecular weight compounds represented by pentaerythritol tetraglycidyl ether and tetramethylol bisphenol A tetraglycidyl ether; poly(glycidyl group)-containing low molecular weight compounds such as dipentaerythritol pentaglycidyl ether and dipentaerythritol hexaglycidyl ether; and glycidyl group-containing high molecular weight compounds represented by polyglycidyl (meth)acrylate and 1,2-epoxy-4-(2-oxylanyl)cyclohexane adduct of 2,2-bis(hydroxymethyl)-1-butanol.

With regard to a number of the methylol group, alkoxymethyl group or acyloxymethyl group by which the compound (b) is substituted, the melamine compound is substituted by 2 to 6 of these substituents, and each of the glycoluryl compound, the guanamine compound, and the urea compound is substituted by 2 to 4 of these substituents. It is preferable that the melamine compound is substituted by 5 to 6 of these substituents, and each of the glycoluryl compound, the guanamine compound, and the urea compound is substituted by 3 to 4 of these substituents.

Hereinafter, the melamine compounds, guanamine compounds, and glycouryl compounds of the compounds (b) may sometimes be referred to as the compounds (b) (methylol-group containing, alkoxymethyl-group containing, or acyloxymethyl group containing).

These methylol-group containing compounds (b) can be obtained by heating the alkoxymethyl-group containing compounds (b) in the presence of an acidic catalyst, such as hydrochloric acid, sulfuric acid, nitric acid, or methansulfonic acid, in alcohol. The acyloxymethyl-group containing compound (b) can be obtained by mixing a methylol-group containing compound (b) with acylchloride and mixing them by stirring in the presence of a basic catalyst.

Hereinafter, specific examples of the compound (b) having substituents are mentioned.

Examples of the melamine compound include a hexamethylol melamine, hexamethoxymethyl melamine, compounds in which 1 to 5 methylol groups of hexamethylol melamine are methoxymethylated or mixtures thereof, hexamethoxyethyl melamine, hexaacyloxymethyl melamine, compounds in which 1 to 5 methylol groups of hexamethylol melamine are acyloxymethylated or mixtures thereof, and the like.

Examples of the guanamine compound include tetramethylol guanamine, tetramethoxymethyl guanamine, compounds in which 1 to 3 methylol groups of tetramethylol guanamine are methoxymethylated or mixtures thereof, tetramethoxyethyl guanamine, tetraacyloxymethyl guanamine, compounds in which 1 to 3 methylol groups of tetramethylol guanamine are acyloxymethylated or mixtures thereof, and the like.

Examples of the glycoluryl compound include tetramethylol glycoluryl, tetramethoxymethyl glycoluryl, compounds in which 1 to 3 methylol groups of tetramethylol glycoluryl are methoxymethylated or mixtures thereof, compounds in which 1 to 3 methylol groups of tetramethylol glycoluryl are acyloxymethylated or mixtures thereof, and the like.

Examples of the urea compound include tetramethylol urea, tetramethoxymethyl urea, compounds in which 1 to 3 methylol groups of tetramethylol urea are methoxymethylated or mixtures thereof, tetramethoxyethyl urea, and the like. These may be used alone or in combination of two or more thereof.

The phenolic compound, naphtholic compound, and hydroxyanthracene compound which are categorized as the compound (c), being substituted by at least one substituent selected from the group consisting of the methylol group, alkoxymethyl group, and acyloxymethyl group suppress intermixing with an overcoated photoresist by a thermal crosslinking, and further enhance a film strength, as are the case with the compound (b).

Hereinafter, these compounds may sometimes be referred to as a compound of (c) (a methylol-containing compound, an alkoxymethyl-containing compound, or an acyloxymethyl-containing compound).

The number of the methylol group, the acryloxymethyl group, or an alkoxymethyl group contained in the cross-linking agent (c) is required to be at least two per one molecule and from a viewpoint of the thermal cross-linking property and storage stability, the phenol compounds to be a skeleton whose second position and fourth positions are all substituted are preferable. Also, the naphthol compounds and hydroxyanthracene compounds to be a skeleton in which ortho-positions and para-positions to the OH groups are all substituted are also preferable. The phenol compounds to be a skeleton whose third position and fifth positions may be unsubstituted or substituted. Also, the naphthol compounds and hydroxyanthracene compounds to be a skeleton in which positions other than the ortho-positions to the OH groups may be unsubstituted or substituted.

The methylol group-containing compound of the category (c) can be obtained by using a phenolic hydroxyl group-containing compound whose 2- or 4-position of the phenolic hydroxyl group is a hydrogen atom as a raw material and reacting it with formalin in the presence of a basic catalyst, such as sodium hydroxide, potassium hydroxide, ammonia and tetraalkylammonium hydroxide. The alkoxymethyl group-containing compound of the category (c) can be obtained by heating the methylol group-containing compound of the category (c) in an alcohol in the presence of an acid catalyst, such as hydrochloric acid, sulfuric acid, nitric acid and methanesulfonic acid. The acyloxymethyl group-containing compound of the category (c) can be obtained by reacting the methylol group-containing compound of the category (c) with an acyl chloride in the presence of a basic catalyst.

Examples of the skeleton compound in the cross-linking agent (c) include a phenol compound, naphthol and a hydroxy anthracene compound in which the ortho position or para position of the phenolic OH group is unsubstituted. Specific examples thereof include phenol, the isomers of cresol, 2,3-xylenol, 2,5-xylenol, 3,4-xylenol, 3,5-xylenol, bisphenols such as bisphenol A, 4,4'-bishydroxy biphenyl, TrisP-PA (manufactured by Honshu Chemical Industry Co., Ltd.), naphthol, dihydroxy naphthalene and 2,7-dihydroxy anthracene.

As specific examples of the crosslinking agent of the category (c), examples of the phenol compound include trimethylolphenol, tri(methoxymethyl)phenol, a compound obtained by methoxymethylating from 1 to 2 methylol groups of trimethylolphenol, trimethylol-3 cresol, tri(methoxymethyl)-3 cresol, a compound obtained by methoxymethylating from 1 to 2 methylol groups of trimethylol-3 cresol, a dimethylolcresol, such as 2,6 dimethylol-4 cresol, tetramethylolbisophenol A, tetramethoxymethylbisphenol A, a compound obtained by methoxymethlating from 1 to 3 methylol groups of tetramethylolbisphenol A, tetramethylol-4,4' bishydroxybiphenyl, tetramethoxymethyl-4,4' bishydroxybiphenyl, a hexamethylol compound of TrisP PA, a hexamethoxymethyl compound of TrisP PA, a compound obtained by methoxymethylating from 1 to 5 methylol groups of a hexamethylol compound of Tris P PA, and bishydroxymethylnaphthalenediol.

Also, examples of the hydroxyanthracene compounds may include 1,6-dihydroxymethyl-2,7-dihydroxyanthracene.

Also, examples of the acyloxymethyl-containing compounds may include compounds obtained by acyloxymethylating some or all of methylol groups of the above-mentioned methylol-containing compounds.

Preferable examples among them are trimethylolphenol, bihydroxymethyl-p-cresol, tetramethylolbisphenol A, hexamethylol compounds of TrisP-PA (trade name; manufactured by Honshu Chemical Industry Co., Ld.) and phenol compounds obtained by substituting the methylol groups of these compounds with alkoxymethyl groups or both of methylol groups and alkoxymethyl groups. The compounds of (c) may be used alone or in combination.

When cross-linking agent is contained in the colored curable composition, the content of the cross-linking agents (a) to (c) is preferably 1 to 70% by weight, more preferably 5 to 50% by weight, and even more preferably 7 to 30% by weight in the total solid matter (weight) of the composition, although it differs depending on the materials. If the content is within the above-mentioned range, sufficient cured hardness and an unexposed part eluting property can reliably be attained and insufficient hardness of the exposed part is prevented from or considerable deterioration of the unexposed part eluting property is efficiently prevented.

<Polymerizable Monomer>

The colored photosensitive curing composition of the invention favorably contains at least one polymerizable monomer. The polymerizable monomer is mainly contained when the colored photosensitive curing composition is negative.

It may be added with a photopolymerization initiator described below to a positive system containing a naphthoquinonediazide compound described below, and in such a case, it is possible to accelerate curing of the formed pattern further. Hereinafter, the polymerizable monomer will be described.

As the monomer, a compound which has at least one addition-polymerizable ethylene group, has a boiling point of 100° C. or more under normal pressure, and has an ethylenic unsaturated group, is preferable. Examples thereof include: monofunctional acrylates and methacrylates such as polyethylene glycol mono(meth)acrylate, polypropylene glycol mono(meth)acrylate, phenoxyethyl (meth)acrylate; polyethylene glycol di(meth)acrylates; trimethylol ethane tri(meth)acrylates; neopentyl glycol di(meth)acrylates; pentaerythritol tri(meth)acrylates; pentaerythritol tetra(meth)acrylates; dipentaerythritol penta(meth)acrylates; dipentaerythritol hexa(meth)acrylates; hexanediol (meth)acrylates; trimethylol propane tri(acryloyloxypropyl)ether; tri(acryloyloxyethyl)isocyanulate; compounds obtained by adding ethylene oxides, propylene oxides or the like to multifunctional alcohols, such as glycerin or trimethylol ethane, and then (meth)acrylating the resultant of the reaction; urethane acrylates such as those disclosed in Japanese Patent Application Publication (JP-B) Nos. 48-41708 and 50-6034 or Japanese Patent Application Laid-Open (JP-A) No. 51-37193; polyester acrylates such as those disclosed in Japanese Patent Application Laid-Open (JP-A) No. 48-64183, Japanese Patent Application Publication (JP-B) Nos. 49-43191 and 52-30490; and multifunctional acrylates or methacrylates, such as epoxyacrylates, which are reaction products of epoxy resins and (metha)acrylic acids, and mixtures thereof.

Further, examples thereof includes those introduced as light curable monomers and oligomers in Journal of the Adhesion Society of Japan, Vol. 20, No. 7, pp. 300 to 308

The content of the monomer in the photosensitive colored curable composition of the present invention is preferably 0.1 to 90% by mass, more preferably 1.0 to 80% by mass, and particularly preferably 2.0 to 70% by mass with respect to the solid content of the composition.

<Radiation-Sensitive Compound>

The photosensitive colored curable composition of the invention comprises at least one kind selected from the radiation-sensitive compounds. The radiation-sensitive compound is able to effect chemical reactions such as generation of radicals, acids and bases by irradiation of UV light of which wavelength is 400 nm or less. The radiation-sensitive compound is used for making the alkali-soluble binder insoluble by cross-linking, polymerization and decomposition of acidic groups, or for making coating layers insoluble to an alkali developer by inducing polymerization of the polymerizable monomer and oligomer remaining in the coating layer or cross-linking of the cross-linking agent.

In particular, when the photosensitive colored curable composition is composed in negative working composition, it is suitable to contain a photopolymerization initiator. When the photosensitive colored curable composition is composed in positive working composition, it is preferred to contain a naphthoquinone diazide compound.

<Photopolymerization Initiator>

Hereinafter, the photopolymerization initiator used when the colored photosensitive curing composition of the invention is a negative composition will be described.

The photopolymerization initiator is not particularly limited, if it causes polymerization of the polymerizable monomer, but is preferably selected properly from the points of its properties, initiation efficiency, absorption wavelength, availability, cost, and others.

It may be added additionally to the positive system containing a naphthoquinonediazide compound, and, in such a case, it is possible to accelerate curing of the formed pattern further. Examples of the photopolymerization initiators include at least one activated halogen compounds selected from among halomethyloxadiazole compounds and halomethyl-s-triazine compounds, 3-aryl-substituted coumarin compounds, Rofin dimers, benzophenone compounds, acetophenone compounds and the derivatives thereof, cyclopentadiene-benzene-iron complexes and the salts thereof, oxime compounds, and the like Examples of the reactive halogen compounds such as the halomethyloxadiazole compounds include the 2-halomethyl-5-vinyl-1,3,4-oxadiazole compounds and others such as described in JP-B No. 57-6096; 2-trichloromethyl-5-styryl-1,3,4-oxadiazole, 2-trichloromethyl-5-(p-cyanostyryl)-1,3,4-oxadiazole, 2-trichloromethyl-5-(p-methoxy styryl)-1,3,4-oxadiazole, and the like.

Examples of the halomethyl-s-triazine compounds include the vinyl-halomethyl-s-triazine compounds such as described in JP-B No. 59-1281, the 2-(naphtho-1-yl)-4,6-bis-halomethyl-s-triazine compounds such as described in JP-A No. 53-133428; and 4-(p-aminophenyl)-2,6-di-halomethyl-s-triazine compounds.

Other examples thereof include 2,4-bis(trichloromethyl)-6-p-methoxystyryl-s-triazine, 2,6-bis(trichloromethyl)-4-(3,4-methylenedioxyphenyl)-1,3,5-triazine, 2,6-bis(trichloromethyl)-4-(4-methoxyphenyl)-1,3,5-triazine, 2,4-bis(trichloromethyl)-6-(1-p-dimethylaminophenyl-1,3-butadienyl)-s-triazine, 2-trichloromethyl-4-amino-6-p-methoxystyryl-s-triazine, 2-(naphtho-1-yl)-4,6-bis-trichloromethyl-s-triazine, 2-(4-methoxy-naphtho-1-yl)-4,6-bis-trichloromethyl-s-triazine, 2-(4-ethoxy-naphtho-1-yl)-4,6-bis-trichloromethyl-s-triazine, 2-(4-butoxy-naphtho-1-yl)-

4,6-bis-trichloromethyl-s-triazine, 2-[4-(2-methoxyethyl)-naphtho-1-yl]-4.6-bis-trichloromethyl-s-triazine, 2-[4-(2-ethoxyethyl)-naphtho-1-yl]-4,6-bis-trichloromethyl-s-triazine, 2-[4-(2-butoxyethyl)-naphtho-1-yl]-4,6-bis-trichloromethyl-s-triazine, 2-(2-methoxy-naphtho-1-yl)-4,6-bis-trichloromethyl-s-triazine, 2-(6-methoxy-5-methyl-naphtho-2-yl)-4,6-bis-trichloromethyl-s-triazine, 2-(6-methoxy-naphtho-2-yl)-4,6-bis-trichloromethyl-s-triazine, 2-(5-methoxy-naphtho-1-yl)-4,6-bis-trichloromethyl-s-triazine, 2-(4,7-dimethoxy-naphtho-1-yl)-4,6-bis-trichloromethyl-s-triazine, 2-(6-ethoxy-naphtho-2-yl)-4,6-bis-trichloromethyl-s-triazine, 2-(4,5-dimethoxy-naphtho-1-yl)-4,6-bis-trichloromethyl-s-triazine, 4-[p-N,N-di(ethoxylcarbonylmethyl)aminophenyl]-2,6-di(trichloromethyl)-s-triazine, 4-(o-methyl-p-N,N-di(ethoxycarbonylmethyl)aminophenyl)-2,6-di(trichloromethyl)-s-triazine, 4-(p-N,N-di(chloroethyl)aminophenyl)-2,6-di(trichloromethyl)-s-triazine, 4-[o-methyl-p-N,N-di(chloroethyl)aminophenyl]-2,6-di(trichloromethyl)-s-triazine, 4-(p-N-chloroethylaminophenyl)-2,6-di(trichloromethyl)-s-triazine, 4-(p-N-ethoxycarbonylmethylaminophenyl)-2,6-di(trichloromethyl)-s-triazine, 4-[p-N,N-di(phenyl)aminophenyl]-2,6-di(trichloromethyl)-s-triazine, 4-(p-N-chloroethylcarbonylaminophenyl)-2,6-di(trichloromethyl)-s-triazine, 4-[p-N-(p-methoxyphenyl)carbonylaminophenyl]-2,6-di(trichloromethyl)-s-triazine, 4-[m-N,N-di(ethoxycarbonylmethyl)aminophenyl]-2,6-di(trichloromethyl)-s-triazine, 4-[m-bromo-p-N,N-di(ethoxycarbonylmethyl)aminophenyl]-2,6-di(trichloromethyl)-s-triazine, 4-[m-chloro-p-N,N-di(ethoxycarbonylmethyl)aminophenyl]-2,6-di(trichloromethyl)-s-triazine, 4-[m-fluoro-p-N,N-di(ethoxycarbonylmethy))aminophenyl]-2,6-di(trichloromethyl)-s-triazine, 4-[o-bromo-p-N,N-di(ethoxycarbonylmethyl)aminophenyl]-2,6-di(trichloromethyl)-s-triazine, 4-[o-chloro-p-N,N-di(ethoxylcarbonylmethyl)aminophenyl]-2,6-di(trichloromethyl)-s-triazine, 4-[o-fluoro-p-N,N-di(ethoxycarbonylmethyl)aminophenyl]-2,6-di(trichloromethyl)-s-triazine, 4-[o-bromo-p-N,N-di(chloroethyl)aminophenyl]-2,6-di(trichloromethyl)-s-triazine, 4-[o-chloro-p-N,N-di(chloroethyl)aminophenyl]-2,6-di(trichloromethyl)-s-triazine, 4-[o-fluoro-p-N,N-di(chloroethyl)aminophenyl]-2,6-di(trichloromethyl)-s-triazine, 4-[m-bromo-p-N,N-di(chloroethyl)aminophenyl]-2,6-di(trichloromethyl)-s-triazine, 4-[m-chloro-p-N,N-di(chloroethyl)aminophenyl]-2,6-di(trichloromethyl)-s-triazine, 4-[m-fluoro-p-N,N-di(chloroethyl)aminophenyl]-2,6-di(trichloromethyl)-s-triazine, 4-(m-bromo-p-N-ethoxycarbonylmethylaminophenyl)-2,6-di(trichloromethyl)-s-triazine, 4-(m-chloro-p-N-ethoxycarbonylmethylaminophenyl)-2,6-di(trichloromethyl)-s-triazine, 4-(m-fluoro-p-N-ethoxycarbonylmethylaminophenyl)-2,6-di(trichloromethyl)-s-triazine, 4-(o-bromo-p-N-ethoxycarbonylmethylaminophenyl)-2,6-di(trichloromethyl)-s-triazine, 4-(o-chloro-p-N-ethoxycarbonylmethylaminophenyl)-2,6-di(trichloromethyl)-s-triazine, 4-(o-fluoro-p-N-ethoxylcarbonylmethylaminophenyl)-2,6-di(trichloromethyl)-s-triazine, 4-(m-bromo-p-N-chloroethylaminophenyl)-2,6-di(trichloromethyl)-s-triazine, 4-(m-chloro-p-N-chloroethylaminophenyl)-2,6-di(trichloromethyl)-s-triazine, 4-(m-fluoro-p-N-chloroethylaminophenyl)-2,6-di(trichloromethyl)-s-triazine, 4-(o-bromo-p-N-chloroethylaminophenyl)-2,6-di(trichloromethyl)-s-triazine, 4-(o-chloro-p-N-chloroethylaminophenyl)-2,6-di(trichloromethyl)-s-triazine, 4-(o-fluoro-p-N-chloroethylaminophenyl)-2,6-di(trichloromethyl)-s-triazine, and the like.

Other useful examples thereof include TAZ series products (e.g., TAZ-107, TAZ-110, TAZ-104, TAZ-109, TAZ-140, TAZ-204, TAZ-113, TAZ-123, etc.) manufactured by Midori Kagaku Co., Ltd.; T series products (e.g., T-OMS, T-BMP, T-R, T-B, etc.) manufactured by PANCHIM; IRGACURE series products (e.g., IRGACURE 369, IRGACURE 784, IRGACURE 651, IRGACURE 184, IRGACURE 500, IRGACURE 1000, IRGACURE 149, IRGACURE 819, IRGACURE 261, etc.); DAROCUR series products (e.g., DAROCUR 1173, etc.) manufactured by Ciba Specialty Chemicals; 4,4'-bis(diethylamino)-benzophenone, 2-(O-benzoyloxime)-1-[4-(phenylthio)phenyl]-1,2-octandione, 1-(O-acetyloxime)-1-[9-ethyl-6-(2-methylbenzoyl)-9H-carbazole-3-yl]ethane, 2-benzyl-2-dimethyl amino-4-morpholinobutylophenone, 2,2-dimethoxy-2-phenylacetophenone, 2-(o-chlorophenyl)-4,5-diphenylimidazolyl dimer, 2-(o-fluorophenyl)-4,5-diphenylimidazolyl dimer, 2-(o-methoxyphenyl)-4,5-diphenylimidazolyl dimer, 2-(p-methoxyphenyl)-4,5-diphenylimidazolyl dimer, 2-(p-dimethoxyphenyl)-4,5-diphenylimidazolyl dimer, 2-(2,4-dimethoxyphenyl)-4,5-diphenylimidazolyl dimer, 2-(p-methyl mercaptophenyl)-4,5-diphenylimidazolyl dimer, benzoin isopropylether, and the like.

In addition to the photopolymerization initiators described above, the photosensitive colored curable composition according to the invention may contain other known photopolymerization initiators. Specific examples thereof include the vicinal polyketol aldonyl compounds described in U.S. Pat. No. 2,367,660; the α-carbonyl compounds described in U.S. Pat. Nos. 2,367,661 and 2,367,670; the acyloin ethers described in U.S. Pat. No. 2,448,828; the α-hydrocarbon-substituted aromatic acyloin compounds described in U.S. Pat. No. 2,722,512; the polynuclear quinone compounds described in U.S. Pat. Nos. 3,046,127 and 2,951,758; the combination of triallylimidazole dimer and p-aminophenylketone described in U.S. Pat. No. 3,549,367; the benzothiazole compounds and trihalomethyl-s-triazine compounds described in JP-B No. 51-48516; and the like.

The content of the photopolymerization initiator in the colored photosensitive curing composition is preferably 0.01 to 50% by mass, more preferably 1 to 30% by mass, and particularly preferably 1 to 20% by mass, with respect to the solid content of the polymerization monomer. It is possible to carry out polymerization favorably and obtain a film having favorable film strength, when the content is in the range above.

The photopolymerization initiator may be used in combination with a sensitizer and a photostabilizer.

Examples thereof include benzoin, benzoin methyl ether, 9-fluorenone, 2-chloro-9-fluorenone, 2-methyl-9-fluorenone, 9-anthrone, 2-bromo-9-anthrone, 2-ethyl-9-anthrone, 9,10-anthraquinone, 2-ethyl-9,10-anthraquinone, 2-t-butyl-9,10-anthraquinone, 2,6-dichloro-9,10-anthraquinone, xanthone, 2-methylxanthone, 2-ethylxanthone, 2-methoxyxanthone, 2-ethoxyxanthone, thioxanthone, 2,4-diethylthioxanthone, acridone, 10-butyl-2-chloroacridone, benzyl, dibenzalacetone, p-(dimethylamino)phenyl styryl ketone, p-(dimethylamino)phenyl-p-methyl styryl ketone, benzophenone, p-(dimethylamino)benzophenone (or Michler's ketone), p-(diethylamino)benzophenone, benzoanthrone, a benzothiazole compound described in JP-B No. 51-48516, and TINUVIN 1130 and TINUVIN 400.

Other known photopolymerization initiators than such photopolymerization initiators as described above may be used in the negative dye-containing curable composition of the present invention.

In addition to the components above, a heat-polymerization inhibitor is preferably added, and useful examples thereof include hydroquinone, p-methoxyphenol, di-t-butyl-p-cresol, pyrogallol, t-butylcatechol, benzoquinone, 4,4'-thiobis(3-methyl-6-t-butylphenol), 2,2'-methylene bis(4-methyl-6-t-butylphenol), 2-mercaptobenzimidazole, and the like.

Naphthoquinone Diazide Compound

Next, the naphthoquinone diazide compound that can be contained in the photosensitive colored curable composition of the invention when the composition is of positive type will be described.

The naphthoqinone diazide compound is a compound having at least one o-quinone diazide group, and specific examples thereof include o-naphthoquinonediazide-5-sulfonic ester, o-naphthoquinonediazide-5-sulfonic amide, o-naphthoquinonediazide-4-sulfonic ester, and o-naphthoquinonediazide-4-sulfonic amide. These ester and amide compounds can be prepared, for example, by a known method using a phenol compound represented by Formula (I) described in JP-A Nos. 2-84650 and 3-49437.

When the colored photosensitive curing composition of the invention is made to be a positive composition, the alkali-soluble phenol resin and the crosslinking agent are normally, preferably dissolved in an organic solvent respectively at approximately 2 to 50% by mass and approximately 2 to 30% by mass. The contents of the naphthoquinonediazide compound and the colorant are normally, respectively approximately 2 to 30% by mass and 2 to 50% by mass in the solutions of the binder and the crosslinking agent.

<Solvent>

Generally in preparation of the colored photosensitive curing composition of the invention, a solvent may be contained in the composition. The solvent for use is not particularly limited, if it satisfies the requirement in solubility of respective components in the composition and the coating property of the colored photosensitive curing composition, but preferably selected properly, by taking the solubility of binder and the coating property and stability of the dispersion into consideration. Preferred examples of the solvent include an ester compound, such as an alkyl ester, e.g., ethyl acetate, n-butyl acetate, isobutyl acetate, amyl formate, isoamyl acetate, isobutyl acetate, butyl propionate, isopropyl butyrate, ethyl butyrate, butyl butyrate, an alkyl ester compound, methyl lactate, ethyl lactate, methyl oxyacetate, ethyl oxyacetate, butyl oxyacetate, methyl methoxyacetate, ethyl methoxyacetate, butyl methoxyacetate, methyl ethoxyacetate and ethyl ethoxyacetate; a 3-oxypropionic acid alkyl ester, such as methyl 3-oxypropionate and ethyl 3-oxypropionate, for example, methyl 3-methoxypropionate, ethyl 3-methoxypropionate, methyl 3-ethoxypropionate and ethyl 3-ethoxypropionate, a 2-oxypropionic acid alkyl ester, such as methyl 2-oxypropionate, ethyl 2-oxypropionate and propyl 2-oxypropionate, for example, methyl 2-methoxypropionate, ethyl 2-methoxypropionate, propyl 2-methoxypropionate, methyl 2-ethoxypropionate, ethyl 2-ethoxypropionate, methyl 2-oxy-2-methylpropionate, ethyl 2-oxy-2-methylpropionate, methyl 2-methoxy-2-methylpropionate and ethyl 2-ethoxy-2-methylpropionate, methyl pyruvate, ethyl pyruvate, propyl pyruvate, methyl acetoacetate, ethyl acetoacetate, methyl 2-oxobutanoate and ethyl 2-oxobutanoate; an ether compound, such as diethylene glycol dimethyl ether, tetrahydrofuran, ethylene glycol monomethyl ether, ethylene glycol monoethyl ether, methylcellosolve acetate, ethylcellosolve acetate, diethylene glycol monomethyl ether, diethylene glycol monoethyl ether, diethylene glycol monobutyl ether, propylene glycol methyl ether, propylene glycol methyl ether acetate, propylene glycol ethyl ether acetate, propylene glycol propyl ether acetate, ethylcarbitol acetate and butylcarbitol acetate; a ketone compound, such as methyl ethyl ketone, cyclohexanone, 2-heptanone and 3-heptanone, and an aromatic hydrocarbon compound, such as toluene and xylene.

Among these, methyl 3-ethoxypropionate, ethyl 3-ethoxypropionate, ethylcellosolve acetate, ethyl lactate, diethylene glycol dimethyl ether, butyl acetate, methyl 3-methoxypropionate, 2-heptanone, cyclohexanone, ethylcarbitol acetate, butylcarbitol acetate, propylene glycol methyl ether and propylene glycol methyl ether acetate are more preferred.

<Various Additive>

The colored photosensitive curing composition of the invention may contain as needed various additives such as filler, polymer compound other than those above, surfactant, adhesion accelerator, antioxidant, ultraviolet absorbent, and aggregation inhibitor.

Specific examples of the various additives include fillers such as glass and alumina; polymer compounds other than binder resins such as polyvinylalcohol, polyacrylic acid, polyethylene glycol monoalkylethers, and polyfluoroalkyl acrylates; nonionic, cationic, anionic, and other surfactants; adhesion accelerators such as vinyltrimethoxysilane, vinyltriethoxysilane, vinyltris(2-methoxyethoxy)silane, N-(2-aminoethyl)-3-aminopropylmethyldimethoxysilane, N-(2-aminoethyl)-3-aminopropyltrimethoxysilane, 3-aminopropyltriethoxysilane, 3-glycidoxypropyltrimethoxysilane, 3-glycidoxypropylmethyldimethoxysilane, 2-(3,4-epoxycyclohexyl)ethyltrimethoxysilane, 3-chloropropylmethyldimethoxysilane, 3-chloropropyltrimethoxysilane, 3-methacryloxypropyltrimethoxysilane, and 3-mercaptopropyltrimethoxysilane; antioxidants such as 2,2-thiobis(4-methyl-6-t-butylphenol) and 2,6-di-t-butylphenol: ultraviolet absorbents such as 2-(3-t-butyl-5-methyl-2-hydroxyphenyl)-5-chlorobenzotriazolyl, and alkoxybenzophenones; and aggregation inhibitors such as sodium polyacrylate; and the like.

An organic carboxylic acid, preferably a low-molecular-weight organic carboxylic acid having a molecular weight of 1,000 or less, may be added to the composition, for acceleration of alkaline solubilization of the region to be developed and removed (e.g., uncured region in the case of negative composition) and further improvement in the printing efficiency of the colored photosensitive curing composition of the invention.

Specific examples thereof include fatty monocarboxylic acids such as formic acid, acetic acid, propionic acid, butyric acid, valeric acid, pivalic acid, caproic acid, diethylacetic acid, enanthic acid, and caprylic acid; fatty dicarboxylic acids such as oxalic acid, malonic acid, succinic acid, glutaric acid, adipic acid, pimelic acid, suberic acid, azelaic acid, sebacic acid, brassic acid, methylmalonic acid, ethylmalonic acid, dimethylmalonic acid, methylsuccinic acid, tetramethylsuccinic acid, and citraconic acid; aliphatic tricarboxylic acids such as tricarballylic acid, aconitic acid, and camphoronic acid; aromatic monocarboxylic acids such as benzoic acid, toluic acid, cuminic acid, hemellitic acid, and mesitylene acid; aromatic polycarboxylic acids such as phthalic acid, isophthalic acid, terephthalic acid, trimellitic acid, trimesic acid, mellophanic acid, and pyromellitic acid; other carboxylic acids such as phenylacetic acid, hydratropic acid, hydrocinnamic acid, mandelic acid, phenylsuccinic acid, atropic acid, cinnamic acid, methyl cinnamate, benzyl cinnamate, cinnamylideneacetic acid, coumalic acid, and umbellic acid.

The colored photosensitive curing composition of the invention may be used favorably in applications for color image generation, for example as a color filter for liquid crystal display elements (LCDs) and solid-state image sensing devices (e.g., charge coupled devices (CCDs) and CMOSs) and also in applications for producing printing ink, inkjet ink, paint, and the like. It is used particularly favorably for color image generation in charge coupled devices (CCDs), and solid-state image sensing devices such as CMOS.

<<Color Filter and Production Method Thereof>>

The method of producing the color filter of the invention will be described below in detail. In preparation of the color filter of the invention, the colored photosensitive curing composition of the invention described above is used. In preparation of the color filter of the invention, a negative or positive colored pattern (resist pattern) is formed by forming a radiation-sensitive composition layer by coating the colored photosensitive curing composition of the invention on a substrate by an application method such as spin coating, cast coating, or roll coating, irradiating the coated layer with light through a particular mask pattern, and developing the resulting layer with a developing solution.

The light source for use in irradiating the colored photosensitive curing composition for color filter of the invention is not particularly limited, if it is a light source emitting a light at a wavelength of 400 nm or less, and examples thereof include lamp light sources such as xenon lamp, halogen lamp, tungsten lamp, high-pressure mercury lamp, ultrahigh-pressure mercury lamp, metal halide lamp, medium-pressure mercury lamp, low-pressure mercury lamp, carbon arc, and fluorescent lamp; Ar ion lasers (364 nm, 351 nm, 10 mW to 1W), Kr ion lasers (356 nm, 351 nm, 10 mW to 1W), solid state lasers such as combinations of Nd:YAG (YVO4) and SHG crystal×2 (355 nm, 5 mW to 1W), a wave-guided wavelength-converting device and AlGaAs, and a wave-guided wavelength-converting device and an AlGaInP or AlGaAs semiconductor (300 nm to 350 nm, 5 mW to 100 mW); others pulsed lasers such as $N_2$ laser (337 nm, pulse: 0.1 to 10 mJ) and XeF (351 nm, pulse: 10 to 250 mJ); and the like, and an optical filter may be used when only a light at a particular wavelength is used. Alternatively, ultraviolet ray such as from ArF excimer laser (wavelength 193 nm), KrF excimer laser (wavelength 248 nm), or i-ray (wavelength 365 nm) may be used. A light source particularly favorable from the viewpoints of cost and light-exposure energy is ultraviolet ray, and an example thereof is i-ray.

A curing step of curing the formed pattern as needed by heating and/or photoirradiation may be installed additionally. A radiation ray such as i-ray is used particularly favorably as the light or radiation ray used then.

In production of the color filter of the invention, it is possible to prepare a color filter in a desired number of colors, by repeating the image-forming step (and as needed curing step) multiple times according to the desired number of colors in the case of a negative color filter and by repeating the image-forming step and the post-baking step multiple times according to the desired number of colors in the case of a positive color filter.

Examples of the substrates for use include soda-lime glass, Pyrex (registered tradename) glass, and quartz glass used, for example, in liquid-crystal display elements; and those having a transparent conductive film formed thereon, photoelectric converting device substrates, such as silicon substrate, used for example in image sensors; complimentary metal oxide semiconductors (CMOS); and the like. The substrate may have a black stripe formed thereon for separation of pixels.

In addition, an undercoat layer may be formed on the substrate as needed, from the viewpoint of improvement in adhesiveness to the upper layer, prevention of material diffusion, or flattening of the substrate surface.

Any solution may be used as the developing solution for use in production of the color filter of the invention, if it is a composition that dissolves the region of the colored photosensitive curing composition of the invention to be developed and removed (uncured region in the case of a negative composition) and does not dissolve the other region (cured region in the case of a negative composition). Specifically, a combination of organic solvents or an aqueous alkaline solution is used favorably. Examples of the organic solvents for use include those used in production of the composition of the invention described above.

The aqueous alkaline solution is, for example, a solution containing an alkaline compound such as sodium hydroxide, potassium hydroxide, sodium carbonate, sodium silicate, sodium metasilicate, ammonia water, ethylamine, diethylamine, dimethylethanolamine, tetramethylammonium hydroxide, tetraethylammonium hydroxide, choline, pyrrole, piperidine, or 1,8-diazabicyclo-[5.4.0]-7-undecene at a concentration of 0.001 to 10% by mass, preferably 0.01 to 1% by mass. When such an aqueous alkaline solution is used as the developing solution, the color filter is generally washed with water after development.

The color filter of the invention is used favorably in liquid crystal display elements and solid-state image sensing devices such as charge coupled device (CCD), particularly in high-resolution charge coupled devices (CCD) and CMOS devices at a resolution of 1,000,000 pixels or more. The color filter of the invention may also be used, for example, as a color filter placed between the light-receiving unit and the photoconverging microlens in each pixel for charge coupled device (CCD).

EXAMPLES

Hereinafter, the invention will be described specifically with reference to Examples, however it should be understood that the invention is not limited thereby.

Example 1

Intermediates 4, 5, and 11 (compounds represented by Formula (IV)), and exemplary compounds shown below were synthesized along the reaction scheme A to C described above according to the synthesis method described above. The molar absorption coefficient of each synthesized exemplary compound was determined in ethyl acetate solution (by using a spectrophotometer UV-2400PC (manufactured by Shimadzu Corporation)), and the maximum absorption wavelength (λmax) and the molar absorption coefficient (ε) are summarized in the following Table 4. The absorbance (Abs) of each colorant at 450 nm was evaluated, as normalized with respect to 1.0 of the absorbance at the measurement maximum absorption wavelength (λmax). Results are summarized in Table 4.

TABLE 4

| Exemplary compound | $\lambda_{max}$ | $\epsilon$ | Abs. at 450 nm, normalized to Abs. = 1.0 at $\lambda$max |
|---|---|---|---|
| III-1 | 533.1 | 130000 | 0.0125 |
| III-45 | 546.7 | 128300 | 0.0068 |
| III-70 | 540.0 | 126000 | 0.0068 |
| III-80 | 540.0 | 123000 | 0.0100 |
| II-5 | 514.6 | 80700 | 0.1300 |
| I-1 | 558.3 | 129000 | 0.0096 |
| I-2 | 578.3 | 122500 | 0.0041 |
| I-4 | 540.0 | 119000 | 0.0079 |
| I-6 | 536.6 | 104000 | 0.0230 |
| I-8 | 524.0 | 78900 | 0.1200 |
| I-30 | 550.5 | 200000 | 0.0160 |
| I-32 | 571.2 | 195800 | 0.0050 |
| I-33 | 573.2 | 168000 | 0.0100 |

The results in Table 4 show that the metal complex compounds of the invention are higher in molar absorption coefficient and have a favorable absorbance at 450 nm. In particular, the compound represented by Formula (III) is a compound having an extremely lower transmittance at 450 nm that is superior in color-separating potential.

Example 2

1) Preparation of Resist Solution

Propylene glycol monomethylether acetate (PGMEA) 19.20 parts
Ethyl lactate 36.67 parts
Binder (benzyl methacrylate/methacrylic acid/2-hydroxyethyl methacrylate) copolymer (molar ratio: 60:20:20) 41% EL solution 30.51 parts
Dipentaerythritol hexaacrylate 12.20 parts
Polymerization inhibitor (p-methoxyphenol) 0.0061 parts
Fluorochemical surfactant 0.83 parts
Photopolymerization initiator TAZ-107 (manufactured by Midori Kagaku Co., Ltd.) 0.586 parts These components were blended and solubilized, to give a resist solution.

2) Preparation of Glass Substrate Having an Undercoat Layer

A glass substrate (Corning 1737) was ultrasonicated in 0.5% aqueous NaOH solution, dehydrated, and baked (200° C./20 minutes).

The resist solution 1) above was then applied on a clean glass substrate to a film thickness of 2.0 μm by a spin coater, and the plate was dried under heat at 220° C. for 1 hour, to give a cured film (undercoat layer).

3) Preparation of Colored Resist Solution ([Negative] Colored Ultraviolet-Sensitive Curing Composition)

9.4 g of the resist solution obtained in 1) above and 0.35 g of a dipyrromethene-based complex compound of the invention, exemplary compound III-1 (compound represented by Formula (III)) described above, were mixed, and the mixture was dissolved, to give a coloring resist solution ([negative] colored ultraviolet-sensitive curing composition solution).

4) Preparation of Resist Film

The coloring resist solution obtained in 3) above was applied on the undercoat layer formed on the glass substrate having an undercoat layer obtained in 2) to a film thickness of 1.0 μm by a spin coater, and the substrate was prebaked at 100° C. for 120 seconds, to give a monochromic color filter.

5) Evaluation

The storage stability of the colored resist solution thus prepared and the spectroscopic properties of the coated film formed on the glass substrate with the coloring resist solution were evaluated. Evaluation results are summarized in the following shown in Table 5.

—Storage Stability—

Deposition of foreign matters in the coloring resist solution after storage at room temperature for one month was evaluated by visual observation according to the following criteria:
<Criteria>
A: No deposition
B: Slight deposition
C: Distinct deposition —Evaluation of Transmittance—

The transmission spectrum of the color filter thus formed was obtained, and the transmittance at 450 nm determined. A larger transmittance means greater transmission of blue light, indicating that the colorant is favorable as a magenta to violet colorant usable for use in blue filter.
<Criteria>
The transmittance at 450 nm of each colorant was determined, when the transmittance of each colorant at the maximum absorption wavelength was corrected (normalized) to 2%.
A: Transmittance at 450 nm≥90%
B: 80≤Transmittance at 450 nm<90
C: transmittance at 450 nm<80%

Examples 3 to 30

Resist films were prepared similarly to Example 2, except that the exemplary compound III-1 used in preparation of the coloring resist solution 3) in Example 2 was replaced with the exemplary compound shown in the following Table 5 in an amount equimolar to (Examples 3 to 26) or half molar of the compound III-1 (Examples 27 to 30). Results are summarized in Table 5.

Comparative Examples 1 to 3

Resist films were prepared similarly to Example 2, except that the exemplary compound III-1 used in preparation of the coloring resist solution 3) in Example 2 was replaced with the compound shown in the following Table 5. Results are summarized in Table 5.

TABLE 5

| | Exemplary compound | Transmittance at 450 nm | Storage stability |
|---|---|---|---|
| Example 2 | III-1 | A | A |
| Example 3 | III-2 | A | A |
| Example 4 | III-3 | A | A |
| Example 5 | III-5 | A | A |
| Example 6 | III-7 | A | A |
| Example 7 | III-9 | A | A |
| Example 8 | III-10 | A | A |
| Example 9 | III-16 | A | A |
| Example 10 | III-17 | A | A |
| Example 11 | III-20 | A | A |
| Example 12 | III-23 | A | A |
| Example 13 | III-30 | A | A |
| Example 14 | III-31 | A | A |
| Example 15 | III-36 | A | A |
| Example 16 | III-45 | A | A |
| Example 17 | III-51 | A | A |
| Example 18 | III-52 | A | A |
| Example 19 | III-54 | A | A |
| Example 20 | III-63 | A | A |
| Example 21 | III-70 | A | A |
| Example 22 | III-74 | A | A |
| Example 23 | III-79 | A | A |

TABLE 5-continued

|  | Exemplary compound | Transmittance at 450 nm | Storage stability |
|---|---|---|---|
| Example 24 | III-80 | A | A |
| Example 25 | III-83 | A | A |
| Example 26 | III-84 | A | A |
| Example 27 | I-1 | B | B |
| Example 28 | I-2 | A | B |
| Example 29 | I-30 | B | B |
| Example 30 | I-32 | B | B |
| Comparative Example 1 | C.I. Acid Violet 17 | C | C |
| Comparative Example 2 | C.I. Acid Violet 49 | C | C |
| Comparative Example 3 | C.I. Acid Blue 83 | C | C |

The results in Table 5 showed that the blue colored ultraviolet sensitive curing compositions using the colorant of the invention had superior storage life as resist solution and gave coated films favorable as a color filter having favorable blue spectroscopic properties (color separation). The coated films were superior in heat resistance and light stability and had favorable image-forming property.

Example 31

A) Preparation of Blue Resist Solution ([Negative] Colored Ultraviolet-Sensitive Curing Composition)

The compounds in the following composition were mixed, and the mixture was dissolved to give a colored ultraviolet-sensitive photosensitive resin composition A-2.

<Colored Ultraviolet-Sensitive Photosensitive Resin Composition A-2>
Cyclohexanone 80 parts
Exemplary compound (III-1) 3.84 parts
Exemplary compound (CB-34) 8.16 parts
KARAYAD DPHA (polymerizable compound: manufactured by Nippon Kayaku Co., Ltd.) 5.89 parts
Photopolymerization initiator (CGI-242 (manufactured by Ciba Specialty Chemicals)) 1.50 parts
Dicyclohexylmethylamine 0.61 parts
Surfactant (F-781, manufactured by Dainippon Ink and Chemicals Inc.) 0.02 parts B) Application, Exposure, and Development of Blue Resist Solution ([Negative] Colored Ultraviolet-Sensitive Curing Composition)

The colored ultraviolet-sensitive photosensitive resin composition A-2 prepared in A) above was applied on the undercoat layer of the glass substrate having an undercoat layer obtained in 2) above to a dry film thickness of 1.0 µm, to give a photocurable coated film. The film was heat-treated (prebaked) on a hot plate at 100° C. for 120 seconds, to give a blue filter.

Then, a light at a wavelength of 365 nm was irradiated on the coated film through a mask having a line width of 20 µm at an exposure intensity of 500 mJ/cm$^2$, by using a photoirradiation device. After exposure, the image was developed under a condition at 25° C. for 40 seconds by using 60% CD-2000 developing solution (manufactured by Fujifilm Electronic Materials Co., Ltd.). The substrate was then washed with running water for 30 seconds and spray-dried, to give a pattern favorable for color filter.

C) Evaluation

The storage stability of the colored ultraviolet-sensitive photosensitive resin composition A-2 thus prepared and the heat resistance and the light stability of the coated film coated on a glass substrate were determined in the following manner. Evaluation results are summarized in the following Table 6.

<Storage Stability>

Deposition of foreign matters in the colored ultraviolet-sensitive photosensitive resin composition A-2 after storage at room temperature for one month was evaluated by visual observation according to the following criteria:
—Criteria—
A: No deposition
B: Slight deposition
C: Distinct deposition <Heat Resistance>

A glass substrate carrying the coated film of the colored ultraviolet-sensitive photosensitive resin composition A-2 was heated on a hot plate at 200° C. for 1 hour, and the difference in color ΔEab between before and after the heat-resistance test was determined by using a chromoscope MCPD-1000 (manufactured by Otsuka Electronics Co., Ltd.) and evaluated according to the following criteria. A smaller ΔEab value indicates that the heat resistance is more favorable.
—Criteria—
A: ΔEab<5 or less
B: 5≤ΔEab<: 10
C: 10<ΔEab <Light Stability>

Light from a xenon lamp was irradiated at an intensity of 50,000 luxes for 20 hours (equivalent to 1,000,000 lux·h) on the glass substrate carrying the coated film of the colored ultraviolet-sensitive photosensitive resin composition A-2, and the difference ΔEab in color between before and after the light-resistance test was determined. A smaller ΔEab value indicates that the light stability is more favorable.
—Criteria—
A: ΔEab<3
B: 3≤ΔEab≤10
C: 10<ΔEab Examples 32 to 63

A test was performed in a similar manner to Example 31, except that exemplary compounds III-1 and CA-34 used in preparation of the colored ultraviolet-sensitive photosensitive resin composition A-2 in Example 31 were replaced respectively with the equimolar amount of the colorants shown in the following Table 6. (however, each of III-70 and I-23 in Example 50, each of III-80 and I-23 in Example 51, each of III-81 and I-23 in Example 52, and I-32 in Example 48 were used in a half molar amount). Results are summarized Table 6.

TABLE 6

|  | Exemplary compound | Exemplary compound | Storage life | Heat resistance | Light stability |
|---|---|---|---|---|---|
| Example 31 | III-1 | CB-34 | A | A | B |
| Example 32 | III-17 | " | A | A | B |
| Example 33 | III-30 | " | A | A | A |
| Example 34 | III-36 | " | A | A | A |
| Example 35 | III-51 | " | A | A | A |
| Example 36 | III-52 | " | A | A | A |
| Example 37 | III-54 | " | B | A | A |
| Example 38 | III-70 | " | B | A | A |
| Example 39 | III-81 | " | A | A | A |
| Example 40 | III-83 | " | B | A | A |
| Example 41 | III-84 | " | A | A | A |
| Example 42 | III-89 | " | B | A | A |
| Example 43 | III-97 | " | B | A | A |
| Example 44 | III-101 | " | B | A | A |
| Example 45 | II-11 | " | B | A | B |
| Example 46 | I-23 | " | A | A | A |

TABLE 6-continued

| | Exemplary compound | Exemplary compound | Storage life | Heat resistance | Light stability |
|---|---|---|---|---|---|
| Example 47 | I-26 | " | A | A | A |
| Example 48 | I-32 | " | A | B | B |
| Example 49 | III-17 | CF-33 | A | A | A |
| Example 50 | III-70 I-23 | " | A | A | A |
| Example 51 | III-80 I-23 | " | A | A | A |
| Example 52 | III-81 I-23 | " | A | A | A |
| Example 53 | III-82 | " | A | A | A |
| Example 54 | III-83 | " | A | A | A |
| Example 55 | III-85 | " | A | A | A |
| Example 56 | I-23 | " | A | A | A |
| Example 57 | III-84 | CB-5 | A | A | A |
| Example 58 | " | CE-38 | A | A | A |
| Example 59 | " | CG-19 | A | A | A |
| Example 60 | " | CG-34 | A | A | A |
| Example 61 | " | CG-46 | A | A | A |
| Example 62 | " | CD-4 | B | B | B |
| Example 63 | III-70 | " | B | B | B |

The blue colored ultraviolet sensitive curing compositions using the colorant of the invention had favorable storage life as the resist solution and gave coated films favorable as a color filter having favorable blue spectroscopic properties (color separation). The coated films were superior in heat resistance and light stability and had favorable image-forming property.

Examples 64 to 96

—Application, Exposure, and Development of Resist Solution (Image Formation)—

1) Preparation of Silicon Wafer Substrate Having an Undercoat Layer

A 6-inch silicon wafer was heat-treated in an oven at 200° C. for 30 minutes. The resist solution prepared in 1) of Example 1 was then applied on the silicon wafer to a dry film thickness of 1.0 µm and dried in an oven at 220° C. additionally for one hour to form an undercoat layer, giving a silicon wafer substrate having an undercoat layer.

Each of the colored ultraviolet-sensitive curing compositions used in Examples 31 to 63 was coated on the undercoat layer of the silicon wafer substrate having an undercoat layer obtained in 1) above to a dry film thickness of 0.6 µm to form a photocurable coated film. The film was heat-treated (prebaked) on a hot plate at 100° C. for 120 seconds. Then, a light at a wavelength of 365 nm was irradiated through a 1.2 µm-square island-patterned mask at an exposure intensity varying in the range of 100 to 2,500 mJ/cm$^2$ at an interval of 100 mJ/cm$^2$, by using an i-ray stepper photoirradiation apparatus FPA-3000i5+ (manufactured by Canon Inc.). The silicon wafer substrate carrying the irradiated coated film formed was then placed on a horizontal revolving table of a spin/shower developing machine (DW-30, manufactured by Chemitronics Co., Ltd.), and then, paddle-developed at 23° C. 60 seconds in CD-2000 (manufactured by Fujifilm Electronic Materials Co., Ltd.), to form a blue colored pattern on the silicon wafer substrate.

—Preparation of Color Filter—

The silicon wafer substrate having the formed colored pattern was connected to the above-described horizontal revolving table in the vacuum chuck mode and rotated at a rotational frequency of 50 rpm by a rotating device while washed with purified water sprayed onto the rotational center from above, and then, dried, to give a color filter.

The blue pattern image formed had a profile favorable for image sensor, in which a line having a cross section definitely in the rectangular shape was formed as designed.

Example 97

1) Preparation of [Positive] Colored Ultraviolet-Sensitive Curing Composition
Ethyl lactate (EL) 30 parts
Following resin P-1 3.0 parts
Following naphthoquinonediazide compound N-1 1.8 parts
Crosslinking agent: hexamethoxymethylolated melamine 0.6 parts
Photochemical acid generator: TAZ-107 (manufactured by Midori Kagaku Co., Ltd.) 1.2 parts
Fluorochemical surfactant (F-475 Dainippon Ink and Chemicals, Inc.) 0.0005 parts
Colorant: exemplary compound III-1 (compound represented by Formula (III)) 0.3 parts
Colorant: exemplary compound CB-34 (compound represented by Formula (B)) 0.8 parts The components above were blended, and the mixture was dissolved to give a [positive] colored ultraviolet-sensitive curing composition.

Evaluation of the storage stability, heat resistance and light stability of the colorant-containing positive-type curing composition using the dye of the invention in a similar manner to Example 31 showed that the composition was superior in storage stability and heat resistance and also favorable in light stability. Thus, it was possible to obtain a blue filter superior in transmittance and color separation.

The resin P-1 and the naphthoquinonediazide compound (N-1) were synthesized in the following manners.

2) Synthesis of Resin P-1

70.0 g of benzyl methacrylate, 13.0 g of methacrylic acid, 17.0 g of 2-hydroxyethyl methacrylate, and 600 g of 2-methoxypropanol were placed in a three-neck flask which was attached with a stirrer, a reflux condenser tube, and thermometer. The mixture was mixed with a catalytic quantity of a polymerization initiator (trade name: V-65, made by Wako Pure Chemical Industries, Inc.), and was stirred for 10 hours at 65° C. in a nitrogen stream. The resin solution obtained was dripped into 20 L of ion-exchange water with vigorous stirring, and a white powder was obtained. The white powder was dried at 40° C. for 24 hours in a vacuum, and 145 g of resin P-1 was obtained. The molecular weight was measured by GPC, which showed the weight average molecular weight Mw=28,000, and number average molecular weight Mn=11,000.

3) Synthesis of Naphthoquinone Diazide Compound (N-1)

42.45 g of Trisp-PA (made by Honshu Chemical Co.), 61.80 g of o-naphthoquinone diazide-5-sulfonylchloride, and 300 ml of acetone were placed in a three-neck flask, into which 24.44 g of triethylamine was added dropwise at room temperature for 1 hour. After the dripping, it was stirred for another 2 hours. Then, the reaction solution was poured into a large volume of water with stirring. Precipitated naphthoquinone diazide sulfonic acid ester was collected by suction filtration, and dried in a vacuum at 40° C. for 24 hours, to obtain photosensitive compound N-1.

The invention provides a compound useful for color filters in primary colors, blue, green, and red, having a high absorption coefficient allowing reduction in thickness thereof that are superior in color purity and fastness, and a tautomer thereof, a metal complex compound and a colored photosensitive curing composition containing the metal complex compound.

The invention also provides a blue-colored photosensitive curing composition having a high absorption coefficient allowing the reduction in thickness thereof that is superior in blue color purity and fastness.

The invention also provides a color filter that allows reduction in the thickness thereof and is superior in color purity and fastness, and a method of producing the same.

Further the invention provides the following items of <1> to <14>;

<1> A colored photosensitive curing composition, comprising, as a colorant, a dipyrromethene-based metal complex compound obtained from a metal or metal compound and a dipyrromethene-based compound represented by the following Formula (I):

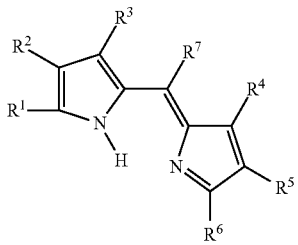

Formula (I)

wherein in Formula (I), $R^1$ to $R^6$ each independently represents a hydrogen atom or a substituent group; and $R^7$ represents a hydrogen or halogen atom, or an alkyl, aryl or heterocyclic group.

<2> The colored photosensitive curing composition of the item <1>, wherein the dipyrromethene-based metal complex compound is a compound represented by the following Formula (II-1):

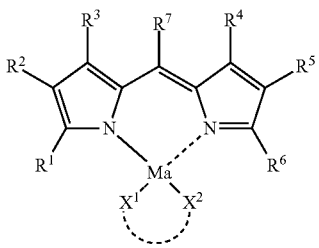

Formula (II-1)

wherein in Formula (II-1), $R^1$ to $R^6$ each independently represents a hydrogen atom or a substituent group; $R^7$ represents a hydrogen or halogen atom, or an alkyl, aryl or heterocyclic group; Ma represents a metal or metal compound; $X^2$ represents a group needed for neutralization of the electric charge of Ma; $X^1$ represents a group that can bind to Ma; and $X^1$ and $X^2$ may bind to each other to form a five-, six-, or seven-membered ring.

<3> The colored photosensitive curing composition of the item <2>, wherein the dipyrromethene-based metal complex compound is a compound represented by the following Formula (II-2):

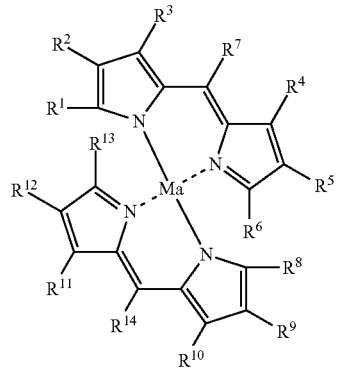

Formula (II-2)

wherein in Formula (II-2), $R^1$ to $R^6$, and $R^8$ to $R^{13}$ each independently represents a hydrogen atom or a substituent group; $R^7$ and $R^{14}$ each independently represents a hydrogen or halogen atom, or an alkyl, aryl or heterocyclic group; and Ma represents a metal or metal compound.

<4> The colored photosensitive curing composition of the item <1>, wherein the dipyrromethene-based metal complex compound is a compound represented by the following Formula (III):

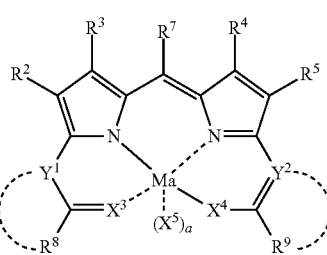

Formula (III)

wherein in Formula (III), $R^2$ to $R^5$ each independently represents a hydrogen atom or a substituent group; $R^7$ represents a hydrogen or halogen atom, or an alkyl, aryl or heterocyclic group; Ma represents a metal or metal compound; $X^3$ represents NR (wherein, R represents a hydrogen atom or an alkyl, alkenyl, aryl, heterocyclic, acyl, alkylsulfonyl, or arylsulfonyl group) or a nitrogen, oxygen or sulfur atom; $X^4$ represents NRa (wherein, Ra represents a hydrogen atom or an alkyl, alkenyl, aryl, heterocyclic, acyl, alkylsulfonyl, or arylsulfonyl group) or an oxygen or sulfur atom; $Y^1$ represents NRc (wherein, Rc represents a hydrogen atom or an alkyl, alkenyl, aryl, heterocyclic, acyl, alkylsulfonyl, or arylsulfonyl group) or a nitrogen or carbon atom; $Y^2$ represents a nitrogen or carbon atom; $R^8$ and $R^9$ each independently represent an alkyl, alkenyl, aryl, heterocyclic, alkoxy, aryloxy, alkylamino, arylamino, or heterocyclic amino group; $R^8$ and $Y^1$ may bind to each other to form a five-, six-, or seven-membered ring; $R^9$ and $Y^2$ may bind to each other to form a five-, six-, or seven-membered ring; $X^5$ represents a group that can bind to Ma; and a is 0, 1, or 2.

<5> The colored photosensitive curing composition of any one of the items <1> to <4>, wherein the metal or metal compound is Fe, Zn, Co, V=O, or Cu.

<6> The colored photosensitive curing composition of any one of the items <1> to <5>, further comprising a tetraazaporphyrin-based cyan colorant represented by the following Formula (A):

Formula (A)

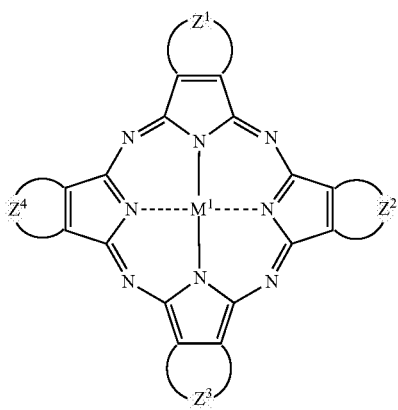

wherein in Formula (A), $M^1$ represents a metal or a metal compound; and $Z^1$, $Z^2$, $Z^3$, and $Z^4$ each independently represents an atom group needed for forming a six-membered ring with atoms thereof selected from the group consisting of carbon, nitrogen, and hydrogen.

<7> The colored photosensitive curing composition of the item <6>, wherein the tetraazaporphyrin-based cyan colorant represented by the Formula (A) is a phthalocyanine colorant represented by the following Formula (B):

Formula (B)

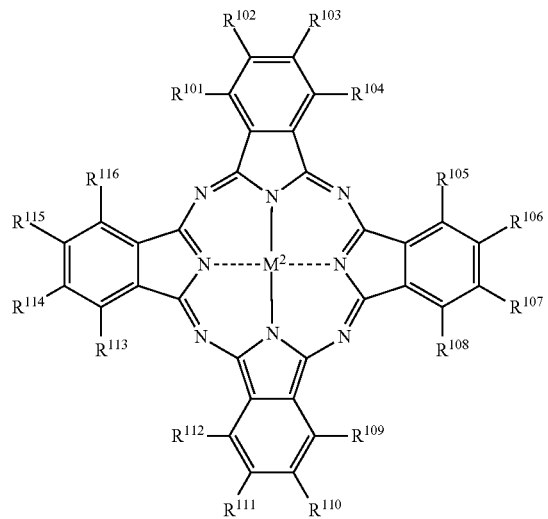

wherein in Formula (B), $R^{101}$ to $R^{116}$ each independently represents a hydrogen atom or a substituent group; and $M^2$ represents a metal or metal compound.

<8> The colored photosensitive curing composition of any one of the items <1> to <7>, further comprising a cyan colorant represented by the following Formula (C):

Formula (C)

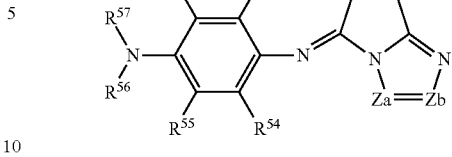

wherein in Formula (C), $R^{50}$ to $R^{55}$ each independently represents a hydrogen atom or a substituent group; $R^{56}$ and $R^{57}$ each independently represents a hydrogen atom or an alkyl, alkenyl, aryl or heterocyclic group; Za and Zb each independently represents —N= or —C($R^{58}$); $R^{58}$ represents a hydrogen atom or a substituent group; and $R^{52}$ and $R^{53}$, $R^{53}$ and $R^{57}$, $R^{54}$ and $R^{55}$, $R^{55}$ and $R^{56}$, and/or $R^{56}$ and $R^{57}$ may bind to each other to form a five-, six-, or seven-membered ring.

<9> The colored photosensitive curing composition of any one of the items <1> to <8>, wherein the dipyrromethene-based compound is a compound represented by the following Formula (IV):

Formula (IV)

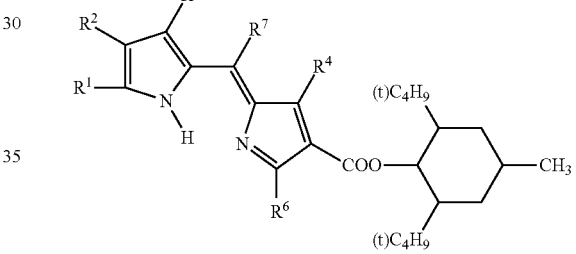

wherein in Formula (IV), $R^1$ to $R^4$ and $R^6$ each independently represents a hydrogen atom or a substituent group; and $R^7$ represents a hydrogen or halogen atom, or an alkyl, aryl or heterocyclic group.

<10> A compound represented by the following Formula (III) or a tautomer thereof:

Formula (III)

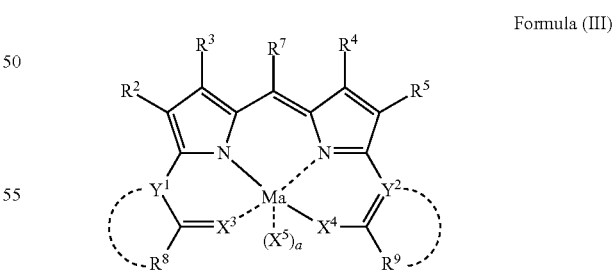

wherein in Formula (III), $R^2$ to $R^5$ each independently represents a hydrogen atom or a substituent group; $R^7$ represents a hydrogen or halogen atom, or an alkyl, aryl or heterocyclic group; Ma represents a metal or metal compound; $X^3$ represents NR (wherein, R represents a hydrogen atom or an alkyl, alkenyl, aryl, heterocyclic, acyl, alkylsulfonyl, or arylsulfonyl group) or a nitrogen, oxygen or sulfur atom; $X^4$ represents NRa (wheren, Ra represents a hydrogen atom or an alkyl, alkenyl, aryl, heterocyclic, acyl, alkylsulfonyl, or arylsulfonyl group) or an oxygen or sulfur atom; $Y^1$ represents NRc (wherein, Rc represents a hydrogen atom or an alkyl, alkenyl, aryl, heterocyclic, acyl, alkylsulfonyl, or arylsulfonyl group) or a nitrogen or carbon atom; $Y^2$ represents a nitrogen or carbon atom; and $R^8$ and $R^9$ each independently represents an alkyl, alkenyl, aryl, heterocyclic, alkoxy, aryloxy, alkylamino, arylamino, or heterocyclic amino group; $R^8$ and $Y^1$ may bind to each other to form a five-, six-, or seven-membered ring; $R^9$ and $Y^2$ may bind to each other to form a five-, six-, or seven-membered ring; $X^5$ represents a group that can bind to Ma; and a is 0, 1, or 2.

<11> A compound represented by the following Formula (IV) or a tautomer thereof.

Formula (IV)

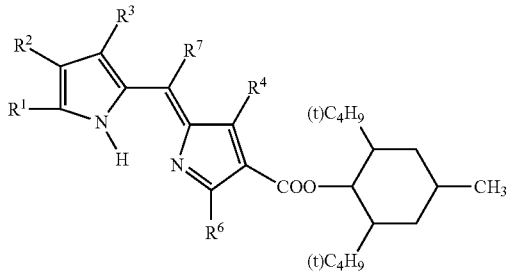

wherein in Formula (IV), $R^1$ to $R^4$, and $R^6$ each independently represents a hydrogen atom or a substituent group; and $R^7$ represents a hydrogen or halogen atom, or an alkyl, aryl or heterocyclic group.

<12> A metal complex compound, obtained from a metal or metal compound and a compound represented by the following Formula (IV):

Formula (IV)

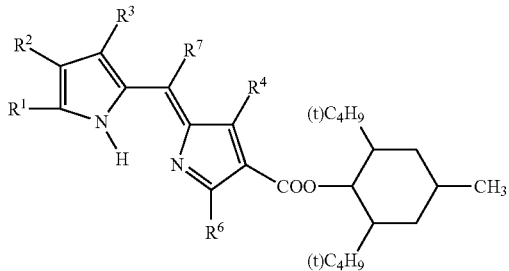

wherein in Formula (IV), $R^1$ to $R^4$, and $R^6$ each independently represents a hydrogen atom or a substituent group; and $R^7$ represents a hydrogen or halogen atom, or an alkyl, aryl or heterocyclic group.

<13> A color filter, prepared using the colored photosensitive curing composition of any one of the items <1> to <9>.

<14> A method of producing a color filter, comprising forming a patterned image by coating a film with the colored photosensitive curing composition of any one of the items <1> to <9>, photoirradiating the coated film through a mask, and developing the resulting coated film.

All publications, patent applications, and technical standards mentioned in this specification are herein incorporated by reference to the same extent as if such individual publication, patent application, or technical standard was specifically and individually indicated to be incorporated by reference.

It will be obvious to those having skill in the art that many changes may be made in the above-described details of the preferred embodiments of the present invention. The scope of the invention, therefore, should be determined by the following claims.

What is claimed is:

1. A compound represented by the following Formula (III) or a tautomer thereof:

Formula (III)

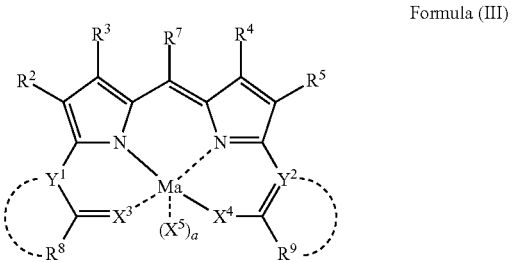

wherein in Formula (III), $R^2$ to $R^5$ each independently represents a hydrogen atom or a substituent group; $R^7$ represents a hydrogen or halogen atom, or an alkyl, aryl or heterocyclic group; Ma represents a metal or metal compound; $X^3$ represents NR (wherein, R represents a hydrogen atom or an alkyl, alkenyl, aryl, heterocyclic, acyl, alkylsulfonyl, or arylsulfonyl group) or a nitrogen, oxygen or sulfur atom; $X^4$ represents NRa (wheren, Ra represents a hydrogen atom or an alkyl, alkenyl, aryl, heterocyclic, acyl, alkylsulfonyl, or arylsulfonyl group) or an oxygen or sulfur atom; $Y^1$ represents NRc (wherein, Rc represents a hydrogen atom or an alkyl, alkenyl, aryl, heterocyclic, acyl, alkylsulfonyl, or arylsulfonyl group) or a nitrogen or carbon atom; $Y^2$ represents a nitrogen or carbon atom; and $R^8$ and $R^9$ each independently represents an alkyl, alkenyl, aryl, heterocyclic, alkoxy, aryloxy, alkylamino, arylamino, or heterocyclic amino group; $R^8$ and $Y^1$ may bind to each other to form a five-, six-, or seven-membered ring; $R^9$ and $Y^2$ may bind to each other to form a five-, six-, or seven-membered ring; $X^5$ represents a group that can bind to Ma; and a is 0, 1, or 2.

2. A metal complex compound, obtained from a metal or metal compound and a compound represented by the following Formula (IV):

Formula (IV)

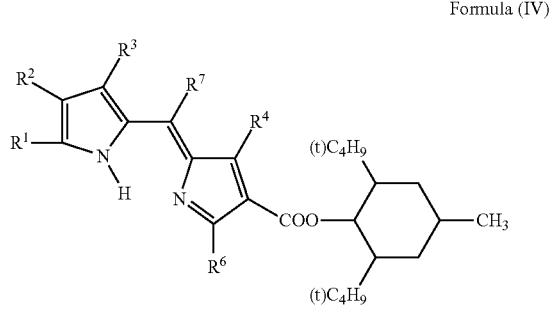

wherein in Formula (IV), $R^1$ to $R^4$, and $R^6$ each independently represents a hydrogen atom or a substituent group; and $R^7$ represents a hydrogen or halogen atom, or an alkyl, aryl or heterocyclic group.

* * * * *